US012638755B2

(12) United States Patent
Abdus-Saboor et al.

(10) Patent No.: US 12,638,755 B2
(45) Date of Patent: May 26, 2026

(54) AUTOMATED REPRODUCIBLE DELIVERY OF MECHANICAL STIMULI IN ANIMAL EXPERIMENTS

(71) Applicant: The Trustees of Columbia University in the City of New York, New York, NY (US)

(72) Inventors: Ishmail John Abdus-Saboor, New York, NY (US); Justin Burdge, New York, NY (US); Z. Anissa Jhumka, Marseilles (FR); Jacob Nazarian, V, Hudson, NH (US); Tanya Tabachnik, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 18/781,138

(22) Filed: Jul. 23, 2024

(65) Prior Publication Data

US 2024/0415625 A1 Dec. 19, 2024

Related U.S. Application Data

(63) Continuation of application No. PCT/US2024/034122, filed on Jun. 14, 2024.

(60) Provisional application No. 63/641,219, filed on May 1, 2024, provisional application No. 63/521,444, filed on Jun. 16, 2023.

(51) Int. Cl.
*A61B 5/00* (2006.01)
*G03B 17/56* (2021.01)

(52) U.S. Cl.
CPC .......... *G03B 17/561* (2013.01); *A61B 5/0048* (2013.01); *A61B 5/4827* (2013.01)

(58) Field of Classification Search
CPC ........... A61B 2503/40; A61B 2503/42; A61B 5/4827
See application file for complete search history.

(56) References Cited

U.S. PATENT DOCUMENTS

| | | |
|---|---|---|
| 10,430,533 B2 | 10/2019 | Kimchi et al. |
| 10,905,094 B2 | 2/2021 | Salem et al. |
| 11,432,528 B2 | 9/2022 | Woolf et al. |

(Continued)

OTHER PUBLICATIONS

Abdus-Saboor, "Using mouse pain scales to discover unusual pain sensitivity and new pain targets," NIH Grant DP2NS130454, Sep. 2022.

(Continued)

*Primary Examiner* — Jennifer Robertson
*Assistant Examiner* — H.Q. Nguyen
(74) *Attorney, Agent, or Firm* — Potomac Law Group, PLLC

(57) ABSTRACT

An animal positioned on a perforated platform can be stimulated in an automated fashion. Images of the animal's paw are captured using a bottom-view camera positioned below the platform. Based on these images, an upwards-pointing tool is moved until it is directly beneath the paw. The animal is then stimulated automatically by moving the tool upwards to contact the paw, then moving it back down to cease the contact. Images of the animal are captured using at least one side-view camera, and these images can be analyzed to ascertain the animal's response to the stimulus.

6 Claims, 39 Drawing Sheets

(56) References Cited

U.S. PATENT DOCUMENTS

| | | | |
|---|---|---|---|
| 2011/0009769 A1* | 1/2011 | Hagau | A61B 5/4824 |
| | | | 600/557 |
| 2012/0029380 A1* | 2/2012 | Ki Chul | A61B 5/0537 |
| | | | 600/547 |
| 2012/0180731 A1 | 7/2012 | Garner et al. | |
| 2012/0234256 A1 | 9/2012 | Harte et al. | |
| 2019/0335708 A1 | 11/2019 | Trottier et al. | |
| 2020/0236901 A1 | 7/2020 | Trottier et al. | |
| 2021/0110550 A1 | 4/2021 | Datta et al. | |
| 2022/0248642 A1 | 8/2022 | Kumar et al. | |
| 2024/0099652 A1* | 3/2024 | Dedek | G16H 40/63 |

OTHER PUBLICATIONS

Apkarian et al., "Human brain mechanisms of pain perception and regulation in health and disease," European Journal of Pain, vol. 9, pp. 463-484, Jan. 2005.
Becker et al., "The basolateral amygdala-anterior cingulate pathway contributes to depression-like behaviors and comorbidity with chronic pain behaviors in male mice," Nature Communications, vol. 14, p. 2198, Apr. 2023.
Bohic et al., "Mapping the neuroethological signatures of pain, analgesia, and recovery in mice," Neuron, vol. 111, pp. 2811-2830, Sep. 2023.
Cai et al., "Brain Circuits Mediating Opposing Effects on Emotion and Pain," The Journal of Neuroscience, vol. 38, No. 28, pp. 6340-6349, Jul. 2018.
Chen et al., "Synchronized activity of sensory neurons initiates cortical synchrony in a model of neuropathic pain," Nature Communications, vol. 14, Article 689, Feb. 2023.
Chiang et al., "Divergent Neural Pathways Emanating from the Lateral Parabrachial Nucleus Mediate Distinct Components of the Pain Response," Neuron, vol. 106, pp. 927-939, Jun. 2020.
Corder et al., "An amygdalar neural ensemble that encodes the unpleasantness of pain," Science, vol. 363, pp. 276-281, 2019.
Crane et al., "Sensory processing in adults with autism spectrum disorders," Autism, vol. 13, pp. 215-228, Jun. 2009.
Datta,"Motion Sequencing for All: Pipelining, Distribution and Training to Enable Broad Adoption of a Next-Generation Platform for Behavioral and Neurobehavioral Analysis," NIH Grant U24NS109520, Apr. 2019.
Dedek et al., "Reproducible and fully automated testing of nocifensive behavior in mice," Cell Reports Methods, vol. 3, p. 100650, Dec. 2023.
Deuis et al., "Methods Used to Evaluate Pain Behaviors in Rodents," Frontiers in Molecular Neuroscience, vol. 10, Article 284, Sep. 2017.
Dixon, "Efficient analysis of experimental observations," Annual Review of Pharmacology, vol. 20, pp. 441-462, 1980.
Francois et al., "A Brainstem-Spinal Cord Inhibitory Circuit for Mechanical Pain Modulation by GABA and Enkephalins," Neuron, vol. 93, No. 4, pp. 822-839, Feb. 2017.
Horiguchi et al., "Isolation rearing reduces mechanical allodynia in a mouse model of chronic inflammatory pain," Pharmacology Biochemistry and Behavior, vol. 113, pp. 46-52, Nov. 2013.
Hu et al., "Analysis of the influences of social isolation on cognition and the therapeutic potential of deep brain stimulation in a mouse model," Frontiers in Psychiatry, vol. 14, Jun. 2023.
Jhumka et al., "Next generation behavioral sequencing for advancing pain quantification," Current Opinion in Neurobiology, vol. 76, p. 102598, Oct. 2022.
Jones et al., "A machine-vision approach for automated pain measurement at millisecond timescales," Neuroscience, vol. 9, p. e57258, Aug. 2020.
Kragel et al., "Generalizable Representations of Pain, Cognitive Control, and Negative Emotion in Medial Frontal Cortex," Nature Neuroscience, vol. 21, No. 2, pp. 283-289, Feb. 2018.

Kuner et al., "Cellular Circuits in the Brain and Their Modulation in Acute and Chronic Pain," Physiological Reviews, vol. 101, pp. 213-258, Jun. 2020.
Lee et al., "A neuroimaging biomarker for sustained experimental and clinical pain," Nat. Med., vol. 27, No. 1, pp. 174-182, Jan. 2021.
Li et al., "A mesocortical glutamatergic pathway modulates neuropathic pain independent of dopamine co-release," Nature Communications, vol. 15, Article 643, Jan. 2024.
Meda et al., "Microcircuit mechanisms through which mediodorsal thalamic input to anterior cingulate cortex exacerbates pain-related aversion," Neuron., vol. 102, No. 5, pp. 944-959, Jun. 2019.
Meng et al., "Distinct basolateral amygdala excitatory inputs mediate the somatosensory and aversive-affective components of pain," J. Biol. Chem., vol. 298, No. 8, p. 102207, Jun. 2022.
Mills et al., "Chronic pain: a review of its epidemiology and associated factors in population-based studies," British Journal of Anaesthesia, vol. 123, Issue 2, pp. e273-e283, Aug. 2019.
Nirogi et al., "Comparison of manual and automated filaments for evaluation of neuropathic pain behavior in rats," Journal of Pharmacological and Toxicological Methods, vol. 66, Issue 1, pp. 8-13, Jul./Aug. 2012.
Okada et al., "Pain induces stable, active microcircuits in the somatosensory cortex that provide a therapeutic target," Science Advances, vol. 7, p. eabd8261, Mar. 2021.
O'Leary et al., "Motor function deficits in the 12 month-old female 5xFAD mouse model of Alzheimer's disease," Behavioural Brain Research, vol. 337, pp. 256-263, Jan. 2018.
Orefice et al., "Peripheral Mechanosensory Neuron Dysfunction Underlies Tactile and Behavioral Deficits in Mouse Models of ASDs," Cell, vol. 166, pp. 299-313, Jul. 2016.
Pereira et al., "SLEAP: A deep learning system for multi-animal pose tracking," Nature Methods, vol. 19, pp. 486-495, Apr. 2022.
Reker et al., "The Operant Plantar Thermal Assay: A Novel Device for Assessing Thermal Pain Tolerance in Mice," eNeuro, vol. 7, No. 2, pp. 1-13, Mar./Apr. 2020.
Schorscher-Petcu et al., "Scanned optogenetic control of mammalian somatosensory input to map input-specific behavioral outputs," Neuroscience, vol. 10, p. e62026, Jul. 2021.
Singh et al., "Mapping Cortical Integration of Sensory and Affective Pain Pathways," Curr. Biol., vol. 30, No. 9, pp. 17903-1715, May 2020.
Tan et al., "Neocortical circuits in pain and pain relief," Nature Reviews Neuroscience, vol. 22, pp. 458-471, Jun. 2021.
Tanimoto et al., "Differential contributions of the basolateral and central nuclei of the amygdala in the negative affective component of chemical somatic and visceral pains in rats," European Journal of Neuroscience, vol. 18, Issue 8, pp. 2343-2350, Oct. 2003.
Tracey et al., "Noxious hot and cold stimulation produce common patterns of brain activation in humans: a functional magnetic resonance imaging study," Neuroscience Letters, vol. 288, No. 2, pp. 159-162, Jul. 2000.
Upadhyay et al., "The Dorsal col. Nuclei Scales Mechanical Allodynia During Neuropathic Pain," bioRxiv, 2024.
Wiltschko et al., "Revealing the structure of pharmacobehavioral space through motion sequencing," Nature Neuroscience, vol. 23, pp. 1433-1443, Sep. 2020.
Woolf, "Unravelling Mechanisms and Novel Therapeutic Targets for Peripheral Neuropathy and Neuropathic Pain," NIH Grant R35NS105076, Dec. 2017.
Zhang et al., "A New Apparatus for Recording Evoked Responses to Painful and Non-painful Sensory Stimulation in Freely Moving Mice," Frontiers in Neuroscience, vol. 15, Article 613801, Feb. 2021.
Zhang et al., "Automated preclinical detection of mechanical pain hypersensitivity and analgesia," Pain, vol. 163, No. 12, pp. 2326-2336, Dec. 2022.
Zhou et al., "A sleep-active basalocortical pathway crucial for generation and maintenance of chronic pain," Nat. Neurosci., vol. 26, No. 4, pp. 458-469, Mar. 2023.
Han et al., "Facilitation of synaptic transmission and pain responses by CFRP in the amygdala of normal rats," Molecular Pain, vol. 6, Article 10, 2010.

(56)          References Cited

OTHER PUBLICATIONS

International Search Report and Written Opinion issued in PCT/US2024/034122 dated Oct. 23, 2024.

* cited by examiner

S10 — CAPTURE IMAGES OF THE PAW FROM BELOW

S20 — MOVE TOOL UNTIL IT IS DIRECTLY BENEATH THE PAW

S30 — BEGIN CAPTURING SIDE IMAGES OF THE ANIMAL

S40 — MOVE THE TOOL UP TO CONTACT THE PAW

S50 — MOVE THE TOOL BACK DOWN

S60 — CONTINUE CAPTURING SIDE IMAGES

S70 — ANALYZE THE CAPTURED SIDE IMAGES

Automated Reproducible Mechano-stimulator (ARM)

Legend:
- Researcher 1 Present
- Researcher 2 Present
- No Researcher Present

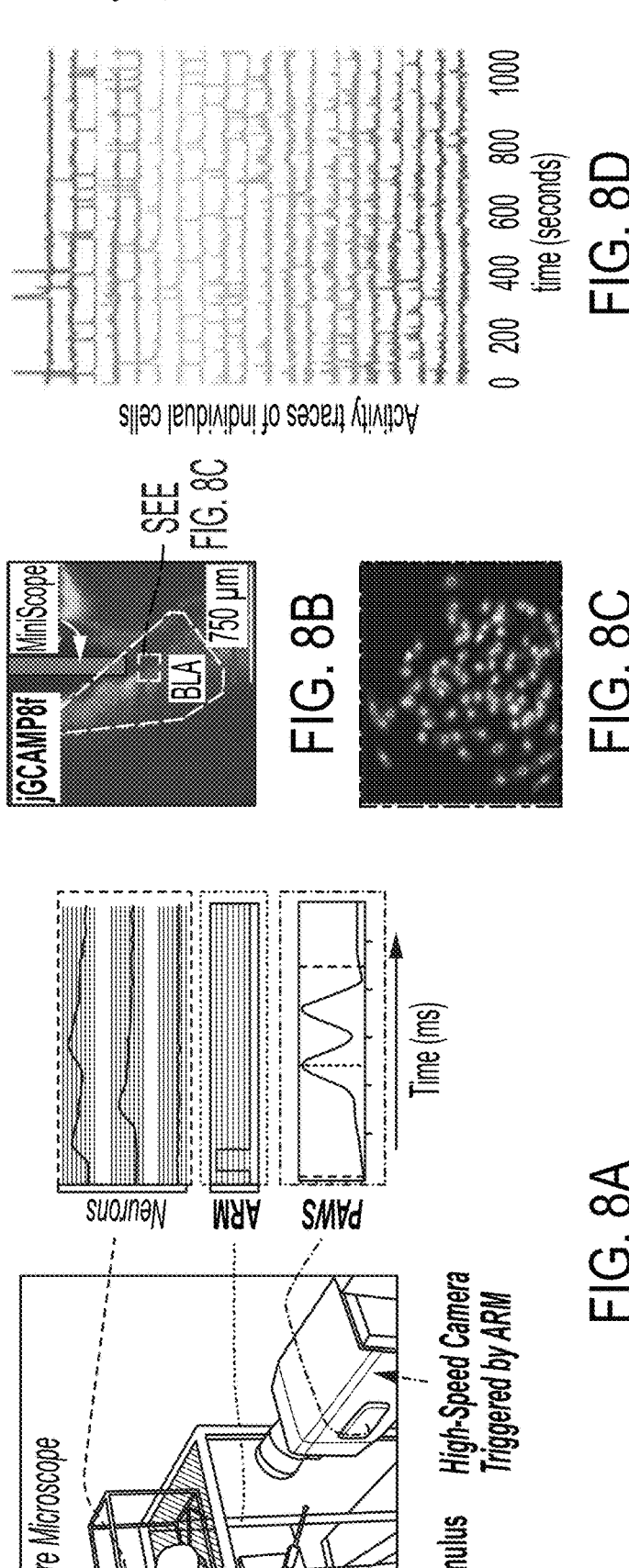

Mesh platform

Stimulus

Stimulus holder

Rotating axis (for stimulus delivery and or rotation)

Z- Axis (for precise up-and-down movement)

Bottom-view camera

Camera-holder (for camera to move with Z-axis tower)

AUTOMATED REPRODUCIBLE DELIVERY OF MECHANICAL STIMULI IN ANIMAL EXPERIMENTS

CROSS REFERENCE TO RELATED APPLICATIONS

This Application is a continuation of PCT/US2024/034122, filed Jun. 14, 2024, which claims the benefit of U.S. Provisional Applications 63/521,444 (filed Jun. 16, 2023) and 63/641,219 (filed May 1, 2024), each of which is incorporated herein by reference in its entirety.

STATEMENT REGARDING FEDERALLY-SPONSORED RESEARCH

This invention was made with government support under NS130454 awarded by the National Institutes of Health. The government has certain rights in the invention.

BACKGROUND

In certain animal experiments, a stimulus is applied to an animal's body, and the animal's response to the stimulus is observed. The stimulus can include, for example, mechanical stimuli such as pricking the animal's paw with a pin, or brushing the animal's paw with nylon filaments, a cotton swab, etc. The traditional approach for testing pain and mechanical sensitivity in mice (or other rodents) is manual delivery of stimuli to the paw. But this approach can be problematic because it requires significant training by the people who perform the experiments, and can be ergonomically challenging for the experimenters. Moreover, the results obtained will often vary from experimenter to experimenter, or even from day to day when a single experimenter performs all the experiments. This makes it difficult to compare data sets from different experimenters and/or different days. This variability in the measured results can make it much more difficult to draw conclusions from the data.

SUMMARY OF THE INVENTION

One aspect of this application is directed to a first apparatus for applying a stimulus to a paw of an animal that is supported by a platform. The platform has a plurality of openings through which the stimulus can be applied to the paw. The first apparatus comprises a motorized XY stage, an actuator, a first tool, a first side-view camera, a bottom-view camera, and at least one controller. The motorized XY stage is positioned beneath the platform, and the XY stage has a base and a movable part. The actuator is mounted to the movable part of the XY stage, and the actuator is configured to, in response to receipt of at least one input command, move a member up by a precise amount and subsequently move the member back down. The first tool is mounted to the member, and the first tool is configured to apply the stimulus to the paw by (a) making contact with the paw through one of the openings in the platform when the member moves up, and (b) ceasing contact with the paw when the member moves back down. The first side-view camera is positioned to capture side views of animals that are positioned on the platform. The bottom-view camera is positioned below the platform to allow visualization of the animal's paw so that the paw can be targeted by the first tool. And the at least one controller is programmed and configured to instruct the XY stage to move the movable part of the XY stage to a location in space at which the first tool is positioned directly beneath the paw, and subsequently send the at least one input command to the actuator.

Some embodiments of the first apparatus further comprise the platform, which has a plurality of openings through which the stimulus can be applied to the paw. In some embodiments of the first apparatus, the first side-view camera is mounted on a first linear stage that is configured to move the first side-view camera horizontally. Some embodiments of the first apparatus further comprise a red or infrared light source aimed to illuminate animals that are positioned on the platform.

In some embodiments of the first apparatus, the first tool is mounted to the member via a rotating component positioned between the first tool and the member. And the apparatus further comprises at least one additional tool mounted to the rotating component so that, depending on a position of the rotating component, a different one of the tools will point up.

Optionally, in the embodiments described in the previous paragraph, the rotating component is configured to rotate to a given one of a plurality of positions based on a command that arrives from the at least one controller, and the at least one controller is further programmed and configured to command the rotating component to rotate to a position at which a given one of the tools points up. Optionally, in the embodiments described in the previous paragraph, the first tool comprises a pin that is shaped and dimensioned to pinprick the paw through the openings in the platform, and the at least one additional tool comprises a brush that is shaped and dimensioned to contact the paw through the openings in the platform.

In some embodiments of the first apparatus, at least one of a trajectory of the stimulus, a speed of the stimulus, and a force of the stimulus is programmable. In some embodiments of the first apparatus, the actuator is configured so that successive actuations of the actuator occur in an identical manner. In some embodiments of the first apparatus, the at least one controller is further programmed and configured to instruct the first side-view camera to begin capturing images 5-200 ms prior to sending the at least one input command to the actuator.

Some embodiments of the first apparatus further comprise a user interface configured to interface with the at least one controller, and the user interface is positioned remotely with respect to the XY stage and the actuator to an extent where the animal will be unaware of a presence of a human operator who is using the user interface.

Some embodiments of the first apparatus further comprise a second side-view camera positioned to capture side views of the animals that are positioned on the platform. The first side-view camera and the second side-view camera are positioned on opposite sides of the animal that is being observed. Optionally, in these embodiments, the second side-view camera is mounted on a second linear stage that is configured to move the second side-view camera horizontally.

In some embodiments of the first apparatus, the at least one controller is further programmed and configured to operate in a mode in which the at least one controller issues commands that cause the movable part of the XY stage to move in a random or pseudo-random pattern in order to habituate the animal to the apparatus. Optionally, in these embodiments, the at least one controller is further programmed to actuate the actuator after at least some of the movements of the movable part of the XY stage.

In some embodiments of the first apparatus, a vertical displacement of the member is sinusoidal during the up and down movements of the member.

Another aspect of this application is directed to a second apparatus for applying a stimulus to a paw of an animal that is supported by a platform. The platform has a plurality of openings through which the stimulus can be applied to the paw. The second apparatus comprises a motorized XY stage, and actuator, and one or more tools. The motorized XY stage is positioned beneath the platform, and the XY stage has a base and a movable part. The actuator is mounted to the movable part of the XY stage, and the actuator is configured to, in response to receipt of at least one input command, move a member up by a precise amount and subsequently move the member back down. The one or more tools are mounted to the member. Each of the one or more tools is configured to apply the stimulus to the paw by (a) making contact with the paw through one of the openings in the platform when the member moves up, and (b) ceasing contact with the paw when the member moves back down.

Some embodiments of the second apparatus further comprise the platform, which has a plurality of openings through which the stimulus can be applied to the paw. This platform can optionally be made from a mesh material or can optionally be made from a perforated sheet of material.

In some embodiments of the second apparatus, the actuator comprises a solenoid. In some embodiments of the second apparatus, the one or more tools comprises a pin that is shaped and dimensioned to pinprick the paw through the openings in the platform.

Some embodiments of the second apparatus further comprise a rotating component that is affixed to the member. The one or more tools comprises a plurality of tools. And the plurality of tools are mounted on the rotating component so that, depending on a position of the rotating component, a different one of the tools will point up.

Optionally, in the embodiments described in the previous paragraph, the plurality of tools includes a pin and a brush. Optionally, in the embodiments described in the previous paragraph, the plurality of tools includes a pin, a brush, and a cotton swab. Optionally, in the embodiments described in the previous paragraph, the plurality of tools includes a member that is heated to a predetermined temperature.

In some embodiments of the second apparatus, at least one of a trajectory of the stimulus, a speed of the stimulus, and a force of the stimulus is programmable. In some embodiments of the second apparatus, the actuator is configured so that successive actuations of the actuator occur in an identical manner.

Some embodiments of the second apparatus further comprise a side-view camera positioned to capture side views of animals that are positioned on the platform, and a bottom-view camera positioned below the platform to allow visualization of the animal's paw so that the paw can be targeted by the one or more tools. Optionally, in these embodiments, the side-view camera is mounted on a linear stage that is configured to move the side-view camera horizontally.

Another aspect of this application is directed to a first method for applying a stimulus to a paw of an animal that is supported by a platform. The platform has a plurality of openings through which the stimulus can be applied to the paw. The first method comprises capturing images of the animal's paw using a bottom-view camera positioned below the platform. The first method also comprises, based on the images captured using the bottom-view camera, moving a first tool until the first tool is positioned below the platform and directly beneath the paw, with the first tool pointing upwards. The first method also comprises moving the first tool upwards so that it makes contact with the paw through one of the openings in the platform and subsequently moving the tool down so that it ceases contact with the paw. The downward movement of the first tool immediately follows the upward movement of the first tool. And the first method also comprises capturing images of the animal from a first lateral side of the animal using a first side-view camera, starting at a time before the first tool makes contact with the paw.

Some instances of the first method further comprise, prior to moving the first tool upwards, moving the first side-view camera horizontally to obtain a view of the animal. Some instances of the first method further comprise illuminating a lateral side of the animal using red or infrared light.

Some instances of the first method further comprise rotating the first tool away from the upward-pointing position and rotating a second tool into the upward-pointing position. Optionally, in these instances, (a) the first tool comprises a pin that is shaped and dimensioned to pinprick the paw through the openings in the platform and (b) the second tool comprises a brush that is shaped and dimensioned to contact the paw through the openings in the platform.

In some instances of the first method, at least one of a trajectory of the first tool, a speed of the first tool, and a force of the first tool is programmable. In some instances of the first method, the motion of the first tool is controlled so that successive movements of the first tool occur in an identical manner. In some instances of the first method, the capturing of images using the first side-view camera, starts 5-200 ms before the first tool makes contact with the paw.

Some instances of the first method further comprise analyzing the images captured using the first side-view camera to ascertain how the animal responds to contact between the first tool and the paw. Some instances of the first method further comprise capturing images of the animal from a second lateral side of the animal using a second side-view camera, starting at a time before the first tool makes contact with the paw. Some instances of the first method further comprise, prior to moving the first tool upwards so that it makes contact with the paw, moving the first tool in a random or pseudo-random pattern in order to habituate the animal to tool movement. In some instances of the first method, a vertical displacement of the first tool is sinusoidal during the upward and downward movements of the first tool.

Another aspect of this application is directed to a third apparatus for applying a stimulus to a body part of an animal. The third apparatus comprises a motorized XY stage, and actuator, a first tool, a side-view camera, a top-view camera, and at least one controller. The motorized XY stage is positioned above the animal, and the XY stage has a base and a movable part. The actuator is mounted to the movable part of the XY stage beneath the XY stage. The actuator is configured to, in response to receipt of at least one input command, move a member down by a precise amount and subsequently move the member back up. The first tool is mounted to the member. The first tool is configured to apply the stimulus to the body part by (a) making contact with the body part when the member moves down, and (b) ceasing contact with the body part when the member moves back up. The side-view camera is positioned to capture side views of animals that are positioned in a confined space. The top-view camera is positioned above the confined space to allow visualization of the body part so that the body part can be targeted by the first tool. And the at least one controller is programmed and configured to instruct the XY stage to move the movable part of the XY stage to a location in space at which the first tool is positioned directly above the body part, and subsequently send the at least one input command to the actuator.

In some embodiments of the third apparatus, the first tool is mounted to the member via a rotating component positioned between the first tool and the member. And the third apparatus further comprises at least one additional tool mounted to the rotating component so that, depending on a position of the rotating component, a different one of the tools will point down.

Optionally, in the embodiments described in the previous paragraph, the rotating component is configured to rotate to a given one of a plurality of positions based on a command that arrives from the at least one controller. And the at least one controller is further programmed and configured to command the rotating component to rotate to a position at which a given one of the tools points down.

In some embodiments of the third apparatus, at least one of a trajectory of the stimulus, a speed of the stimulus, and a force of the stimulus is programmable. In some embodiments of the third apparatus, the actuator is configured so that successive actuations of the actuator occur in an identical manner. In some embodiments of the third apparatus, the at least one controller is further programmed and configured to instruct the side-view camera to begin capturing images 5-200 ms prior to sending the at least one input command to the actuator.

Some embodiments of the third apparatus further comprise a user interface configured to interface with the at least one controller. The user interface is positioned remotely with respect to the XY stage and the actuator to an extent where the animal will be unaware of a presence of a human operator who is using the user interface.

BRIEF DESCRIPTION OF THE DRAWINGS

FIG. 8A depicts a schematic showing alignment of BLA neural activity recorded by a microendoscope.

FIG. 8B depicts the confirmation of injection of jGCaMP8f virus and insertion of Inscopix mini-scope to the BLA.

FIGS. 8C-8D depict the cell map from processed mini-scope recording with a selection of representative deconvolved cell traces in pseudocolors over a 1000 sec window.

Various embodiments are described in detail below with reference to the accompanying drawings, wherein like reference numerals represent like elements.

DESCRIPTION OF THE PREFERRED EMBODIMENTS

This application describes a variety of systems for automating the delivery of mechanical stimuli to the rodents' paws or other body parts. Such systems are referred to herein as an Automated Reproducible Mechano-stimulator (referred to herein as an "ARM").

Example 1

Figure 1:
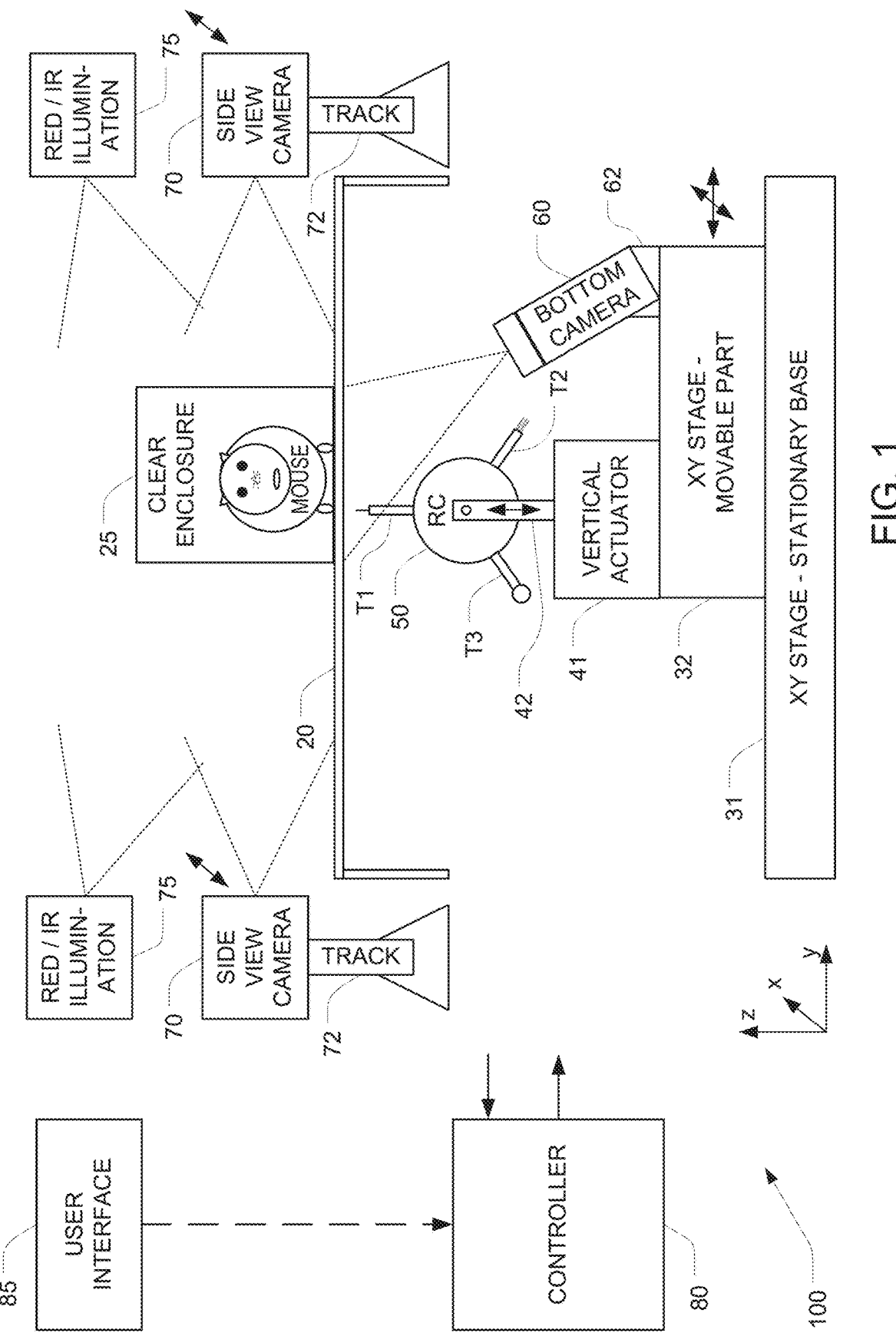
FIG. 1 is a hardware block diagram of a first embodiment of an automated reproducible mechano-stimulator (referred to herein as an "ARM").

FIG. 1 depicts a first ARM embodiment 100 for applying a stimulus to a paw of an animal in order to observe the animal's response to the stimulus. Although the example depicted in FIG. 1 depicts a mouse, the system can also be used to apply a stimulus to other animals. The animal is placed on a platform 20 so that the animal is supported by the platform. Preferably, the animal's movement is restrained so that it cannot leave the platform, and so that its range of motion is limited. This may be accomplished, for example, by positioning the animal in a clear enclosure 25 that does not obstruct visualization of the animal by the side-view cameras 70 that are described below.

The platform 20 has a plurality of openings through which the stimulus can be applied to the paw from below. Examples of suitable ways to implement the platform include making the platform from a mesh material (e.g., metal or plastic), a perforated sheet of material (e.g., metal or plastic), or a sheet of metal that has been slit and expanded to form a larger sheet, etc. Each of these approaches have sufficient structure to support the animal, and a large number of openings through which the stimulus can be applied to the animal's paw.

The stimulus is applied to the animal's paw from beneath the platform by using a tool T1 (e.g. a pin or a brush) that is positioned directly beneath the animal's paw, moving the tool T1 up until it makes contact with the paw, and subsequently moving the tool T1 down until it ceases contact with the paw. Thus, before the stimulus can be initiated, the upper tip of the tool T1 must be moved to a location directly beneath the paw. In the FIG. 1 embodiment, this is accomplished using a motorized XY stage 31-32, a vertical actuator 41, and a rotary component 50 that holds the tool T1.

The motorized XY stage 31-32 is positioned beneath the platform 20, and has a base 31 and a movable part 32. Examples of suitable XY stages that may be used for this purpose include, but are not limited to a Zaber X-LSM050A and X-LSM100A mounted on top of a Zaber LC40B0500-KM01 or X-LRQ300BP-C and X-LRQ600BP-C, as well as similar systems made by Thorlabs and Dover Motion. The controller 80 sends commands to the XY stage 31-32 to move the upper tip of the tool T1 directly beneath the animal's paw.

An actuator 41 is mounted to the movable part 32 of the XY stage, and the actuator 41 is configured to, in response to receipt of one or more input commands that arrive from the controller 80, move a member 42 up by a precise amount and subsequently move the member 42 back down (e.g., to its starting point). The actuator 41 may be implemented using a variety of approaches, including but not limited to the Zaber X-LSM050A, X-LSM100A, or X-LSM200B, which are motorized linear stages that are mounted to move in the Z direction, or other linear stages. Other approaches for implementing this actuator include the Z portion of a commercially available motorized XYZ stage (e.g., made by Thorlabs or Dover Motion), solenoids, a rotary motor combined with a crankshaft, a rotary motor combined with a cylindrical cam, a rotary motor combined with a rack and pinion mechanism, etc.

The nature of the input commands that are used to trigger the actuator 41 will depend on what type of actuator is used. For example, if the Z portion of a motorized XYZ stage is used as the actuator 41, the input commands will include a first command that causes the Z portion to move up by the desired distance at a desired speed, followed by a second command that causes the Z portion to move back down. In another example, if a solenoid is used as the actuator 41, the input command could be a single control bit that the controller 80 sets to raise the solenoid and clears to lower the solenoid.

A first tool T1 (e.g., a pin or a brush of Von Frey hairs (vFH)) is mounted to the member 42, and this first tool is configured to apply the stimulus to the paw by (a) making contact with the paw through one of the openings in the platform 20 when the member 42 moves up, and (b) ceasing contact with the paw when the member 42 moves back down.

In some embodiments (not shown) the first tool T1 is mounted directly to the member 42, in which case the vertical motion of the member 42 will be transmitted directly to the first tool T1. These embodiments are useful when only a single type of tool (e.g., a pin or a brush of Von Frey hairs) is needed to perform all of the experiments required. But in alternative embodiments, the system can be configured to swap different tools into the active position beneath the animal's paw. These embodiments provide the experimenters with more flexibility.

The embodiment depicted in FIG. 1 includes one example of a configuration for swapping different tools into the active position beneath the animal's paws. More specifically, in this example, three different tools T1, T2, T3 are indirectly mounted to the member 42 via a rotating component 50 that is positioned between the first tool T1 and the member 42. The rotating component 50 is configured so that, depending on the position of the rotating component, a different one of the tools T1, T2, T3 will point up. The rotating component 50 is configured to rotate to a given one of a plurality of positions based on a command that arrives from the controller 80, and the controller 80 is programmed and configured to command the rotating component 50 to rotate to a position at which the selected tool points up.

The selection of tools T1, T2, T3 that are installed on the rotating component 50 will depend on the experimental requirements. For example, in some embodiments, the first tool T1 is a pin that is shaped and dimensioned to pinprick the paw through the openings in the platform 20, the second tool T2 is a brush that is shaped and dimensioned to contact the paw through the openings in the platform 20, and the third tool T3 is a cotton swab that is shaped and dimensioned to contact the paw through the openings in the platform 20.

Examples of other tools that may be rotated into the upward-pointing position include members that have been heated to a temperature (e.g., 130-150° F.) that will invoke a response by the animal, infrared light sources that can apply heat to the animal's paw, and visible light sources that can induce optogenetic stimulation. Optogenetic rodent stimulation can be delivered using a mount that holds the optical fiber at a consistent angle and height and allow the ARM to aim the stimulus precisely at the desired target on the paw. The controller 80 triggers the optical stimulus via connection to a signal oscillator attached to the fiber, thereby allowing optical stimulation to be activated remotely.

The rotating component 50 is affixed to the moving member 42 of the vertical actuator 41 so that when the actuator 41 moves the member 42 up by a given distance, the rotating component 50 will move up by that same distance, which will in turn move the upward-pointing tool T1 up by that same distance. Similarly, when the actuator 41 moves the member 42 back down, the rotating component 50 will move down by that same distance, which will in turn move the upward-pointing tool T1 down by that same distance.

Although FIG. 1 depicts a rotating component 50 that is used to swap one of the depicted tools T1-T3 into the upward-pointing position, a variety of alternative approaches may be used to swap any given tool into that position. For example, a robotic arm could select the desired tool from a shelf and clip that tool directly onto the vertical member 42 of the actuator 41.

A side-view camera 70 is positioned to capture side views of animals that are positioned on the platform 20. In the embodiment depicted in FIG. 1, this side-view camera 70 is mounted on a linear stage 72 that is configured to move the side-view camera horizontally. This capability makes it possible to move the side-view camera to a position at which it can most clearly observe the animal, and the x position of the side-view camera can be controlled by the controller 80 by issuing appropriate commands to the linear stage 72. In other embodiments (not shown), the side-view camera 70 can be fixedly mounted, or mounted on a sliding track that allows the x position of the camera to be manually adjusted.

Optionally, a second side-view camera 70 can be positioned to capture different side views of the animals that are positioned on the platform 20. In those embodiments that include this additional side-view camera, the first and second side-view cameras 70 are positioned on opposite sides of the animal that is being observed. When the second side-view camera 70 is provided, it can be mounted on a second linear stage 72 that is configured to move the second side-view camera 70 horizontally.

A bottom-view camera 60 is positioned below the platform 20 to allow visualization of the animal's paw so that the paw can be targeted by the first tool T1. In the example depicted in FIG. 1, the bottom-view camera 60 is mounted to the movable part 32 of the XY stage via a camera mount 62. As a result, when the movable part 32 moves, the bottom-view camera 60 will move together with the movable part. However, in alternative embodiments, the bottom-view camera 60 can be fixedly mounted.

At least one controller 80 is programmed and configured to instruct the XY stage 31-32 to move the movable part 32 of the XY stage to a location in space at which the first tool T1 is positioned directly beneath the paw, and subsequently send the at least one input command to the actuator 41. This will cause the actuator 41 to move the member 42 vertically up and subsequently move the member 42 back down which, as described above, will cause the upward-pointing tool T1 to apply a stimulus to the animal's paw.

Optionally, one or more red or infrared light sources 75 that are aimed to illuminate animals that are positioned on the platform 20 can be included.

Optionally, the speed and force of the stimulus are programmable. In some embodiments, the vertical displacement of the member 42 is sinusoidal during the up and down movements of the member. And because the tool T1 is connected to the member 42, the vertical displacement of the tool T1 in these embodiments will also be sinusoidal during the corresponding up and down movements.

Optionally, a force transducer may be incorporated into the tool T1, the actuator 41, or the rotating component 50. The force transducer sends a signal to the controller 80, which allows the software running on the controller to monitor the force applied to the transducer throughout the ARM's operation. As the stimulus is applied, force can be monitored to determine when the stimulus makes contact with the paw (based on the sensed force increasing), and when the mouse withdraws its paw (based on the sensed force decreasing). This data can will be used to measure withdrawal latency to mechanical stimulus and/or force withdrawal threshold. It can also be used to modify stimulus delivery, either prompting a specific stimulus motion when contact is made with the paw, or withdrawing the stimulus when either a force threshold is met or the mouse withdraws its paw.

The side-view camera 70 is used to capture images of the animal's response to the stimulus. For example, if the animal's paw is pricked by a sharp pin, the animal will withdraw its paw. In view of the high speed of the animal's movements, it is preferable to use a high frame rate for the side-view camera 70. Suitable frame rates include, for example, at least 500 frames per second (fps), at least 1000 fps, or at least 2000 fps. In situations when we are primarily interested in the animal's response to the stimulus, the side-view camera(s) 70 can begin capturing images before the stimulus occurs. This may be accomplished, for example, by having the controller 80 instruct the side-view camera(s) 70 to begin capturing images a short time (e.g., 5-200) ms prior to triggering the actuator 41 (e.g., by sending the at least one input command to the actuator 41). But in alternative embodiments, the controller 80 can instruct the side-view camera(s) 70 to begin capturing images a short time (e.g., 1-5 ms) after triggering the actuator 41 (e.g., by sending the at least one input command to the actuator 41).

Repeatability is often highly desirable when conducting experiments, so in some preferred embodiments the actuator 41 is configured so that successive actuations of the actuator occur in an identical manner.

To reduce variability that may be introduced by the presence of experimenters in the vicinity of the animals, the system can be configured to be operated remotely (e.g., by a human operator in another room). This may be accomplished, for example, by providing a user interface 85 that is configured to interface with the controller 80, and positioning the user interface 85 remotely with respect to the XY stage 31-32 and the actuator 41 to an extent where the animal will be unaware of a presence of a human operator who is using the user interface 85. The user interface 85 can interface with the controller 80 via appropriate cabling or via a suitable wireless protocol (e.g., Bluetooth, Wi-Fi, etc.). And despite the fact that the operator is not in the same room as the mouse, the operator can aim the tool T1 to its desired position based on images captured using the bottom camera 60.

Because the XY stage 31-32 and the actuator 41 move around and make noise during use, there is a concern that the animal could respond to the noise and/or visual cues in addition to responding to the mechanical stimulus that is being applied to the animal's paw. To minimize this concern, the controller 80 can be programmed and configured to issue commands that cause the movable part 32 of the XY stage to move in a random or pseudo-random pattern in order to habituate the animal to the apparatus, and optionally to actuate the actuator 41 after at least some of the movements of the movable part 32 of the XY stage. These movements and actuations should be done prior to subjecting the animal to the mechanical stimulus using the tool T1 (e.g., one or two days before the stimulus is applied) so that the animal can become habituated to the movements of the XY stage 31-32 and the actuations of the actuator 41.

Figure 2:
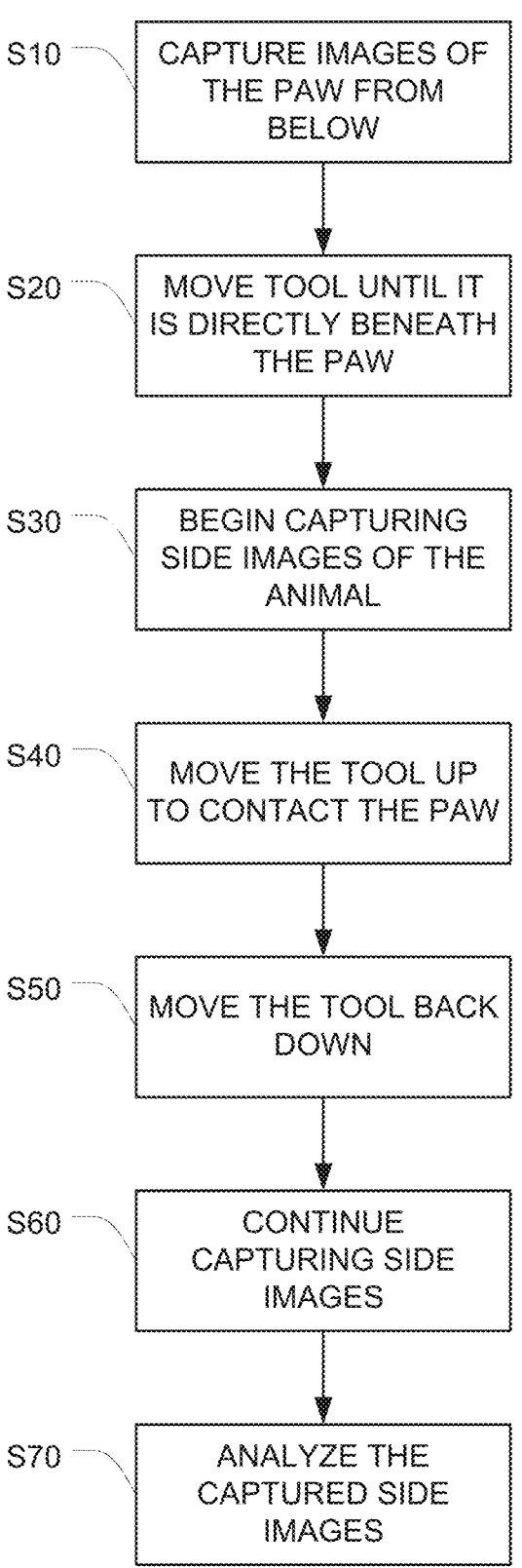
FIG. 2 depicts a method that can be implemented using the hardware depicted in FIG. 1.

FIG. 2 depicts a method that can be implemented using the hardware depicted in FIG. 1. More specifically, this is a method for applying a stimulus to a paw of an animal that is supported by the platform 20 (which, as noted above, has a plurality of openings through which the stimulus can be applied to the paw).

This method begins at S20, during which images of the animal's paw are captured from below using the bottom-view camera 60 (which is positioned below the platform 20). In S20, the tool T1 is moved until it is positioned below the platform 20 and directly beneath the paw, with the tool pointing upwards. Reaching this location relies on the images captured using the bottom-view camera 60 to provide feedback as to where the tool T1 should be positioned.

After the tool T1 has reached its position directly beneath the paw, the system begins capturing side images of the animal at S30.

After the capturing of side images has begun, the tool T1 is moved upwards at S40 so that it makes contact with the paw (through one of the openings in the platform 20) and subsequently moved down at S50 so that it ceases contact with the paw. The downward movement of the tool at S50 immediately follows the upward movement of the tool at S40. Optionally, the vertical displacement of the tool T1 can be sinusoidal during the upward and downward movements of the tool.

The capturing of side images using the side-view camera 70 continues during the up and down movement of the tool at S40-S50, and continues for a time thereafter at S60 for enough time to observe the animal's response to the stimulus.

After performing S10-S60 as described above, the images captured using the side-view camera 70 can be analyzed at S70 to ascertain how the animal responded to contact between the tool T1 and the animal's paw.

Optionally, prior to S30 and S40, the side-view camera 70 can be moved horizontally to obtain a better view of the animal. Optionally, a lateral side of the animal can be illuminated using red or infrared light.

Optionally, Before the tool is moved up and down at S40-S50, one tool can be rotated away from the upward-pointing position and a second tool can be rotated into the upward-pointing position. When this occurs, the second tool is the one that will be used to stimulate the animal's paw.

Optionally, the trajectory, speed, and force of the tool is programmable. Optionally, the motion of the tool can be controlled so that successive movements of the tool occur in an identical manner.

As noted above, the capturing of side images (at S30) begins prior to the upward movement of the tool (at S40). In some embodiments, the capturing of images using the side-view camera 70, starts a short time (e.g., 5-200 ms) before the tool T1 makes contact with the paw.

Although the method described above in connection with S10-S60 refers to a single side-view camera 70, more than one side-view camera 70 can be used to capture images of multiple sides of the animal simultaneously. The second side-view camera 70 is positioned on the other side of the mouse table, either on its own motorized axis or attached to an axis carrying both side-view cameras. The second side-view camera 70 can be set in a holder positioning it so that it can record mouse behavior from the other side of the mouse, which when combined with the bottom-view camera 60 and the original side-view camera 70 would allow for easier recording of withdrawal behavior from either paw and 3D mapping of mouse behavior in response to stimuli. Both side-view cameras 70 can be oriented at the same angle in order to record matching video from both sides of the mouse.

Optionally, prior to moving the tool T1 upwards so that it makes contact with the paw (e.g., at S40), the tool can be moved in a random or pseudo-random pattern in order to habituate the animal to the movement of the tool. This habituation can be implemented, for example, one or two days prior S40.

Optionally, the bottom-view camera 60 may be used capture a sequence of image frames to implement automated aiming of the mechanical stimulus as the mice move freely over time. The relevant image frames can be labeled for desired points including a combination of but not limited to the centers of the left and right hind paws, the snout, and points on the mesh table used to confirm position and scale the image. A pose estimation model can be trained using a portion of this training data and validated with the remaining portion to using either custom software or an existing framework such as Deep lab cut or SLEAP. Additional training data can be added and the model retrained until the desired accuracy is reached. Automated aiming of mechanical stimulus can then be performed using the live feed from the bottom-view camera 60 below the mouse. Using consistent lighting and backgrounds can improve the results.

A live feed of the images captured using the bottom-view camera 60 can be fed through the deep-learning pose estimation model that was previously trained to determine the coordinates of the target paw. The controller 80 will then move the movable part 32 of the XY stage so that the tool T1 aligns with these coordinates and deliver the stimulus. The researcher chooses which mouse, paw, and part of the paw to stimulate and with what stimulus (T1-T3) should be used. This can be done in real-time, one stimulus at a time, or in a preprogrammed sequence that can include a combination of multiple paws and mice.

For each stimulus, the controller 80 will use the coordinates from the live pose-tracking to move the stimulus using the x and y axi to aim the stimulus T1 directly below the desired paw and part of the paw. Additional conditions can include a combination of the paw not moving for a short period of time, facing in a specific direction, and 3-4 paws being on the mesh will then need to be met. Once the stimulus is in place and any conditions are met, the desired stimulus is delivered by actuating the actuator 41 as described above.

Note that while FIG. 1 depicts a single controller 80, the functionality ascribed to that single controller 80 in the above description can be divided between two or more controllers. For example, one controller can be dedicated to controlling the XY stage 31-32 and the vertical actuator 41, while a second controller can be dedicated to analyzing images received from the bottom-view camera 60.

Example 2

Figure 3A:
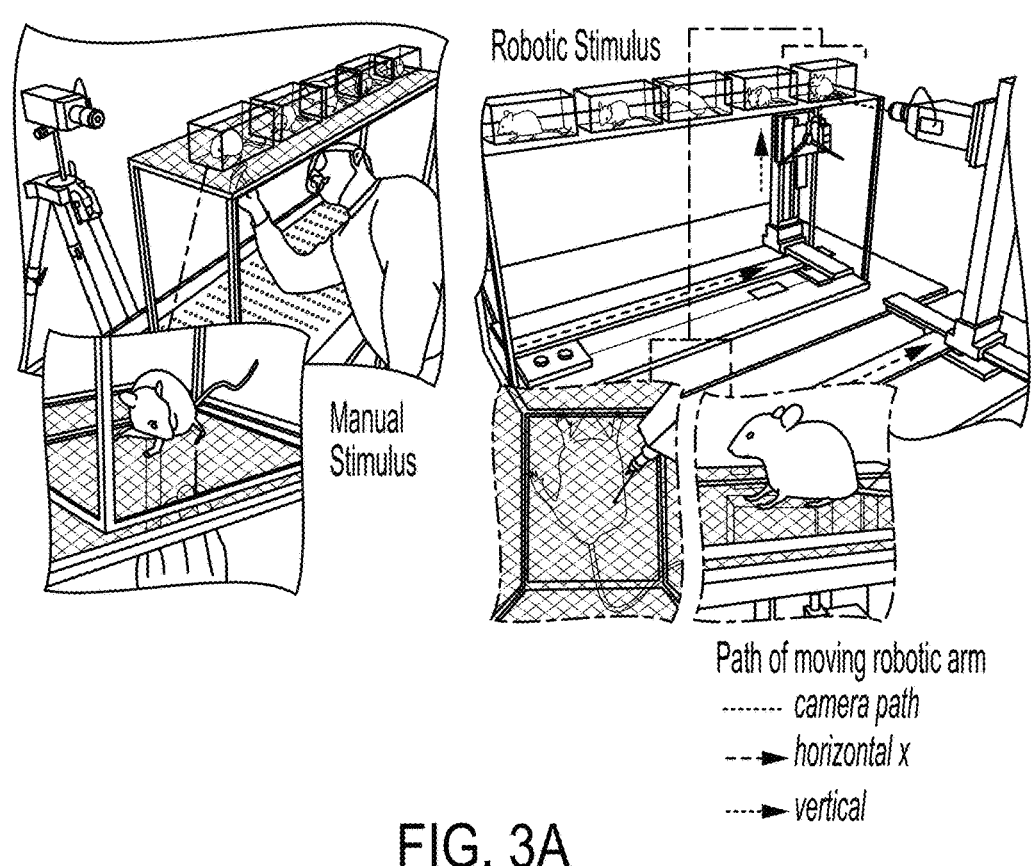
FIGS. 3A and 3B depict a second ARM embodiment that reduces stimulus variability and allows for remote delivery of the stimuli.
Figure 3B:
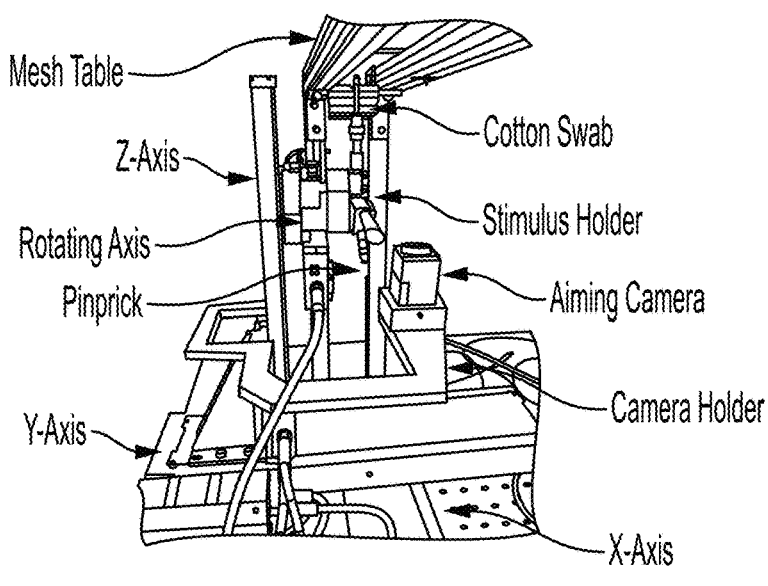

FIGS. 3A-B depict a second ARM embodiment that reduces stimulus variability and allows for remote delivery of the stimuli, and FIGS. 4-14 describe the operation of the FIG. 3 embodiment. This embodiment uses a series of linear stages, cameras, and stimulus holders. Compared to the prior art manual approach, it is more accurate at hitting the desired target, delivers stimuli faster, and decreases variability in delivery of von Frey hair filaments. We demonstrate that the ARM can be combined with traditional measurements of pain behavior and automated machine-learning based pipelines. Importantly, the ARM enables remote testing of mice with experimenters outside the testing room. Using remote testing, we found that mice appeared to habituate more quickly when an experimenter was not present and experimenter presence leads to significant sex-dependent differences in withdrawal behavior. Lastly, to demonstrate the utility of the ARM for neural circuit dissection of pain mechanisms, we combined the ARM with cellular-resolved microendoscopy in the amygdala, linking stimulus, behavior, and brain activity of amygdalar neurons that encode negative pain states. Taken together, the ARM improves speed, accuracy, and robustness of mechanical pain assays and can be combined with automated pain detection systems and brain recordings to map pain sensation and affect.

This ARM can stimulate five freely-moving mice with multiple stimuli within a session. To this end, three linear stages were mounted and wired together to allow for controlled and customizable movement of the stimulus along the x, y, and z-axis. A final rotational axis was attached to the z-axis to allow for both the controlled application of a brush stimulus and the quick switching of stimuli. 3D printed mounts were then attached to the z-axis to hold a camera for aiming the stimulus at the mouse paw and to the rotational axis to hold stimuli. A high-speed camera was then mounted on a linear stage along with an infrared light to allow for the tracking of the mouse's withdrawal response.

This ARM delivers mechanical stimuli to the paw of freely behaving mice. We demonstrated that this device, which is controlled by an experimenter using a standard video game controller, delivers stimuli more accurately, quickly, and consistently than well-trained experts. Moreover, the device can be controlled remotely, removing potential experimenter disturbances of animal behavior. Lastly, the robot arm can be used with traditional read-outs or machine-learning-based measurements of pain and combines seamlessly with brain recording technologies. Combining approaches to deliver pain in the periphery with mapping behavior and brain activity can provide important insights into brain-body connectivity that drives the sensory encoding of pain.

We controlled the ARM with a custom-built Python code that paired the standard Xbox One controller to the bottom-up camera, with calibrated crosshairs superimposed on the camera's video feed. Three types of stimulus delivery were programmed: a simple sin wave motion function along the z-axis for a cotton swab and pinprick stimuli, a combination of concurrent sin waves along the z and radial axis for brush stimuli, and a slow increase in stimulus height over 3 seconds followed by quick retraction for von Frey. Each of these delivery types was designed to replicate the manual delivery of those stimuli. Remote desktop software was then used to allow for control of the device from either across the lab or even across the city.

A habituation program was crafted to be used during habituation sessions and before normal testing to get mice used to the sound and movement of the ARM without stimulus making contact with the mouse. Noise generated by the ARM was observed to be minimal compared to the background HVAC noise. The ARM was assessed for accuracy in both targeting and the force of stimulus delivery. Five different researchers recruited from the lab delivered 10 pinprick stimuli to stationary targets manually and via the ARM. It was found that the FIG. 3 embodiment ARM decreased the off-target distance of stimuli by 93.3% (FIG. 3C), while delivering more consistent stimulus based on analysis of stimulus height with high-speed videography (FIG. 9). This is an important result, as we find that sometimes inexperienced researchers erroneously miss the mouse paw and unknowingly target another part of the animal, like the belly. Regardless of the level of experience, it is extremely difficult to specifically target the same region of the paw within and across stimulus-delivery sessions. The ARM provides the ability to precisely identify and stimulate the desired region in a reproducible manner. This a major strength when investigating biological phenomena at the level of given receptor fields.

Figure 3C:
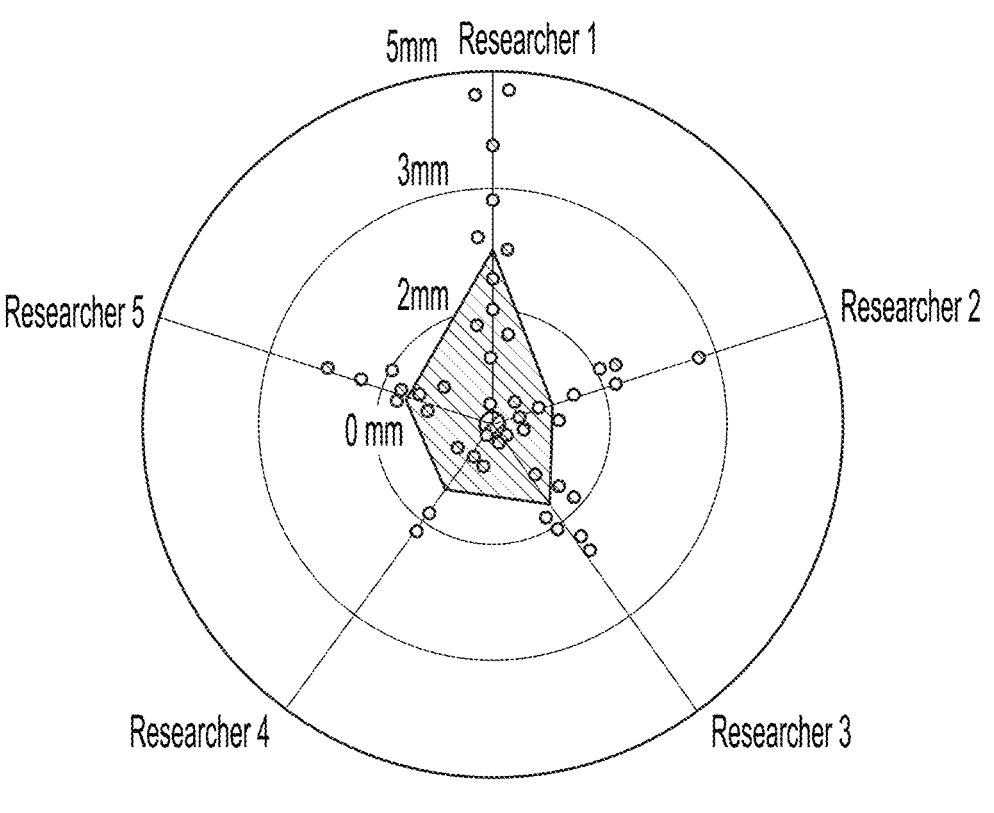
FIG. 3C compares the FIG. 3A-B ARM vs manual stimulus aim.

FIG. 3A compares manual stimulus delivery that requires a researcher to aim and deliver stimulus by hand in close proximity to mice (on the left) vs robotic stimulus delivery via the ARM using motorized linear stages to maneuver and deliver stimulus and a bottom camera to aim (on the right). FIG. 3B is a zoomed in schematic showing components of the ARM including the configuration of the linear axi, the holder attaching the aiming camera to the ARM, the stimulus holder, and the rotational axis that allows for switching between stimuli without detaching components or needing to enter the room. FIG. 3C compares the ARM vs manual stimulus aim. This comparison was conducted by 5 researchers who delivered 10 instances each of manual and ARM pinprick stimulus to a stationary target. A significant (p<0.0001) 93.3% decrease in distance off-target was observed in ARM stimuli delivery compared to manual delivery.

Figures 4A, 4B:
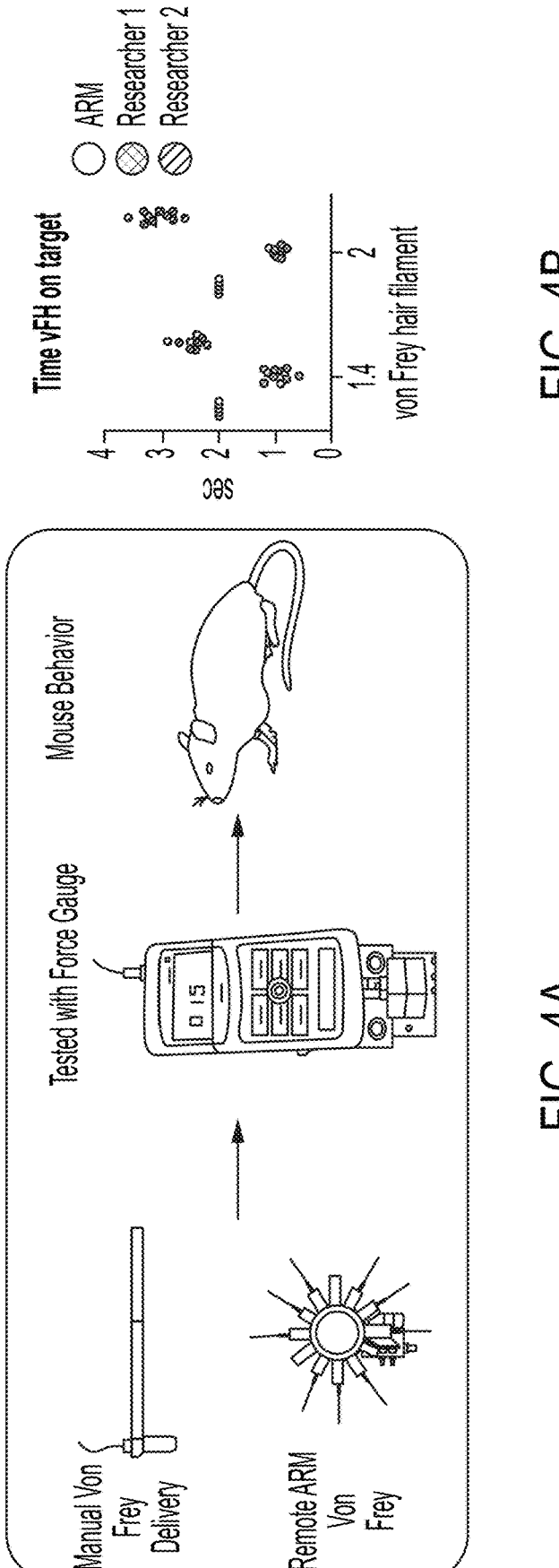
FIG. 4A shows how the ARM and external testers applied vFH stimulus to a force sensor before applying stimuli to a cohort of mice.
FIG. 4B shows that researchers and the ARM user applied stimulus for 2 seconds to the force sensor.
Figure 4C:
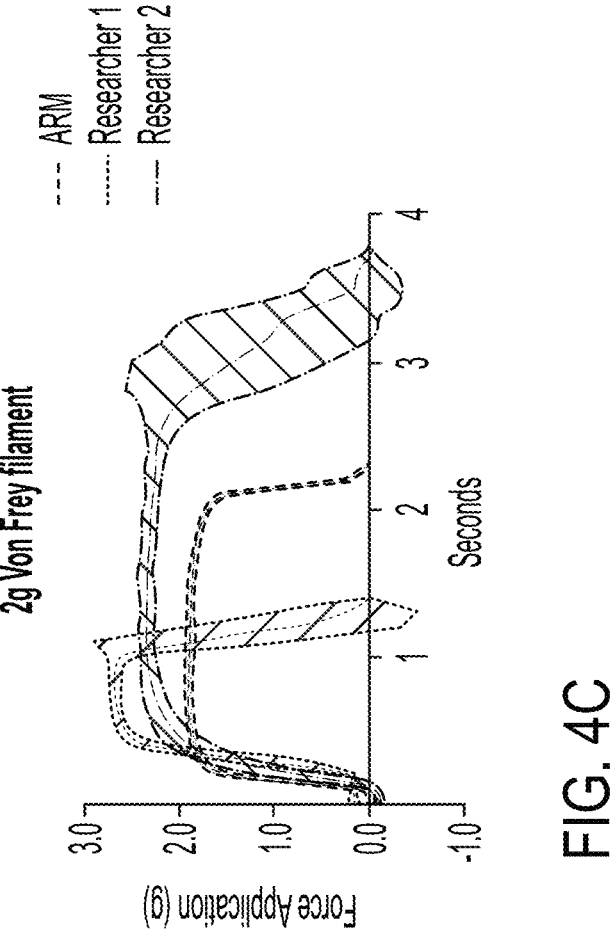
FIG. 4C depicts the standard deviation of all force sensor trials, normalized based on application start time.
Figure 4C:
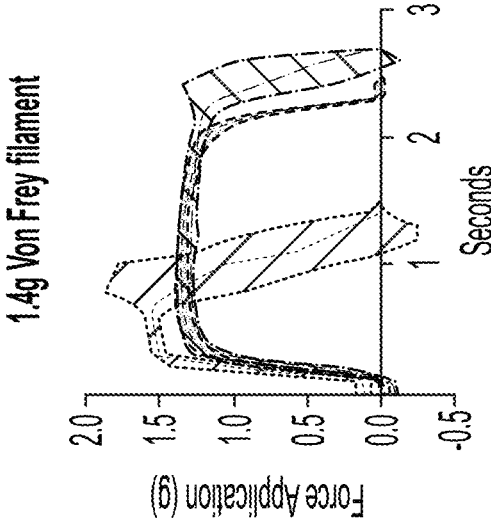
Figures 4D, 4E, 4F:
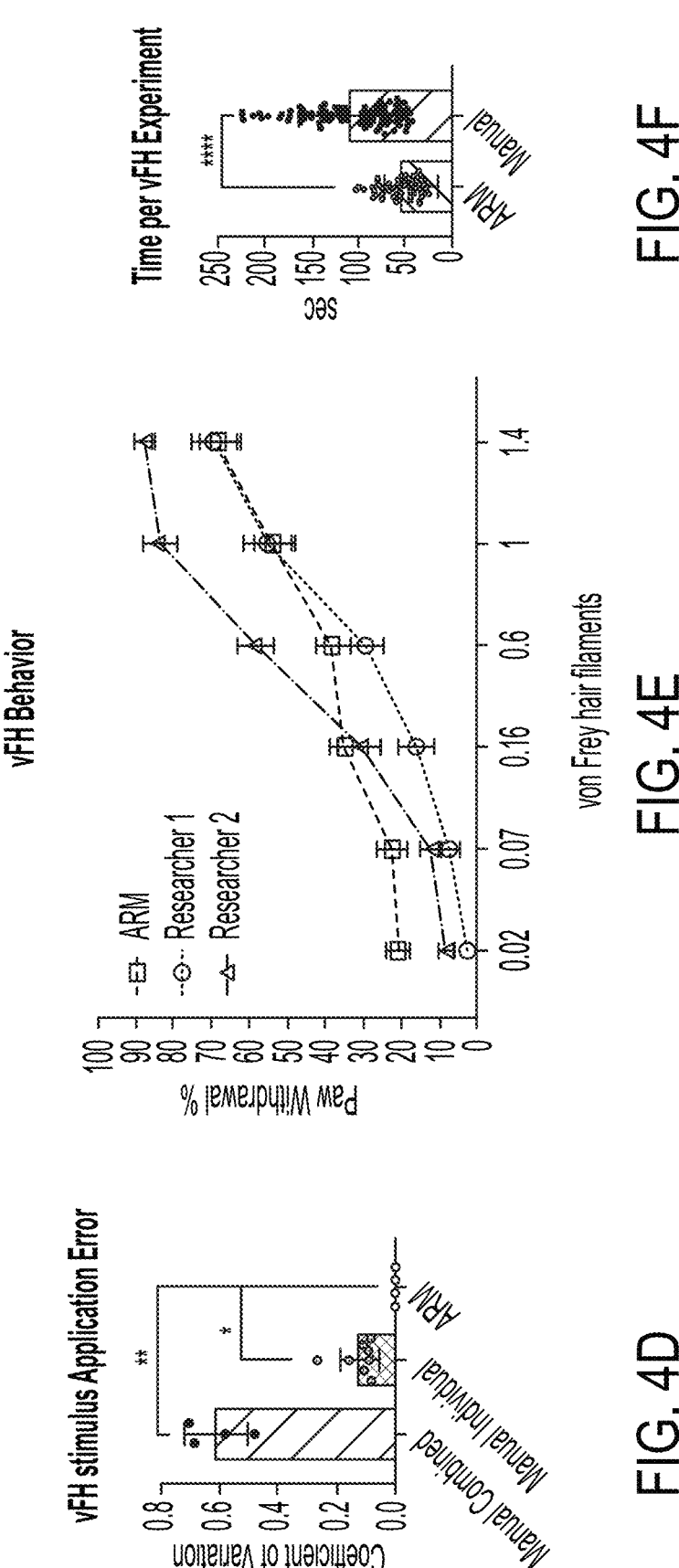
FIG. 4D depicts the coefficient of variance for vFH on target time as determined by the force sensor.
FIG. 4E depicts that both researchers and the ARM tested a cohort of wildtype mice, producing the expected vFH response curves.
FIG. 4F depicts that each set of 10 vFH applications was timed for both manual and ARM stimulus delivery.

FIGS. 4A-F show how the ARM decreases variability in von Frey hair stimulus delivery. More specifically, FIG. 4A shows how the ARM and external testers each first applied vFH stimulus to a force sensor (1.4 g, 2 g) before applying stimuli to a cohort of mice (n=10) and comparing behavior (0.02 g, 0.07 g, 0.16 g, 0.6 g, 1 g, 1.4 g). FIG. 4B shows that researchers and the ARM user were told to apply stimulus for 2 seconds to the force sensor. Time on the sensor was measured. FIG. 4C depicts the standard deviation of all force sensor trials, normalized based on application start time. FIG. 4D depicts the coefficient of variance for vFH (0.6 g, 1 g, 1.4 g, 2g) on target time as determined by the force sensor was calculated for the ARM and compared to each researcher (p=0.0211), and the combined manual trials (p<0.0001) with a one-way anova. FIG. 4E depicts that both researchers and the ARM tested a cohort of wildtype mice (n=10), applying each vFH 10 times to each mouse, producing the expected vFH response curves, includes SEM. FIG. 4F depicts that each set of 10 vFH applications was timed for both manual and ARM stimulus delivery, with the ARM taking on average 50.9% less time to perform each set of applications (p<0.0001, 2-tailed paired t-test).

To test the ARM's performance in delivering traditional von Frey filament stimuli, two external researchers with experience in delivering von Frey stimuli were brought in from the Yang lab in the Department of Anesthesiology to assist with testing. The researchers performed canonical von Frey experiments and were uninformed as to the goals of the study. Both researchers and the ARM applied stimulus to a force sensor in a manner that mimicked their application to the mouse's paw 10 times with 4 filaments before testing a cohort of wild-type mice (n=10) with a range of 6 von Frey filaments (FIG. 4A). Both researchers tested the same cohort of mice and the ARM was used by $3^{rd}$ and $4^{th}$ researcher to test its cohort twice to mimic this. Researchers were instructed to apply von Frey hair stimulus for 2 seconds, and the ARM was programmed to do the same. Each trial with the force gauge was normalized based on the start time, and the mean and standard deviation of the trial were plotted for each researcher and the ARM (FIG. 4C). Higher mean standard deviations were observed in the data for the researchers versus the ARM, driven primarily by variation in vFH application time (FIG. 4B). To quantify this, the coefficient of variation was calculated for the application time of each vFH (0.6 g, 1 g, 1.4 g, 2g) for each researcher and the ARM. The coefficient of variation for the researcher's data combined was also calculated to model variation between researchers. The ARM had no variation in stimulus delivery time, whereas manual stimulus delivery had an average 12.4% variation in the stimulus of individual researchers and 61.17% variation in the stimulus delivery length of the combined researchers (FIG. 4D).

Figures 10A, 10B:
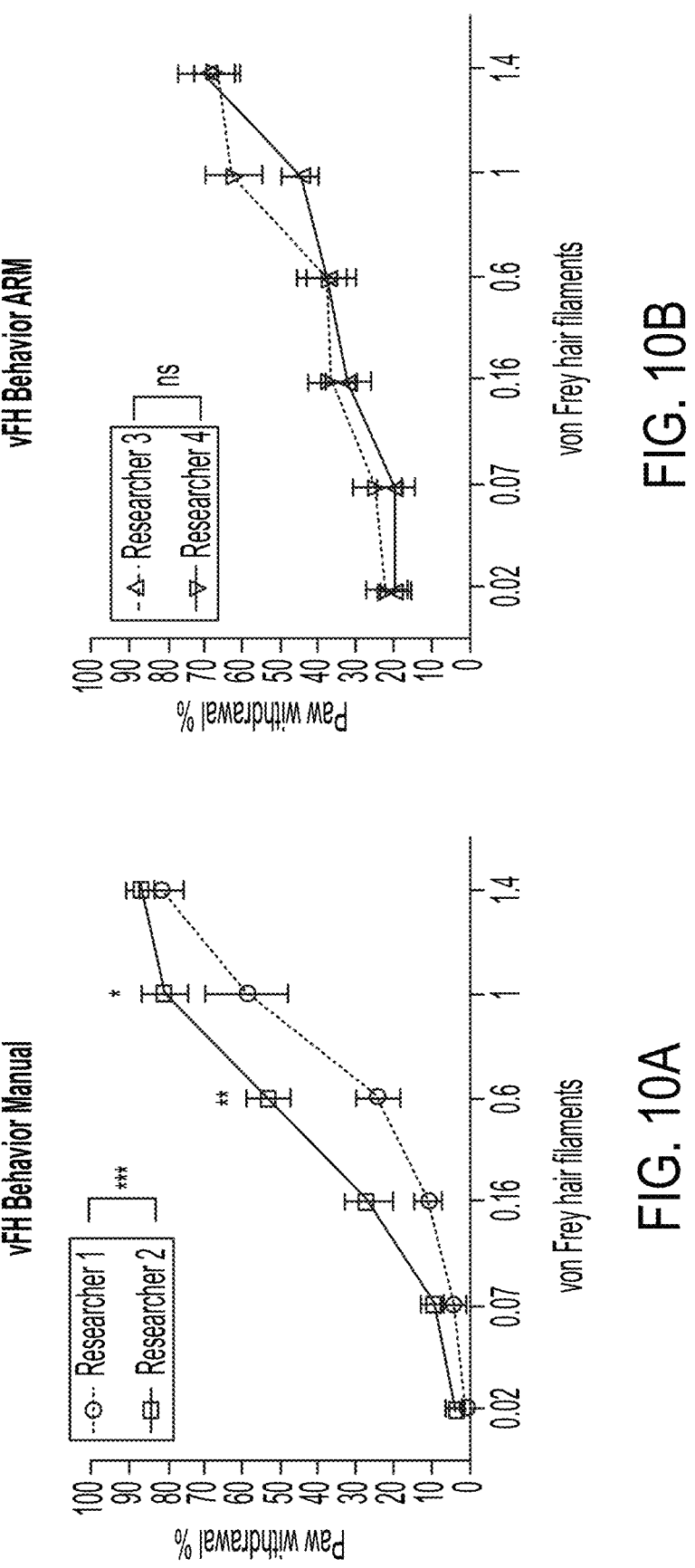
FIG. 10A is a comparison between paw withdrawal frequency elicited by two researchers.
FIG. 10B depicts data when two researchers applied ARM vFH stimulus remotely over two days.

Further, we found that the ARM decreased the time needed to apply a stimulus 10 times to a mouse paw by 50.9% compared to manual delivery (FIG. 4F). Both manual delivery and the ARM produced significant paw withdrawal percentage curves, a standard traditional measurement of mechanical sensitivity in the field (FIG. 4E), with a 2-way ANOVA detecting significant increases in comparing the 3 lower force VFH's (0.02 g, 0.07 g, 0.16 g) to the 2 highest force VFH's (1 g, 1.4 g). This demonstrates that the ARM delivers results comparable to highly experienced researchers. However, a 2-way ANOVA found that Researcher 2 elicited a significantly higher (p=0.0008) paw withdrawal frequency than Researcher 1 (FIG. 10A) which corresponded with Researcher 2's higher VFH application time as measured by the force sensor (FIG. 4B). Comparisons between the $3^{rd}$ and $4^{th}$ researchers applying ARM stimulus remotely found no significant differences in response to either individual vFH or the full data set (FIG. 10B). Thus, these findings indicate that the ARM decreases variation in VFH stimulus used to measure mechanical sensitivity while decreasing the time needed to perform these assays effectively.

The FIG. 3 embodiment provides Improvements in Automated Behavioral Analysis.

Figure 5A:
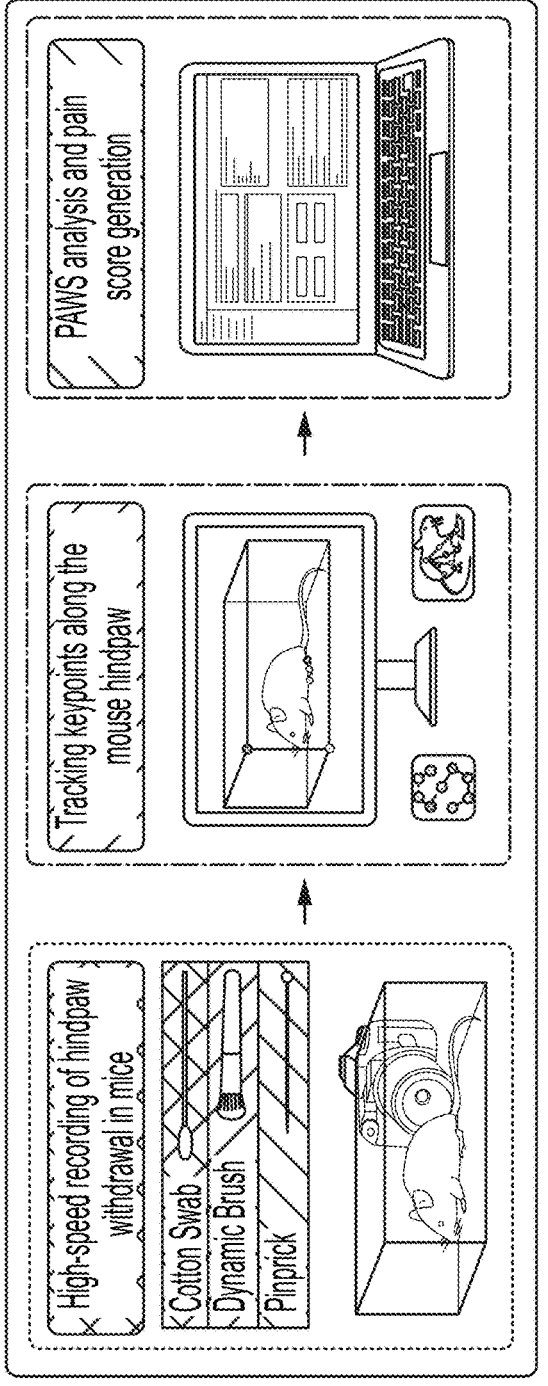
FIG. 5A depicts a schematic outlining high-speed recording to pose tracking (DLC or SLEAP) to updated PAWS software pipeline.
Figure 5A:
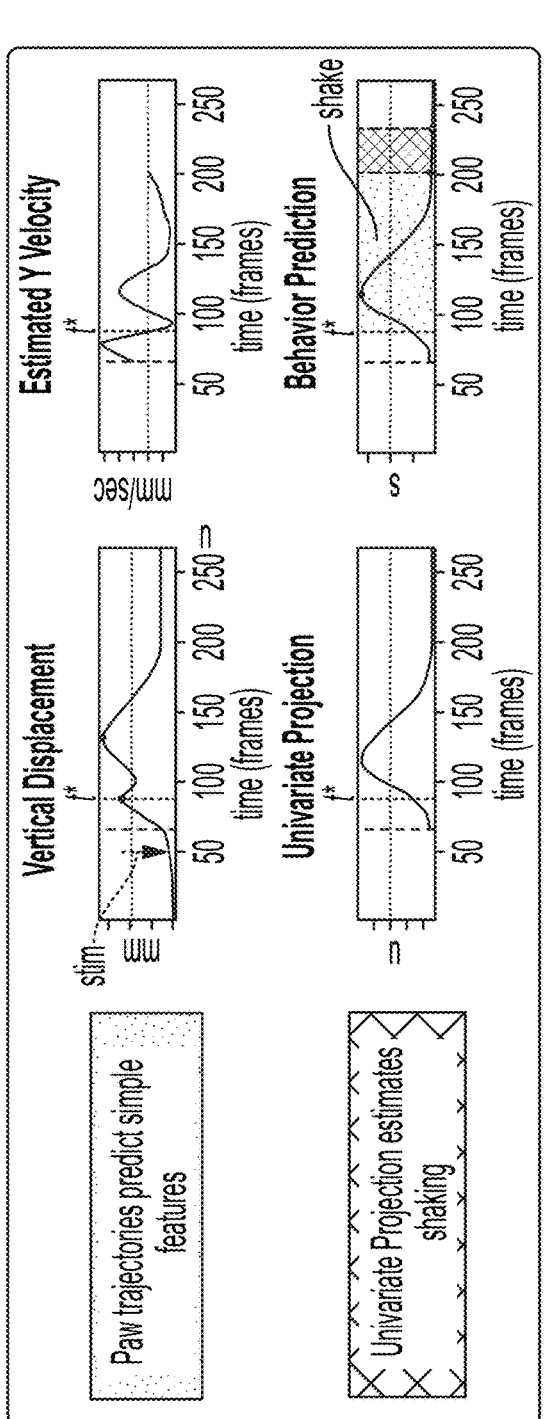
Figures 5B, 5C:
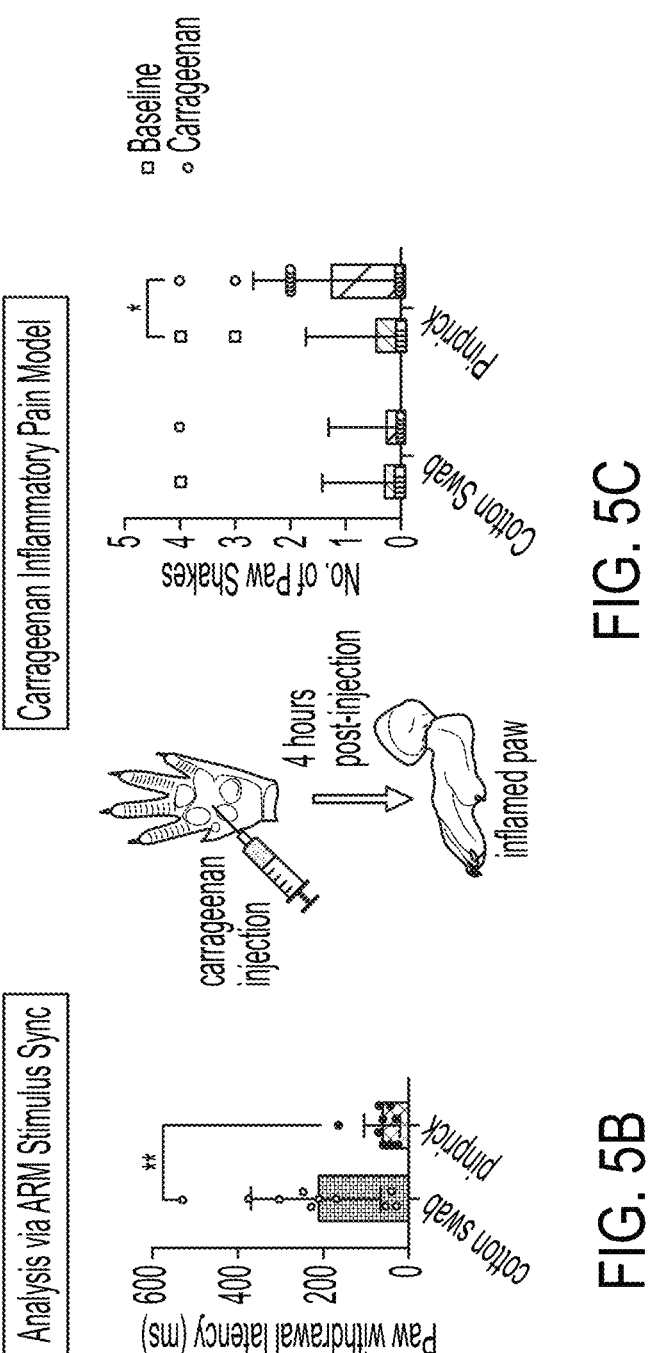
FIG. 5B depicts a stimulus flexible paw withdrawal latency measurement.
FIG. 5C depicts a test of a new PAWS pipeline using a carrageenan inflammatory pain model.

FIGS. 5A-C depict a pain assessment at withdrawal speeds (PAWS) analysis. More specifically, FIG. 5A depicts a schematic outlining high-speed recording to pose tracking (DLC or SLEAP) to updated PAWS software pipeline. The blue dotted line denotes beginning of withdrawal response and t* denotes the peak of the initial reflexive paw withdrawal response, with reflexive features including max height and max Y velocity measured pre t* and affective features including shaking and paw distance traveled measured post t*. FIG. 5B depicts a Stimulus flexible paw withdrawal latency measurement, made possible by syncing ARM stimulus with high-speed video recordings, separates between responses cotton swab and pinprick stimuli (p=0.0081). And FIG. 5C depicts a test of a new PAWS pipeline using carrageenan inflammatory pain model. PAWS detected significantly higher number of paw shakes 4 hours after injection than baseline (p=0.0385).

An updated version of our lab's pain assessment at withdrawal speeds (PAWS) analysis strategy was used to measure the ARM's effect on evoked pain behavior in mice. The ARM's high-speed camera was used to record 2000 fps videos of the mouse's withdrawal response and the movement of the mouse's paw in these videos was then tracked using Social LEAP Estimates Animal Poses (SLEAP) (Pereira 2022). This tracking data was then fed into the PAWS software to compute measures of reflexive and affective pain behavior (FIG. 5A). More details on the PAWS analysis can be found in Jones et al. 2020. To facilitate high throughput analysis, the PAWS software was updated to allow for simple installation on new devices and a full graphical interface. In addition, features were added to allow for the analysis of SLEAP tracking data, greater control over feature scoring, and support for ARM-assisted measurement of withdrawal latency.

To facilitate the measurement of withdrawal latency to mechanical stimuli we used an Arduino to trigger the high-speed camera in response to ARM stimulus delivery. The Arduino was set based on stimuli to trigger the camera 25 milliseconds before the stimulus crossed the mesh and made contact with the paw. Adjustments were then made to the PAWS software to automate the measurement of withdrawal latency based on pose tracking data of the withdrawal response and the trajectory of the stimulus delivery encoded into the ARM. Testing of C57/BL6J (n=15) at baseline found significant decreases in withdrawal latency for pinprick compared to cotton swab stimuli delivered in identical ways by the ARM (FIG. 5B). This decrease was found in both male and female mice indicating that mechanical withdrawal latency can reliably separate between responses to noxious and innoxious mechanical stimuli in rodents. Changes were made to PAWS to make it compatible with framerates lower than 2000 fps. This was tested using a 0.4 MP, 522 FPS, Sony IMX287 camera recording at 500 fps (FIG. 11A-D). The camera paired with PAWS was found to be sufficient to separate between cotton swab and pinprick withdrawal responses, suggesting it may be a useful tool for labs that cannot invest in a more expensive device. PAWS features measured from 500 fps video data had means consistent with data from 2000 fps data. To validate the updated PAWS software and reinforce previous findings, a carrageenan inflammatory pain model was used. Mice injected with carrageenan (n=15) showed elevated shaking behavior (p=0.0385) in response to pinprick stimuli in comparison to measurements at baseline (FIG. 5C). This aligned with previous findings where PAWS has detected elevations in shaking and/or guarding behavior in carrageenan pain models (Bohic et al. 2023).

FIGS. 6-J depict how remote delivery of mechanical stimuli reveals the effects of researcher presence. More specifically, FIG. 6A is a schematic showing the remote operation of the ARM allowing for researcher-agnostic experiments and flexibility. FIG. 6B depicts that male mice (n=10) were habituated either with a researcher present or not for 3 days. Across the 3 days mice rested for the full minute significantly sooner than those with a researcher present (p=0.0217). FIG. 6C depicts the number of times each mouse turned as measured during two 1-minute windows 20-30 minutes each day, normalized by each groups turning behavior during the first 10 minutes of day 1. On day 2 the remote-habituated mice showed significantly decreased turning behavior compared to those habituated with a researcher present (p=0.024). Only the remote-habituated mice showed significantly decreased turning behavior on day 3 compared to day 1 (p=0.0234).

Figure 6A:
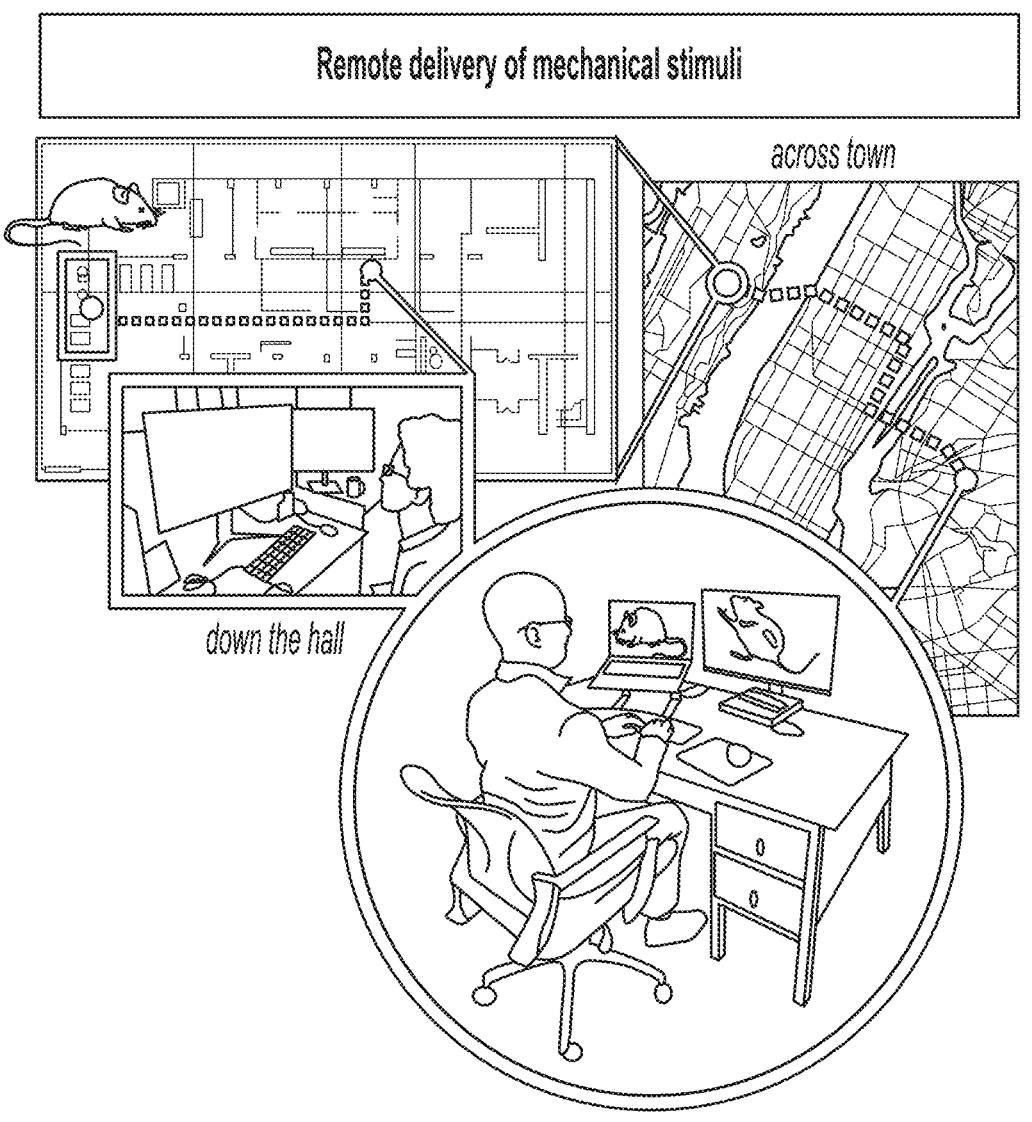
FIG. 6A is a schematic showing the remote operation of the ARM allowing for researcher-agnostic experiments and flexibility.
Figure 6B:
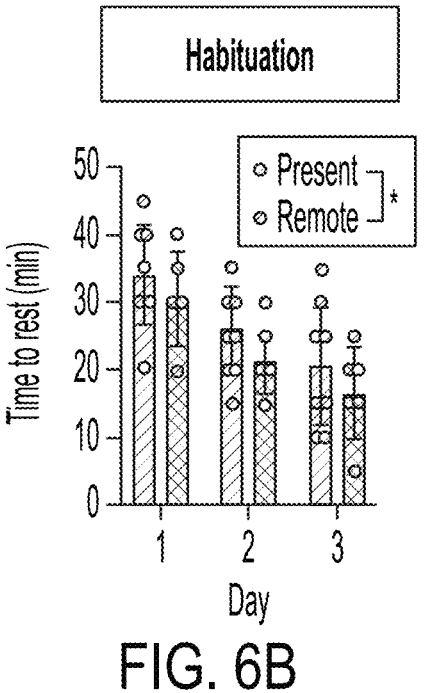
FIG. 6B depicts that male mice were habituated either with a researcher present or not for 3 days.
Figure 6C:
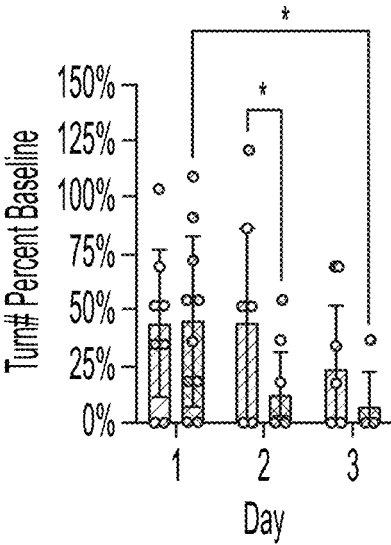
FIG. 6C depicts the number of times each mouse turned as measured during two 1-minute windows 20-30 minutes each day.
Figure 6D:
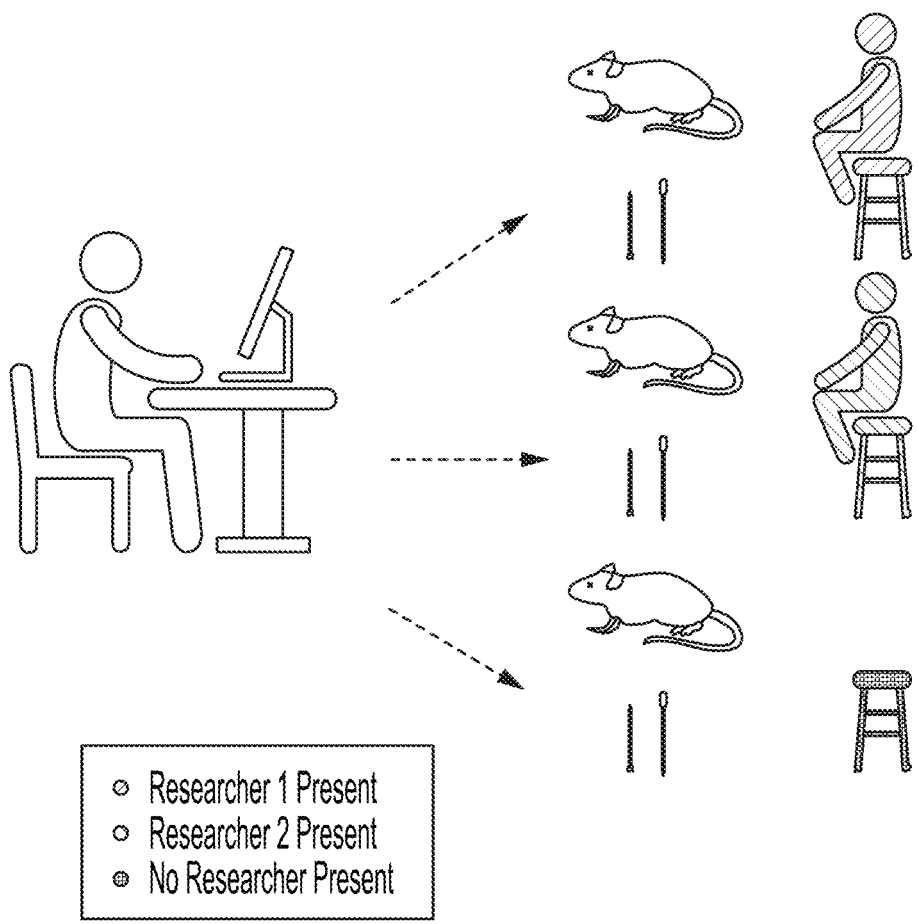
FIG. 6D depicts the experimental schematic showing remote ARM stimulus delivery with either a researcher or no researcher in the room.
Figures 6E, 6F, 6G:
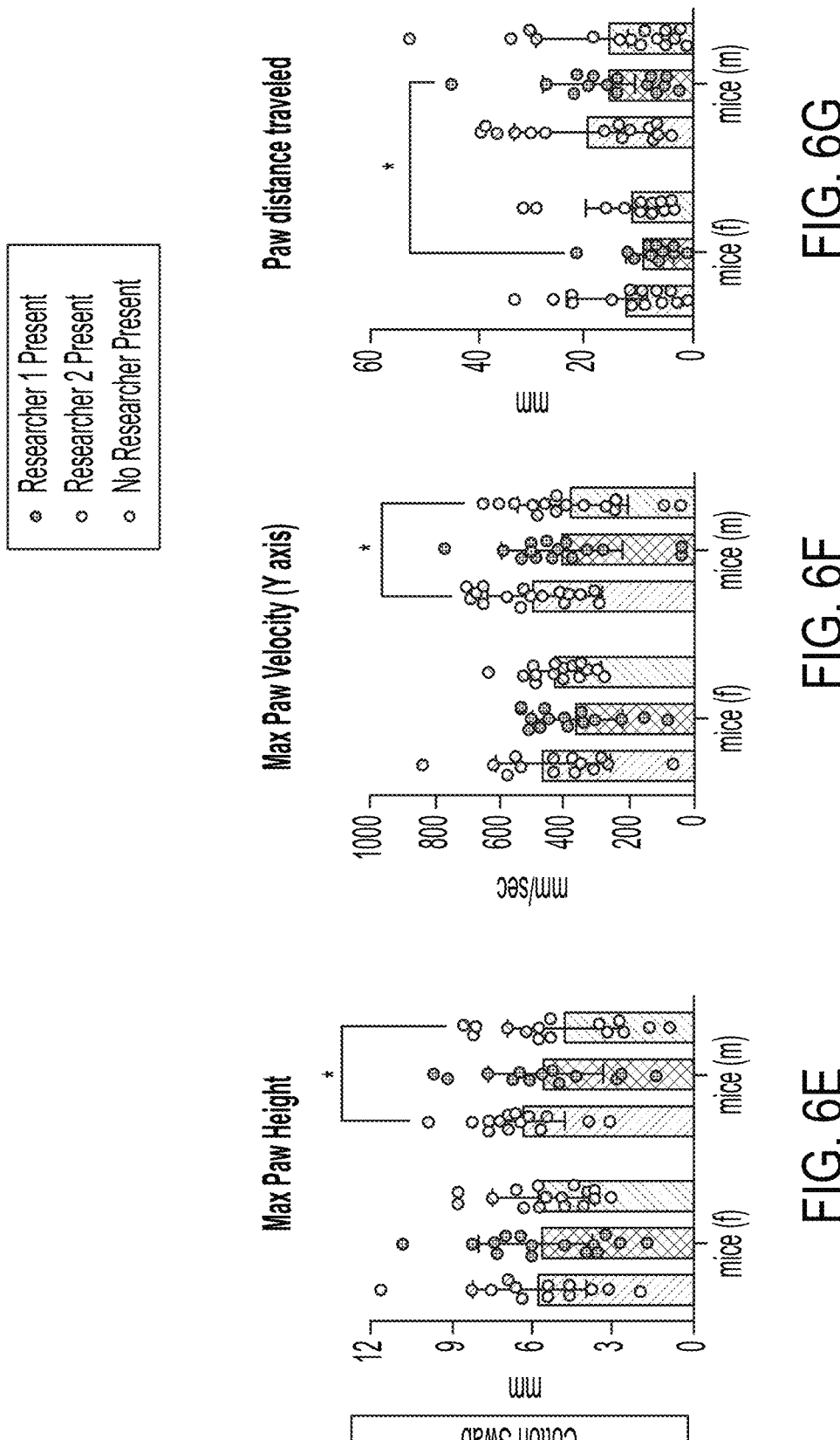
FIGS. 6E-6F depicts a 2-way Anova found significant differences in max paw height and velocity in response to cotton swab for male mice when a researcher was present compared to no researcher.
FIG. 6G depicts the sex-dependent differences were found in response to cotton swab when a researcher was present for distance traveled.
Figures 6H, 6I, 6J:
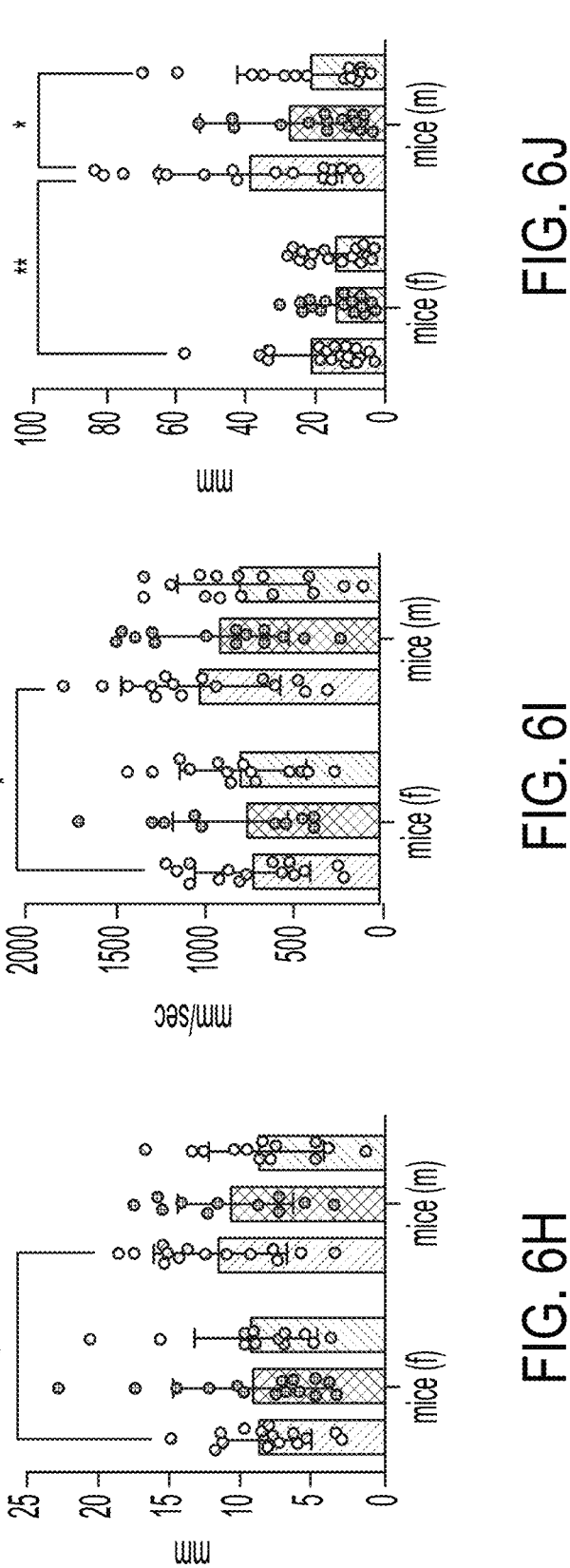
FIGS. 6H-6J depict that sex-dependent differences were found in response to pinprick stimuli when a researcher was present.

FIG. 6D depicts the experimental schematic showing remote ARM stimulus delivery with either a researcher or no researcher in the room. FIGS. 6E-F depicts a 2-way Anova found significant differences in max paw height (p=0.0413) and max Y velocity (p=0.0406) in response to cotton swab for male mice when researcher 2 was present compared to no researcher. FIG. 6G depicts that sex-dependent differences were found in response to cotton swab when Researcher 1 was present for distance traveled (p=0.0468). FIGS. 6H-J depict that sex-dependent differences were found in response to pinprick stimuli when Researcher 2 was present, but not other conditions for max paw height (p=0.0436), max Y velocity (p=0.0424), and distance traveled (p=0.0038). Male mice showed significant differences in paw distance traveled (P=0.0149) when Researcher 2 was present compared to when none was.

The FIG. 3 ARM was successfully used to isolate the effect of the researcher's presence on the mouse withdrawal response.

Previous research has found that experimenter sex can have a significant effect on sensitivity to stimulus due to stress-induced analgesia (Sorge 2014). It was previously not possible to measure this effect when a researcher was present but not giving a stimulus or when no researcher was present during stimulus delivery. Our remote setup of the ARM though makes this possible (FIG. 6A). First to determine the effect of researcher presence on habituation two cohorts of male mice (n=10) were habituated for 3 days, 40 minutes each day with either a researcher present or monitored remotely. Mice were monitored for both the number of times they turned 180° in their chambers and the first point at which they went for a minute resting (no turning, investigating, or grooming). Remote habituated mice showed a significant decrease (p=0.0217) in time to rest over the 3 days (FIG. 6B), but no significant differences for any single day. The number of turns was measured for each group during the first 10 minutes of day 1 to act as a baseline, and then from 20 to 30 minutes for each day. Turn counts were then compared as a percentage of the baseline count for each group. This period was chosen as it the period when experiments start after the day of habituation on experimental days. It was found that remote-habituated mice showed significantly less turning on day 2 compared to mice habituated with a researcher present (p=0.024), and that only the remote-habituated mice showed significantly decreased turning behavior on day 3 compared to day 1 (p=0.0234) (FIG. 6C). These findings indicate that mice take longer to habituate to experimental conditions when an experimenter is present.

To determine the effect of the experimenter's presence in isolation, a cohort of wildtype male and female mice were given an innocuous (cotton swab) and then noxious (pinprick) stimuli via remote control of the ARM when either one of two researchers or no researcher was present (FIG. 6D). Experiments were designed so that circadian rhythm, order of experiments, or day of experiment would not confound the results. Researcher 1 was a male graduate student and researcher 2 was a female lab technician.

Sex-dependent differences were found in reflexive and affective behavioral components of the mouse withdrawal response when a researcher was present versus not for both reactions to innocuous and noxious stimuli. A 2-way ANOVA found that cotton swab stimuli elicited increased male mouse reflexive paw withdrawal features including max paw height (p=0.0413) and max paw velocity (Y-axis) (p=0.0424) when Researcher 2 was present compared to when no researcher was present (FIG. 6E-F). Pinprick stimuli (FIG. 6H-I) on the other hand led to increased max paw height (p=0.0436) and max paw velocity (Y-axis) (p=0.0406) in male mice compared to female mice when Researcher 2 was present.

Analysis of the shaking behavior elicited by cotton swab and pinprick stimuli found no significant differences in shaking behavior duration (FIG. 12A-B) but found sex-dependent differences in paw distance traveled after the initial withdrawal, including during shaking and guarding behaviors. For cotton swab (FIG. 6G) male mice showed significantly increased paw distance traveled compared to female mice when Researcher 1 was present (p=0.0468) but not when Researcher 2 was present or no researcher was present. Pinprick stimuli also elicited sex-based increases in paw distance traveled (FIG. 6J) in male mice when Researcher 2 was present compared to both male mice when no researcher was present (p=0.0149) and female mice when Researcher 2 was present (p=0.0038).

These results indicate that researcher presence at baseline can lead to significant differences in reflexive and affective pain behavior. In this case, male mice showed increased behavioral responses to both touch and pain behavior depending on the researcher present. This led to sex differences in the affective and reflexive component of the withdrawal response when a researcher is present that disappears when no researcher is present, or a different researcher is present. These findings indicate that sex-dependent differences in evoked pain behavior can appear and disappear based on which researcher/s are in the room. This presents a confound that must be considered in the analysis of sex differences in pain and touch behavior which may explain some of the variation in findings from different researchers. Together, these results show that remote stimulus delivery can eliminate variation caused by experimenter presence while making it easier to compare with data from researchers in your lab and others.

Variation in stimulus delivery significantly affects mouse behavioral response.

An analysis of high-speed videos of manual pinprick stimulus delivery found substantial variation in the speed, angle, timing, and max height of the stimulus.

Figure 7A:
FIG. 7A depicts a schematic showing how stimulus delivery variation was modeled through changing pinprick intensity by increasing/decreasing pinprick apex and velocity.
Figure 7A:
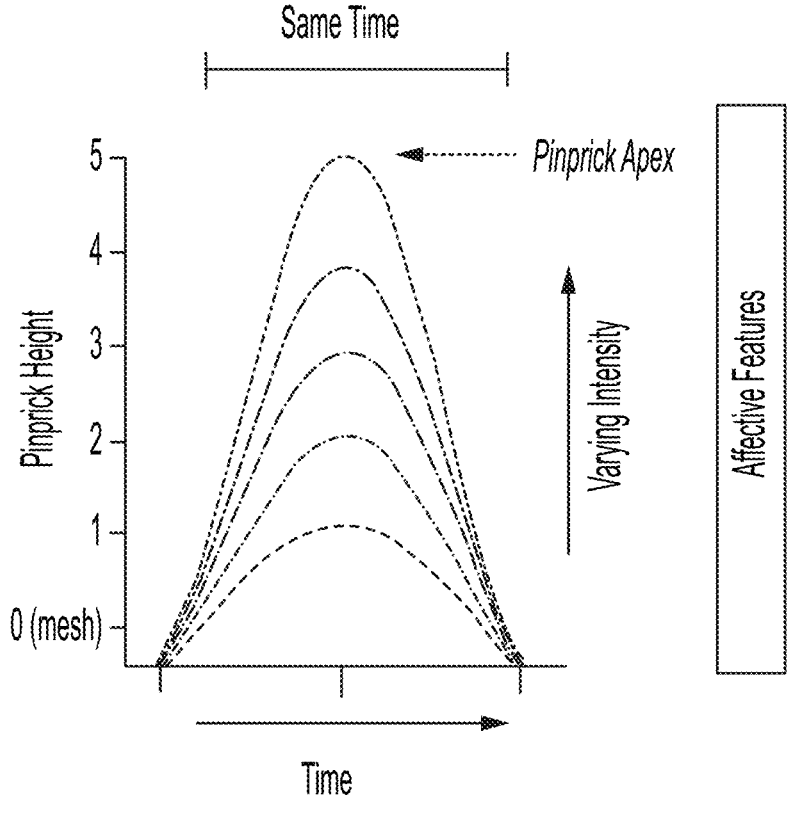
Figures 7B, 7C:
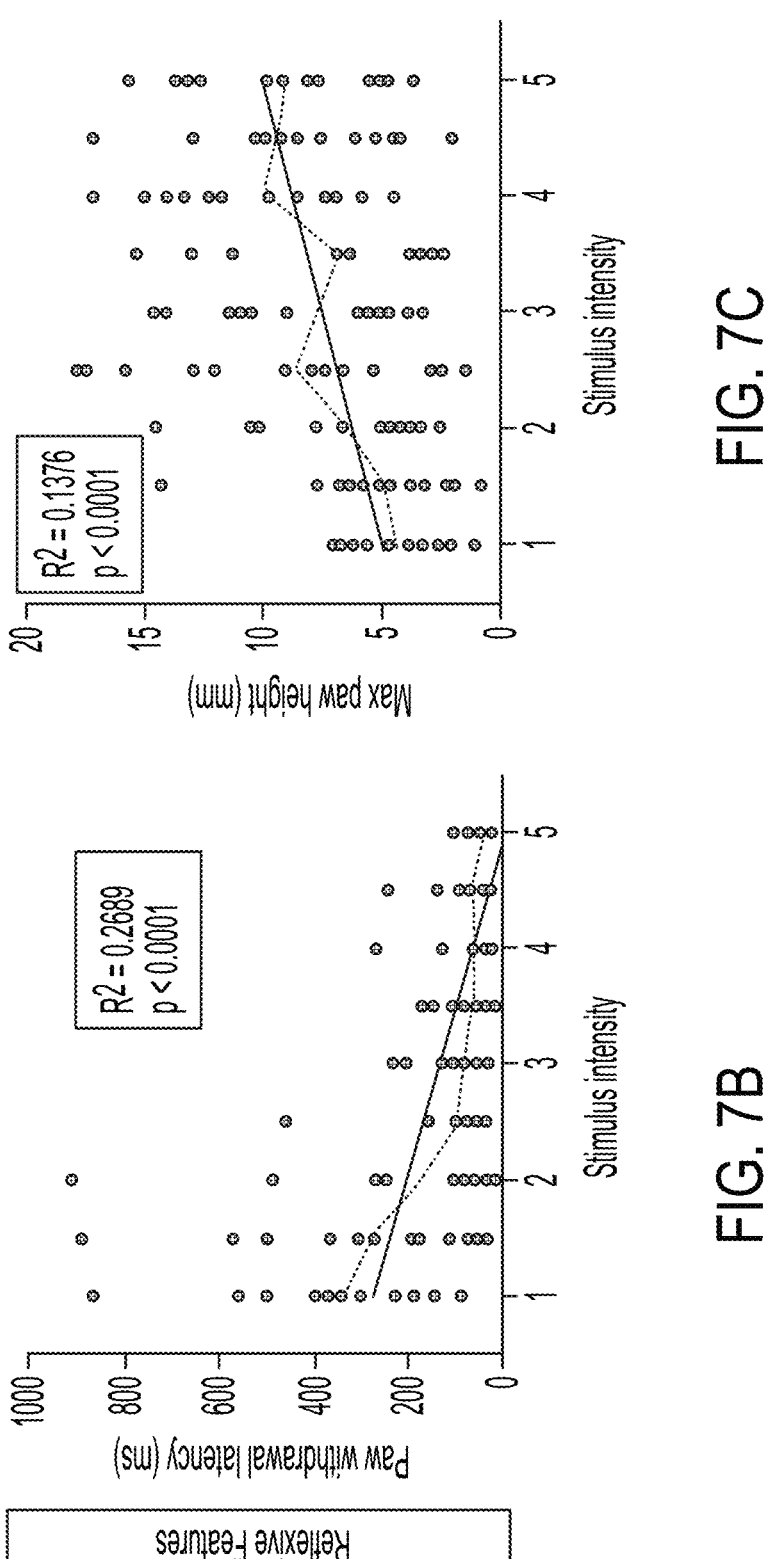
FIGS. 7B-7C depicts the reflexive features were found to correlate with stimulus intensity.
Figures 7D, 7E:
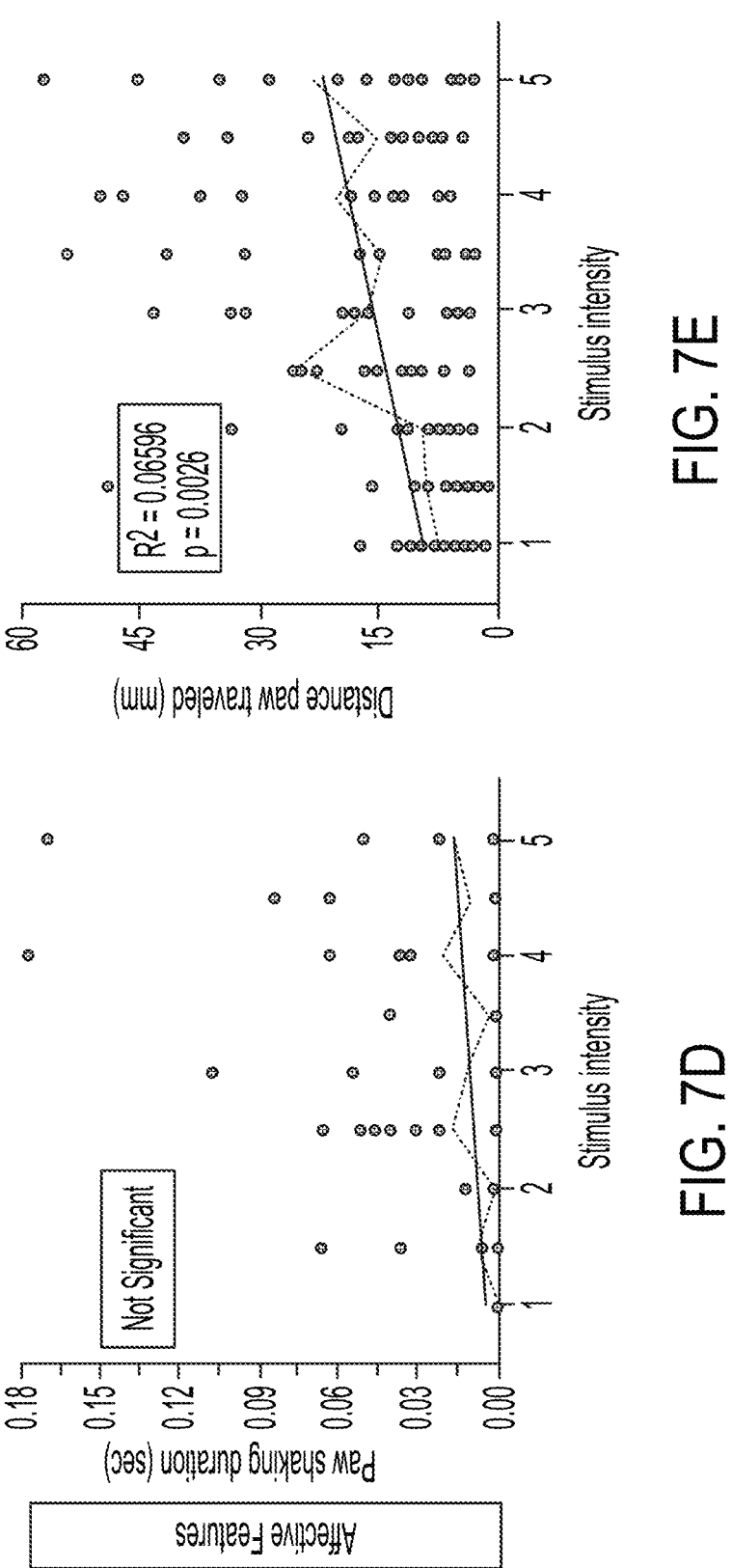
FIGS. 7D-7E depict that for affective features, paw shaking time showed no significant correlation with stimulus intensity and paw distance traveled showed a positive correlation.

FIGS. 7A-E depict isolating the effect of variation in the application of pinprick stimulus. More specifically, FIG. 7A depicts a schematic showing how stimulus delivery variation was modeled through changing pinprick intensity by increasing/decreasing pinprick apex and velocity. FIGS. 7B-C depicts the Reflexive features were found to correlate with stimulus intensity based on a simple linear regression, withdrawal latency with a negative correlation and max paw height with a positive correlation. FIGS. 7D-E depict that for affective features, paw shaking time showed no significant correlation with stimulus intensity and paw distance traveled showed a positive correlation.

This variation was apparent between researchers and within tests from a single researcher. It was predicted that stimulus variability would not fully explain the variation in behavioral responses, as other environmental factors-such as experimenter presence and innate variability in animal behavior-also contribute, but would contribute significantly to that variability and could skew data, if biased. To determine the effects of variation in stimulus intensity on mouse withdrawal response, a cohort of male wildtype mice (n=15) were given pinprick stimulus 9 times across 3 days, each with a different stimulus apex (1-5 mm above the mesh), but with time to apex and total time above mesh kept consistent (FIG. 7A). This was done to keep the total potential stimulus exposure time consistent while varying intensity.

Figures 8E, 8F, 8G:
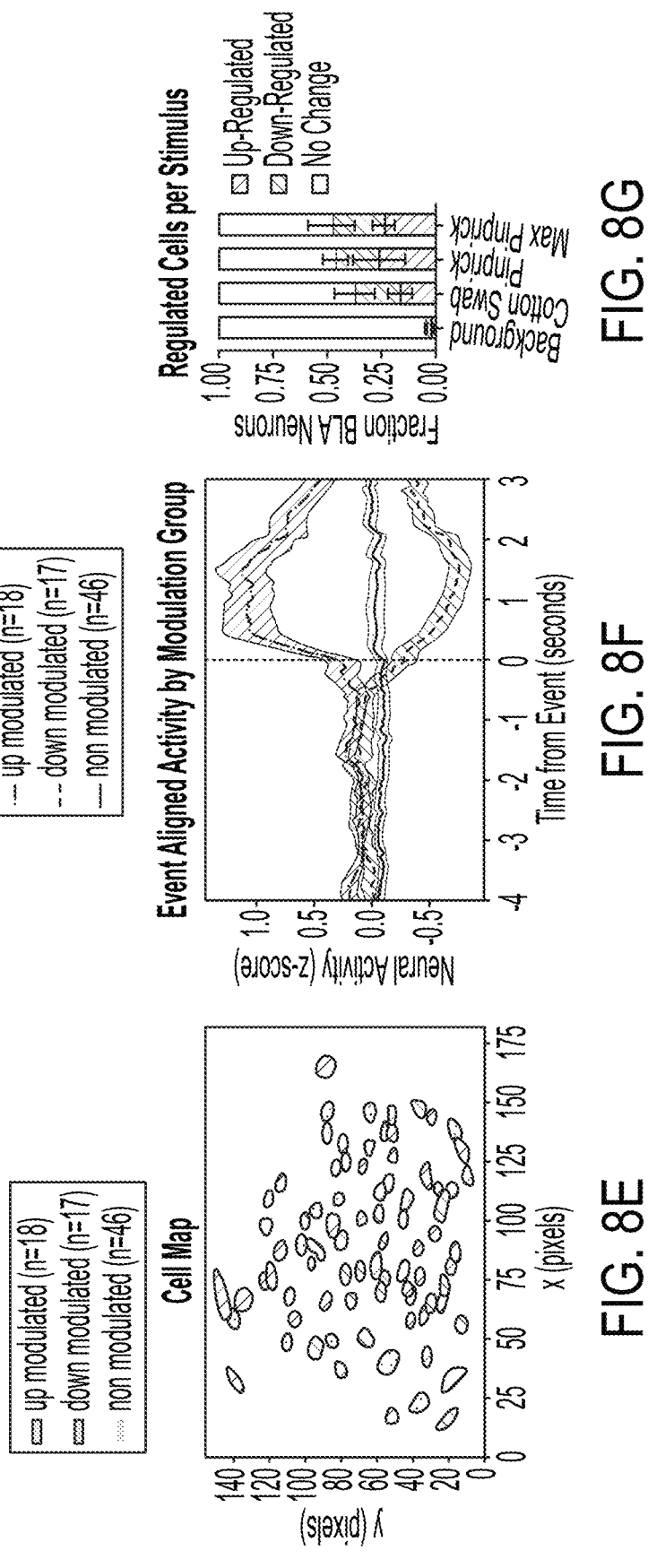
FIGS. 8E-8F depict example traces and cell map of pinprick stimulus aligned up and down-regulated cells based on peri-event analysis.
FIG. 8G depicts the results of peri-event analysis with up and down-regulated cells based on stimulus, and comparison with random background events.
Figures 8H, 8I, 8J:
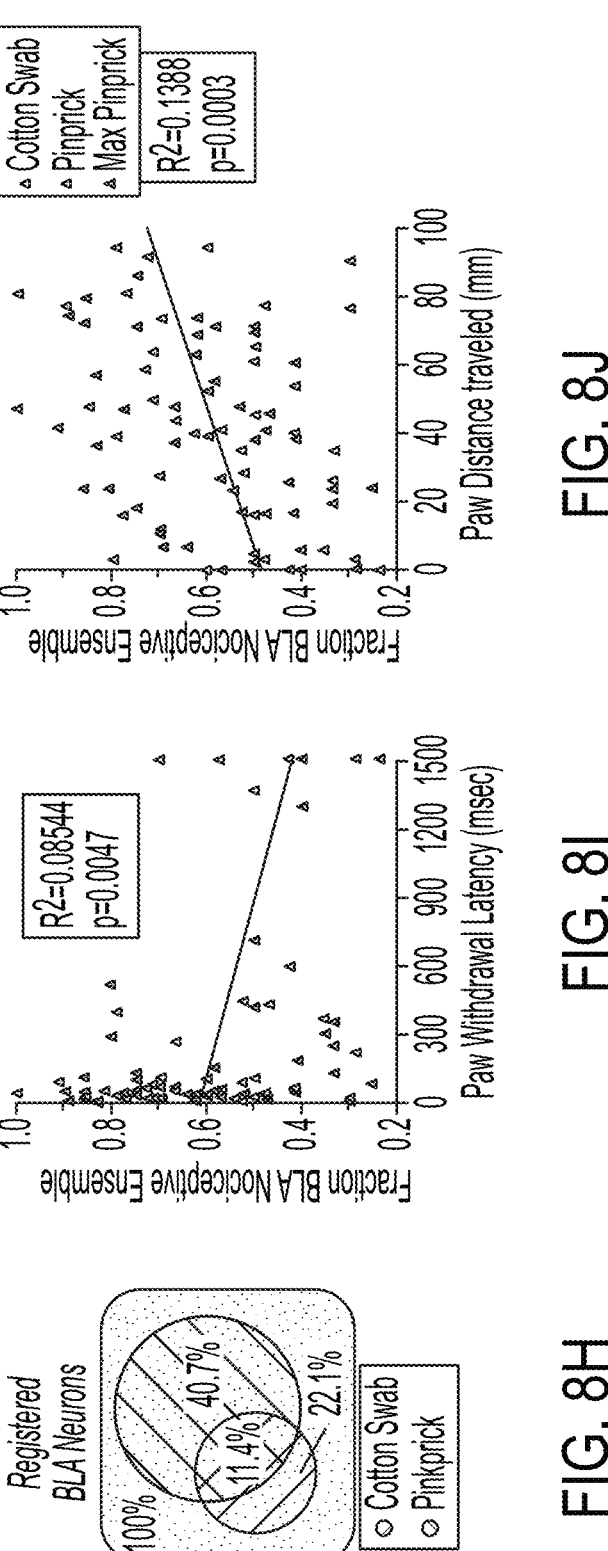
FIG. 8H depicts the percentage of cells registered across multiple days that are regulated during response to mechanical touch and/or pain stimuli.
FIG. 8I depicts the Pearson correlation between the fraction of total of peri-event analysis identified mechanical pain-regulated cells with matching regulation for each stimulus event with withdrawal latency.
FIG. 8J depicts the distance traveled in the 1.5 seconds post-stimulus application.

FIGS. 8A-J depict how ARM stimulation is linked with behavior and cellular-resolved brain activity in the basolateral amygdala (BLA). More specifically, FIG. 8A depicts a schematic showing alignment of BLA neural activity recorded by a microendoscope, PAWS behavioral features, and stimulus facilitated by the ARM. FIG. 8B depicts the confirmation of injection of jGCaMP8f virus and insertion of Inscopix mini-scope to the BLA. FIGS. 8C-D depict the cell map from processed mini-scope recording with a selection of representative deconvolved cell traces in pseudocolors over a 1000 sec window. FIGS. 8E-F depict example traces and cell map of pinprick stimulus aligned up and down-regulated cells based on peri-event analysis. FIG. 8G depicts the results of peri-event analysis with up and down-regulated cells based on stimulus, and comparison with random background events. Total regulated cells increased compared to background control for all stimuli (p<0.0001). FIG. 8H depicts the percentage of cells registered across multiple days that are regulated during response to mechanical touch and/or pain stimuli. FIG. 8I depicts the Pearson correlation between the fraction of total of peri-event analysis identified mechanical pain-regulated cells with matching regulation for each stimulus event with withdrawal latency FIG. 8J depicts the distance traveled in the 1.5 seconds post-stimulus application.

Analysis of the resulting withdrawal responses in male mice using PAWS and linear regression found both features with significant positive linear relationships with stimulus intensity and features where no significant correlation could be found. Reflexive features including paw withdrawal latency (FIG. 7B) and max paw height (FIG. 7C) showed significant correlations with stimulus intensity that explained 26.9% and 13.8% of the variation in the data respectively. In contrast, analysis of affective features including paw shaking duration (FIG. 7D) and paw distance traveled (FIG. 7E) found either no significant correlation or a correlation that only explained 6.596% of the variation in the data. This data indicates that in isolation, stimulus variability has a greater effect on the mouse's initial reflexive response than the following affective features.

Figures 13A, 13B:
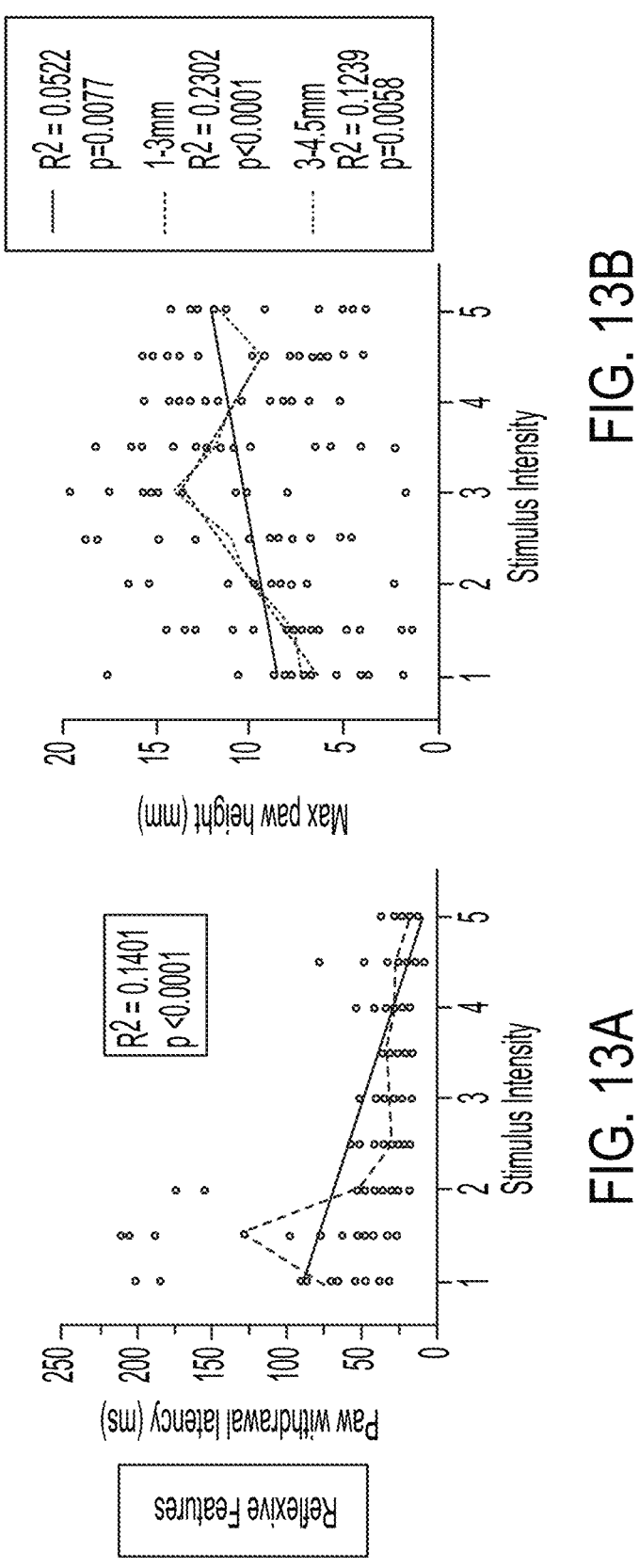
FIG. 13A depicts that a simple linear regression withdrawal latency negatively correlates with stimulus intensity.
FIG. 13B depicts a piecewise linear regression analysis that found that max paw height positively correlates with stimulus intensity.
Figures 13C, 13D:
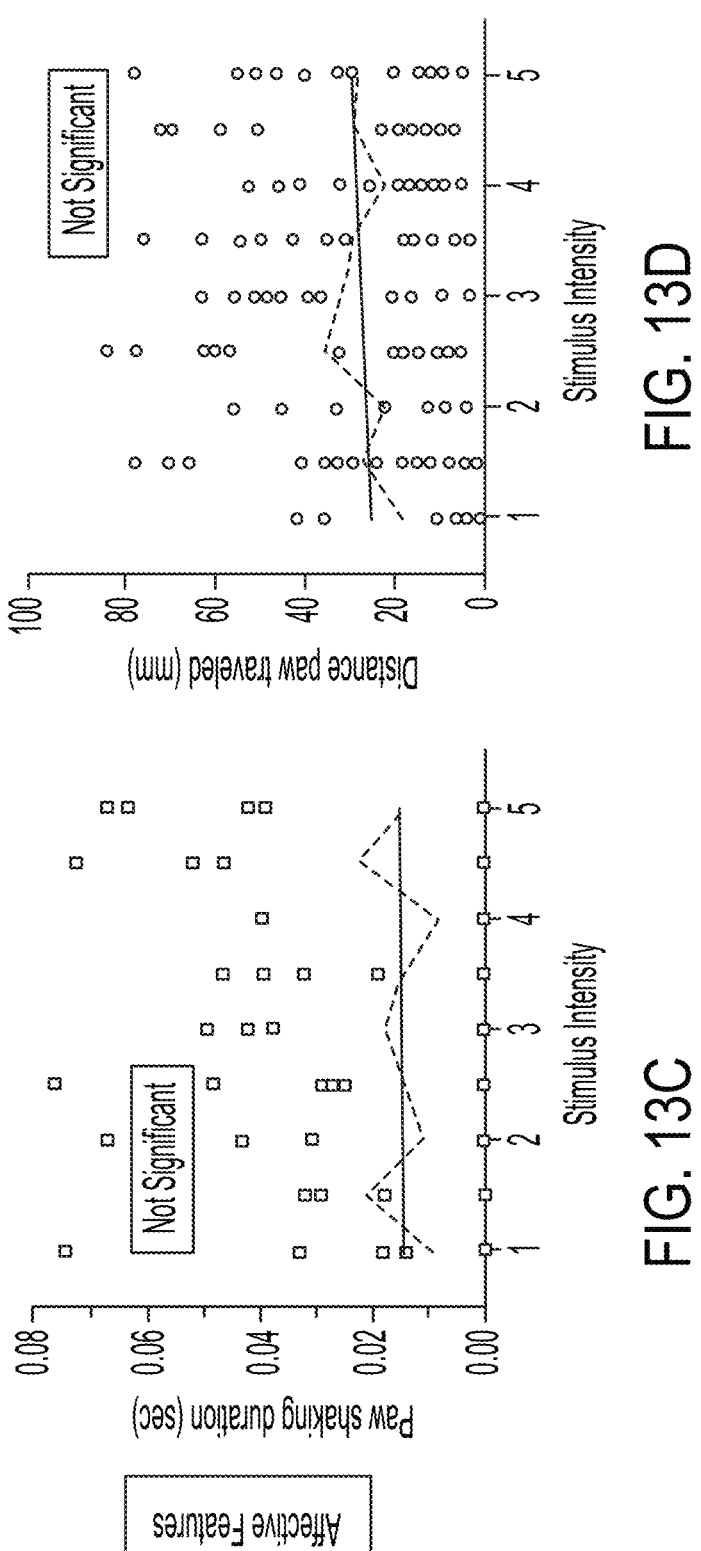
FIGS. 13C-13D show that for affective features, paw shaking time and paw distance traveled showed no significant correlation with stimulus intensity.

A second cohort of female mice was tested to confirm these results (n=15). Reflexive features were again shown to significantly correlate with stimulus intensity explaining 14.01% of the variability in withdrawal latency (FIG. 13A) based on linear regression. Stimulus intensity significantly correlated with max paw height but only explained 5.22% of the variability based on a simple linear regression. Pair-wise analysis however, found that a simple linear regression explained 23.02% of the variation in the data from 1-3 mm with a positive correlation with stimulus intensity and 12.39% from 3-4.5 mm with a negative correlation with stimulus intensity (FIG. 13B). This may indicate that increasing stimulus intensity at baseline can run into a ceiling effect in terms of its effect on behavioral features. Whether female mice exhibiting this effect but not male mice, is due to differences in sex or environmental confounders, is unclear. Analysis of affective pain behavior found no significant correlations between shaking time (FIG. 13C), or paw distance traveled (FIG. 13D).

In summary, variability in stimulus intensity in isolation contributes significantly to the resulting paw withdrawal response, though it appears to primarily affect the initial reflexive response. This is consistent with earlier data, where variation in von Frey delivery time appeared to correlate positively with withdrawal % (FIG. 4). It should be noted that withdrawal percentage, withdrawal latency, and withdrawal threshold are the most commonly used measures of mechanical sensitivity/pain and are based on the reflexive behavioral response that is significantly correlated with stimulus variability.

Syncing of stimulus with video and in vivo brain imaging data is possible.

We were interested in testing the performance of the ARM and PAWS analysis of neural activity in a brain region linked to pain. Moreover, we wanted a simultaneous readout of pain behavior with brain activity to confirm that the brain is indeed tracking mechanical stimuli at sub-second resolution. The basal lateral amygdala (BLA) was chosen based on previous work that has identified neural populations linked to defensive coping behaviors like paw attending, paw guarding, and paw shaking (Corder 2019, Jones 2020). This has included both the identification of excitatory neural populations that when activated lead to increased (Becker 2023, Han 2010) or decreased (Cai 2018) pain behavior. Adjustments were made to the ARM's arduino component to sync the ARM's stimulus delivery with both the high-speed camera and Inscopix platform for cellular-resolved microendoscopy. This allowed for the alignment of stimulus behavior and neural data (FIG. 8A). Mice injected with AAV9-syn-jGCaMP8f-WPRE virus (jGCaMP8f) targeting the BLA were stimulated with cotton swab and pinprick stimuli. Pinprick stimuli were delivered in two manners, the normal stimuli used previously and a greater intensity stimulus with increased speed and apex referred to as max pinprick. This was done to facilitate a greater range of responses. Each stimulus was delivered 15 times across 6 days for a total of 45 events per mouse (n=2).

BLA video data was processed using the IDEAS platform to correct for motion, identify neurons, and measure $\Delta F/F^\circ$ (FIG. 8C-D). Peri-event analysis was used to determine the mean change in cell $\Delta F/F^\circ$ across the total population (FIG. 14A-B) and identify neurons either significantly upregulated or downregulated resulting from either ARM stimulus events (FIG. 8E-F). Random time points chosen throughout the testing period were used for a comparison background group (FIG. 8E). Each of the three stimulus types led to significantly up/down-regulation of neural activity compared to background (FIG. 8G). This is consistent with previous work that has identified both neural populations up and downregulated during pain in the BLA (Becker 2023, Han 2010). Neurons were registered across consecutive days to identify neurons regulated by mechanical pain (29.3%), touch (10.7%), or both (11.4%) mechanical stimuli (FIG. 8H).

To determine whether BLA pain neuron regulation correlates with sub-second withdrawal behavioral features we then analyzed individual touch and pain stimulus events. Cells previously identified by the peri-event analysis as up or down regulated during mechanical pain were analyzed for each individual event using the Wilcoxon rank-sum analysis to determine the proportion of pain-regulated cells that showed associated up or down-regulation. Cotton swab events showed a significantly smaller proportion of pain matching downregulation, upregulation, or combined group regulation compared to the pinprick stimuli (FIG. 14C). No significant difference was found between pinprick and max pinprick behavior features or pain cell regulation. This may result from a similar ceiling effect to that seen in female mice in the pinprick variation experiments (FIG. 13B). For each event paw withdrawal latency, max height, max Y-velocity, and distance traveled in the 1.5 seconds following the stimulus were measured using PAWS. These metrics were then plotted against the proportion of up-regulated, downregulated, and total BLA mechanical pain-regulated neurons.

Our results on withdrawal latency were consistent with previous work (Corder 2019) that found that BLA mechanical pain neural activity correlates with this metric, with down-regulated (p=0.0032) and total mechanical pain neuron (p=0.0047) proportions correlating with withdrawal latency based on a Pearson correlation, total cell proportion explaining 8.544% of the variation in the data (FIG. 8I). In comparison paw distance traveled (FIG. 8J), and max Y velocity (FIG. 14E) each show correlations with up (p=0.0014, p=0.0324) down (p=0.0062, p=0.0009), and total (p=0.0003, p=0.0007) regulated mechanical pain cells respectively. Each explained a greater proportion of variability in the data than withdrawal latency with paw distance traveled explaining 13.88% and max Y Velocity explaining 12.11%. Max paw height showed the least correlation with BLA mechanical pain neural activity, showing only correlations with down (p=0.0459) and total (p=0.0426) neural activity, the latter explaining only 4.491% of the variability in the data (FIG. 14D). These findings suggest that Max Y velocity and paw distance traveled may be more useful metrics for the study of the BLA's role in pain compared to max paw height or the traditionally used withdrawal latency.

These findings may be consistent in other brain regions with neural populations linked to pain but are a matter for future study.

Discussion of the FIG. 3 embodiment.

The FIG. 3 ARM decreased variability in the application of traditional vFH filaments while decreasing the time needed per experiment and eliminating significant variation that was observed between researchers. Using the PAWS pain assessment software, we isolated the effects of experimenter presence and stimulus variability on multiple measures of pain behavior, including paw withdrawal latency. Experimenter presence significantly affected both reflexive and affective measures of paw withdrawal response, leading to the appearance of sex-dependent differences that did not appear when no researcher was present. In contrast, stimulus delivery variability had a greater effect on reflexive measures of the paw withdrawal response compared to affective measures. Finally, we used the ARM with an Inscopix setup to sync and correlate stimulus, basolateral amygdala (BLA) neural activity, and PAWS-measured behavioral features. We identified pain-regulated BLA neurons that were regulated by painful stimuli, and were able to correlate their activity with behavioral features of paw withdrawal to mechanical stimuli.

Previous attempts at automating mechanical stimulus delivery, including the electronic von Frey (Martinov 2013) and dynamic plantar asthesiometer (Nirogi 2012), have focused on eliminating variability in stimulus delivery. In contrast to the ARM, both of these devices rely upon a researcher being present to aim or deliver the stimulus, can only deliver vFH-like touch stimuli, and only measure withdrawal latency/force threshold. Additionally, progress has been made in automating stimulus assays by creating devices with the goal of delivering precise optogenetic and thermal stimuli to the mouse's hind paw (Dedek 2023, Schorscher-Petchu 2021). A limitation of these devices and those previously discussed is the lack of customization for delivering distinct modalities of mechanosensation and other somatosensory stimuli. Moreover, in its current form the automated aiming of some of these devices may not provide the same resolution or reliability of the ARM in targeting defined targets (FIG. 3C), such as regions of the mouse paw that might be sensitized during chronic pain states.

The ARM was designed to mimic the flexibility of manual delivery, capable of delivering poke (pinprick, vFH, cotton swab), static or dynamic brush, and optogenetic stimuli. For many of these stimulus combinations, the researcher does not need to even enter the room to switch between them. In comparison to manual stimulus delivery or delivery that requires a researcher to be present, the ARM is significantly faster. In addition to taking 50% less time to deliver the same vFH test as a researcher doing so manually, it was found that when experiments were being performed remotely using the ARM, without a researcher present, less time appears to be needed for mice to reach a resting state or reduce turning behavior. This could indicate that remote experiments could reduce habituation requirements for experiments. Finally, the ARM can be operated using infra-red cameras, opening up the possibility of experiments during the mouse dark cycle, which might be more ethologically relevant to study, given as a nocturnal animal it is their peak time of activity.

Mechanical delivery of stimuli to the rodent hind paw by an experimenter and measurement of the resulting paw withdrawal frequency, force threshold, or latency has been a gold standard for measuring nociception and pain for decades (Dixon 1980, Deuis 2017). In this paradigm, the experimenter both delivers the stimulus and scores in real time whether the paw moved after stimulation. This assay requires experimenter dexterity and focus, and thus a well-trained researcher. Moreover, because the experimenter performs these assays in real-time (stimulus delivery and paw withdrawal measurement), the sub-second speed of the paw withdrawal precludes a thorough description of all the behaviors that occur to a given stimulus. To add behavioral readouts to these rapid paw withdrawals that can aid in pain assessment, we use a pipeline consisting of high-speed videography, automated paw tracking, and custom software to map pain behavioral features (PAWS) (Jones 2020, Bohic 2023, Upadhyay 2024). We have demonstrated that we can detect acute mechanical pain, inflammatory pain, osteoarthritis pain, and neuropathic pain with this pipeline (Jones 2020, Bohic 2023, Upadhyay 2024). Here, we have updated this approach to make it more user-friendly, lower the financial barrier to entry with cheaper lower frame cameras, and add more readouts to aid in separating out pain states. Moreover, this pain assessment pipeline is fully integrated with the ARM stimulus delivery, which should increase throughput and robustness in performing short-term and longitudinal nociceptive assays. Lastly, although we use a pain assessment pipeline of high-speed videography with automated measures of pain behaviors, the ARM can be used with traditional measurements of pain assessment such as paw withdrawal frequency, latency to withdrawal, or mechanical withdrawal threshold.

Finally, we combine ARM stimulation with in vivo brain recording in the basolateral amygdala, an area that has been linked to encoding pain affect, unpleasantness, and negative emotion (Corder 2019, Meng 2022, Becker 2023, Tanimoto 2003). Although we focus on the amygdala as a proof-of-principle in this study, future studies could use this setup to combine ARM stimulation with behavior mapping and brain recordings in other cortical and sub-cortical areas implicated in pain (Meda, 2019, Chiang 2020, Tan 2021, Singh 2020, Okada 2021, Zhou & Li 2023, Li & Yang 2024, Chen & Sun 2023). Historically, pain neuroscientists have focused much attention on the peripheral nervous system-the site of nociceptive transduction. The field has made great progress with this focus and therapeutic development has revolved nearly chiefly at blocking pain at its root within the sensory ganglia. With this said, there is an abundance of evidence in both humans and rodents demonstrating the importance of defined circuits in the brain that help to localize the pain, determine pain intensity, and encode the negative emotional states that occur during pain (François 2017, Meda 2019, Corder 2019, Lee 2021, Kruner 2021, Kragel 2018, Apkarian 2005, Tracey 2000).

The ARM embodiments described in this application democratizes the study of pain by the removing the need to have a well-trained researcher spending hours aiming at the rodent paw. This opens the field up to the vast array of scientists who perform in vivo brain recordings to investigate sensory states. Moreover, researchers outside the field who study other questions like autism, neurodegeneration, or social isolation for example, which all have reported somatosensory deficits (Orefice 2016, O'Leary 2018, Crane 2009, Hu 2023, Horiguchi 2013)—might have an easier time phenotyping their animals with the ARM. It can also not be ignored that traditional somatosensory assays are physically taxing and are not options for some researchers with physical disabilities; challenges the ARM in many ways overcomes. Opening the pain and somatosensory field up to more scientists should accelerate the pace of discovery.

It will therefore be apparent that the FIG. 3 embodiment can deliver a variety of mechanical stimuli, even remotely, at above expert level. We envision the ARM being used across academia and industry to uncover new mechanisms of pain neurobiology and for high-throughput screening of novel analgesics.

Supplementary data for the FIG. 3 embodiment is provided in FIGS. 9-14, which are described immediately below.

Figures 9A, 9B:
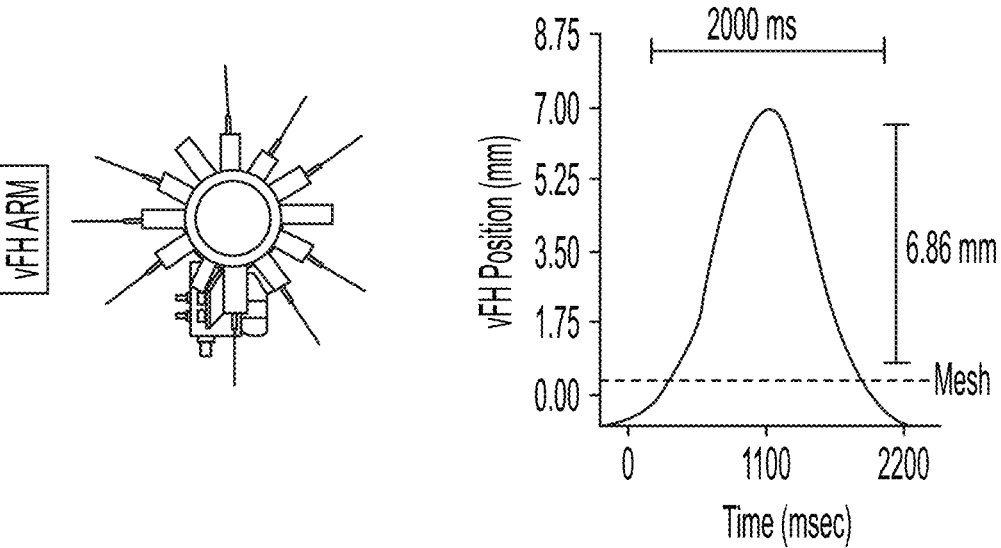
FIG. 9A is a schematic showing vFH wheel mounted on the ARM allowing for seamless switching between full range of vFH filaments and sin wave movement of ARM.
FIG. 9B depicts ARM-based application of cotton swab and pinprick stimuli via sin wave motion mimicking manual delivery.
Figure 9C:
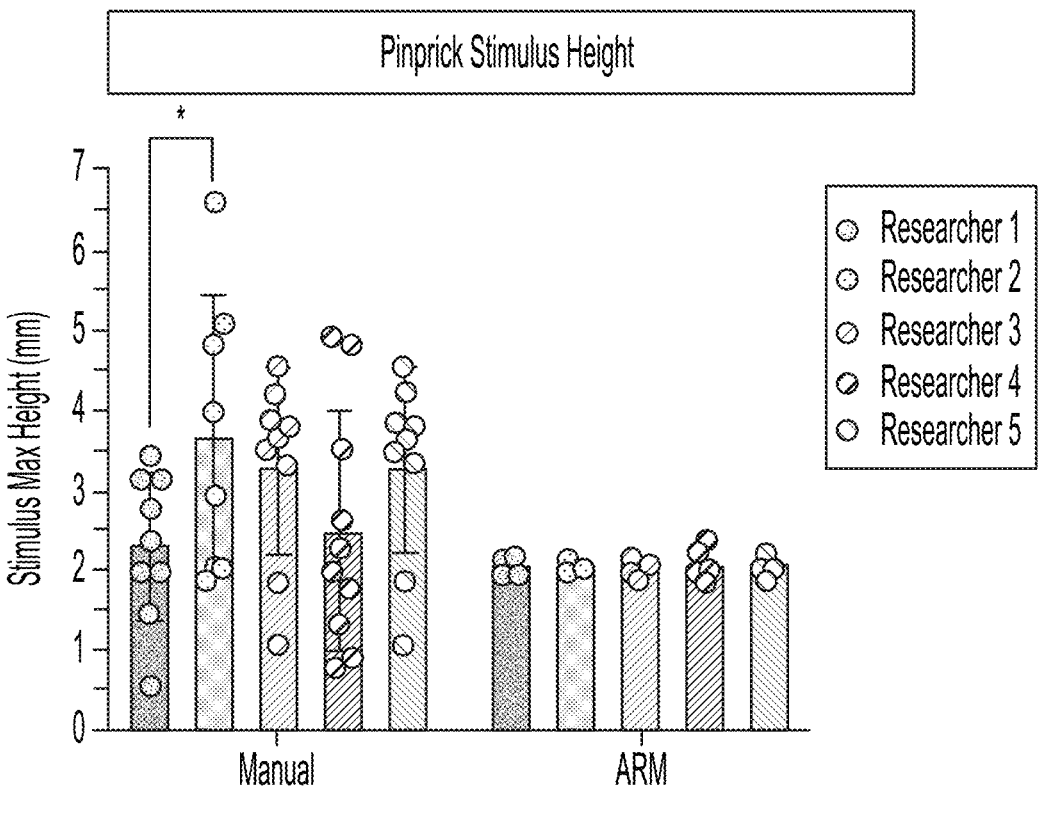
FIG. 9C is a comparison of pinprick stimuli delivered manually and via the ARM.

FIGS. 9A-C depict a comparison between stimulus delivery using the FIG. 3 embodiment and manual stimulus delivery. More specifically, FIG. 9A is a schematic showing vFH wheel mounted on the ARM allowing for seamless switching between full range of vFH filaments and sin wave movement of ARM allowing for full application vFH max force for 2 sec. FIG. 9B depicts ARM-based application of cotton swab and pinprick stimuli via sin wave motion mimicking manual delivery. And FIG. 9C is a comparison of pinprick stimuli delivered manually and via the ARM, based on max stimulus height measured via high-speed video recordings. Error rate of +/−0.152 mm based on resolution.

FIGS. 10A-B compare cross-researcher vFH behavior between the FIG. 3 embodiment and manual delivery. More specifically, FIG. 10A is a comparison between paw withdrawal frequency elicited by Researcher 1 versus Researcher 2 with 2-way Anova. Significant differences were found in behavior elicited by 0.6 g (p=0.0034), 1 g (p=0.0462), and overall (p=0.0008). And FIG. 10B depicts data when two researchers applied ARM vFH stimulus remotely over two days. 2-way Anova detected no significant differences.

Figure 11A:
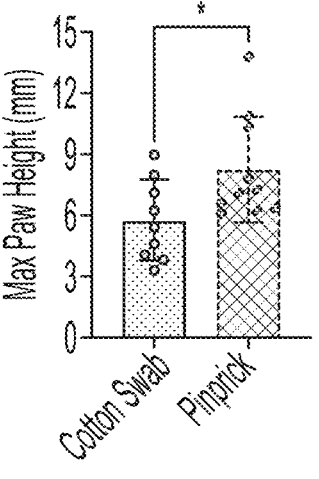
FIG. 11A depicts a cohort of male mice tested with cotton swab and pinprick stimuli.
Figure 11B:
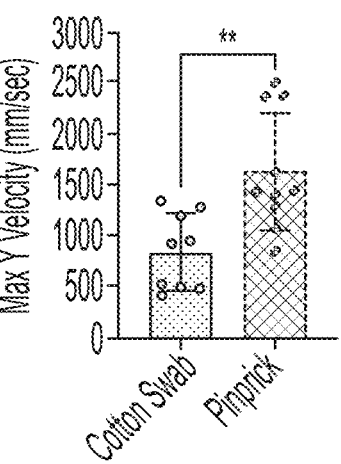
FIG. 11B and 11C depicts the max Y velocity and the paw distance traveled, respectively.
Figure 11C:
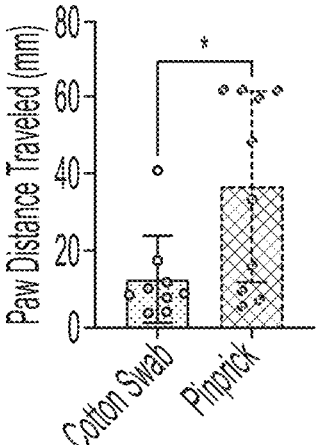
Figure 11D:
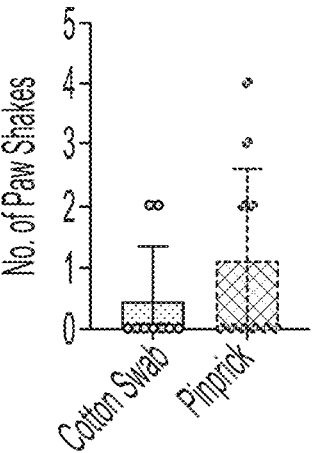
FIG. 11D shows that the number of paw shakes was higher for pinprick stimuli.

FIGS. 11A-D depict a test of 500 fps PAWS analysis. More specifically, FIG. 11A depicts a cohort of male mice (n=10) tested with cotton swab and pinprick stimuli. Pinprick was found to elicit significantly increased max paw height (p=0.0163). FIG. 11B depicts the max Y velocity (p=0.0034), and FIG. 11C depicts the paw distance traveled (p=0.0172) by a paired t-test. FIG. 11D shows that the number of paw shakes was higher for pinprick stimuli but was not found to be significant.

Figure 12A:
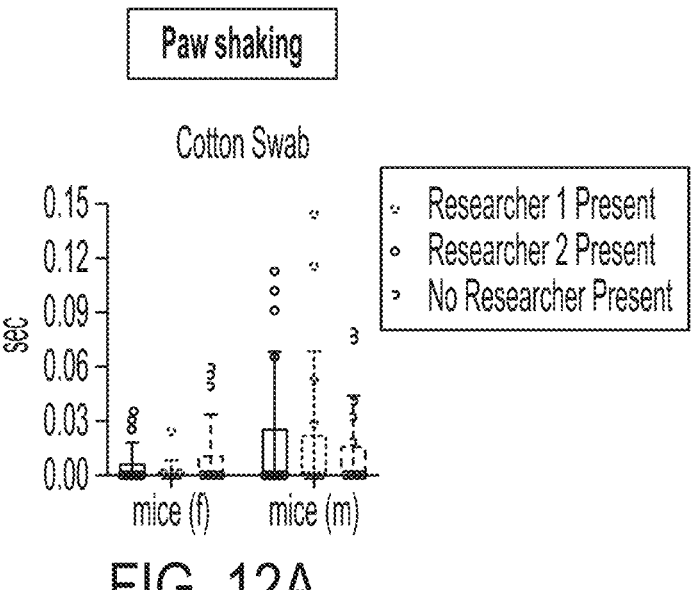
FIGS. 12A-12B depict a remote experiment comparing mouse response when one of two researchers is present vs none.
Figure 12B:
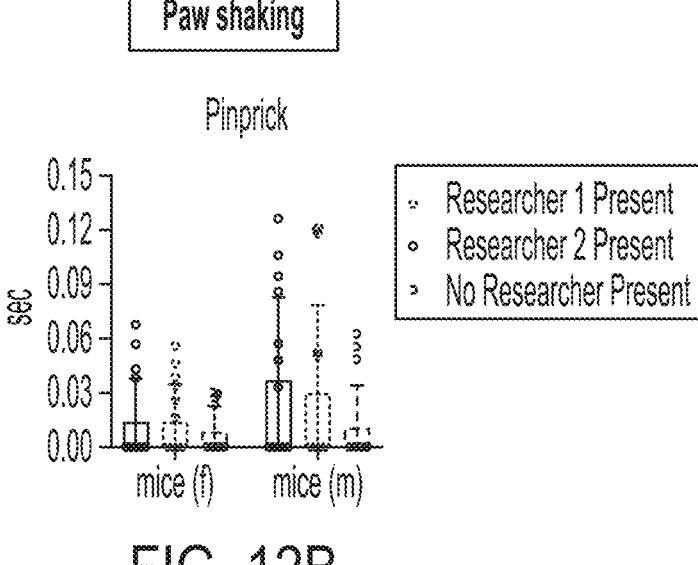

FIGS. 12A-B show that shaking duration did not change significantly based on experimenter presence. More specifically, FIGS. 12A-B depict a remote experiment comparing mouse response when one of two researchers is present vs none. Non significant sex-dependent differences were found in response to cotton swab (p=0.0613) and pinprick (p=0.0551) when Researcher 1 was present for paw shaking duration.

FIGS. 13A-D depict isolating the effect of variation in applying pinprick stimulus in female mice. More specifically, FIG. 13A is based on a simple linear regression withdrawal latency negatively correlates with stimulus intensity. FIG. 13B is a piecewise linear regression analysis found that max paw height positively correlates with stimulus intensity for stim apex 1-3 mm and negatively correlates for 3-4.5. FIGS. 13C-D show that for affective features, paw shaking time and paw distance traveled showed no significant correlation with stimulus intensity.

Figure 14A:
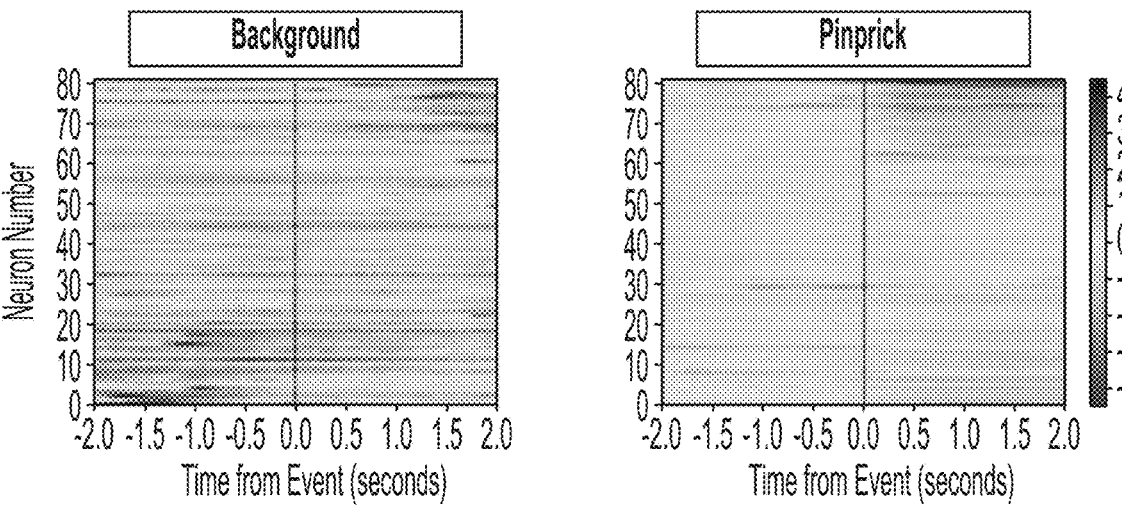
FIG. 14A depicts an example of cell activity heat map and mean cell trace results of peri-event analysis of representative traces.
Figure 14B:
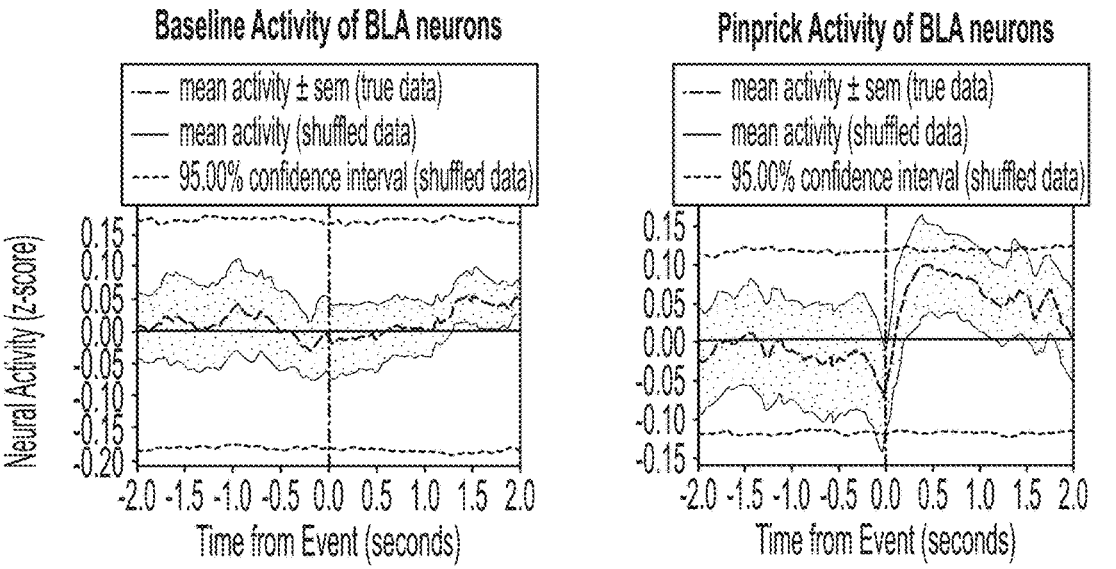
FIG. 14B depicts an example of mean cell trace results of peri-event analysis of representative traces.
Figure 14C:
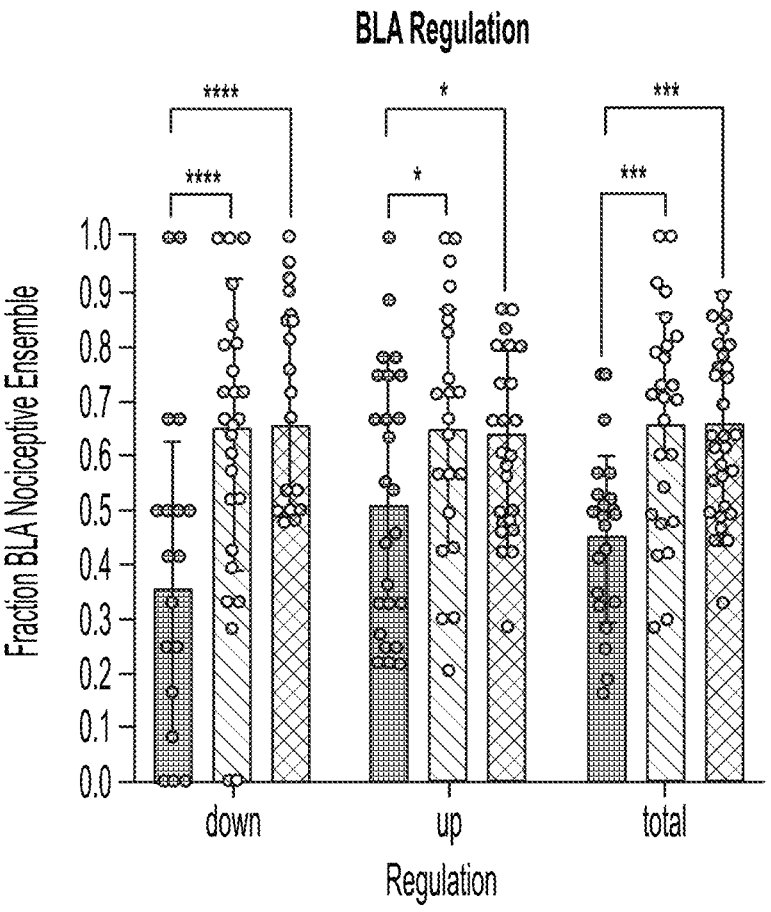
FIG. 14C depicts the fraction of peri-event analysis identified mechanical pain-regulated cells with matching regulation for each stimulus event.
Figure 14E:
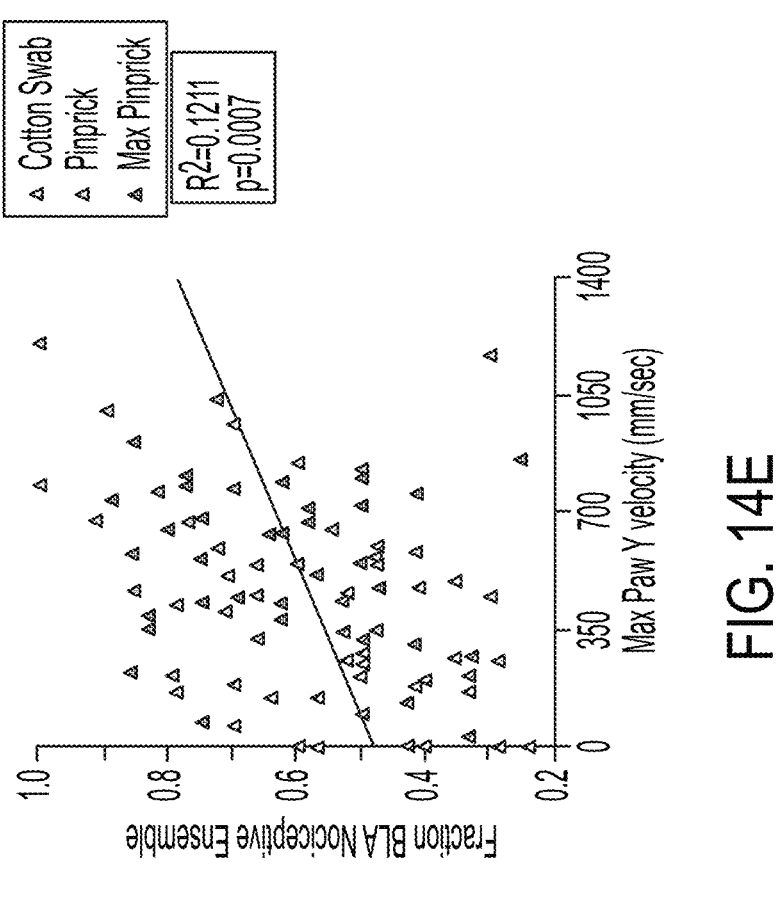
FIG. 14E shows the max paw Y velocity.
Figure 14D:
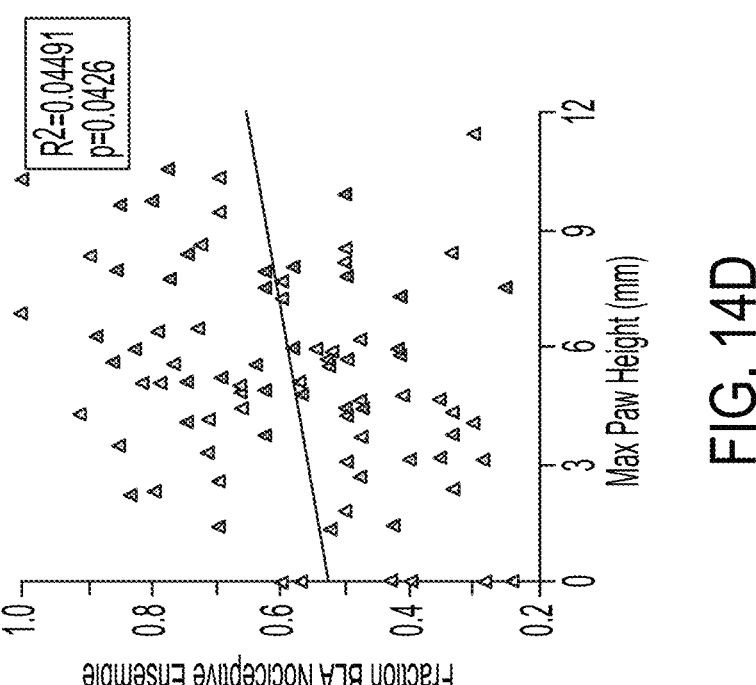
FIG. 14D shows the Pearson correlation between the fraction of total regulation of identified mechanical pain cells and paw max height.

FIGS. 14A-E depict the correlation of additional PAWS features with BLA mechanical pain neuron regulation. More specifically, FIG. 14A is an example of cell activity heat map and mean cell trace results of peri-event analysis of representative traces based on either 10 random background or pinprick events. FIG. 14B is an example of mean cell trace results of peri-event analysis of representative traces based on either 10 random background or pinprick events. FIG. 14C shows the fraction of peri-event analysis identified mechanical pain-regulated cells with matching regulation for each stimulus event. Cotton swab events showed decreased down ($p<0.0001$), up ($p<0.05$), and total ($p<0.0005$) regulation of identified mechanical pain cells compared to pinprick or max pinprick. FIG. 14D shows the Pearson correlation between the fraction of total regulation of identified mechanical pain cells and paw max height and FIG. 14E shows the max paw Y velocity.

Six videos depicting the operation of the FIG. 3 embodiment were recorded, and the contents of those videos is described below. One video depicted the remote operation of the ARM. Researcher aims the ARM using video feed and crosshairs, switches between stimuli, and delivers stimuli to a fake mouse in the behavior room from their lab bench. A second video depicted the ARM with automated habituation program activated, with empty chambers or chamber with a fake mouse for reference. The program lowers the stimulus holder so that stimulus delivery will not cross the mesh. The ARM then moves to the first chamber and randomly moves, pauses, or delivers a stimulus to empty air for 1 minute before moving on to the next chamber. This program habituates mice to the presence and noise of the ARM. Note that the ARM is quiet enough to barely be heard over the background noise of the HVAC.

A third video depicted a representative example of SLEAP tracked 2000 fps cotton swab trial, with manual stimulus delivery. Stimulus is delivered at an angle and lingers at apex. Mouse slowly removes paw from the stimulus and places it back on the mesh. A fourth video depicted a representative example of SLEAP tracked 2000 fps cotton swab trial, with ARM stimulus delivery. Stimulus is delivered straight up and down, withdrawing quickly after reaching its apex. The mouse slowly removes paw from the stimulus and places it back on the mesh.

A fifth video depicted a representative example of SLEAP tracked 2000 fps pinprick trial, with manual stimulus delivery. Stimulus is delivered at an angle, almost hitting the mouse's paw a second time. Mouse gives a robust response including guarding behavior. A sixth video depicted a representative example of SLEAP tracked 2000 fps pinprick trial, with ARM stimulus delivery. Stimulus is delivered straight up and down, withdrawing quickly after reaching its apex. Mouse gives a robust response including shaking and guarding behavior.

Methods

The methods described in this section were used in connection with the FIG. 3 embodiment to obtain the data described above in connection with FIGS. 4-14.

Mice: All experimental testing was performed in compliance with the Guide for the Care and Use of Laboratory Animals (NIH). All procedures were approved by the Institutional Animal Care and Use Committee of Columbia University. Unless stated otherwise all mice were co-housed with a max of 4 other mice in a large housing room with approximately 100 other mouse cages. C57BL/6J mice were ordered from Jackson Laboratories. Over the course of the experiments, male and female mice ranging from 8-16 weeks in age were used for testing. All groups compared were within a week in age of each other. The mice were kept on a day-night light-dark cycle and brought to a specialized behavior analysis room for testing. Mice were normally fed commercially available pelleted rodent chow and watered ad libitum.

Somatosensory Behavior Assays: During testing mice were placed in acrylic chambers (4.2 cm×11.5 cm×4.6 cm) on a specialized mesh table held down by acrylic weights in an isolated testing room separate from normal housing. A max of 5 mice were tested at any one time. Mice were allowed to acclimate to their housing for 2 weeks before testing. Before somatosensory testing mice were habituated for 4 days, 1 hour each, to testing conditions. A habituation program where the ARM moved randomly and gave stimulus to empty air was used to get the mice used to its noise. For experiments where only remote ARM work would be performed only 1 day of habituation was found to be needed. On the day of testing, mice were habituated to their chamber for 15 minutes before testing. During testing the ARM and high-speed camera moved between fixed starting positions for each chamber with z-axis at a default working height of 156.25 with the mesh 14 mm above stimulus. This movement, precise movement of the ARM, and stimulus delivery was performed using an Xbox one controller and custom Python code. The bottom aiming camera was calibrated either by poking a pinprick through a piece of tape, and moving its crosshairs to that point or using previously used coordinates. Once calibrated, the bottom camera was used to aim the stimulus at the center of the mouse paw, before delivering stimuli. Cotton swab and pinprick stimuli were delivered using a sin wave motion of the ARM's z-axis starting from the trough with amplitude of 8 mm and wavelength of 0.8 seconds. For von Frey Hair testing the z axis started at a working height of 145 mm with mesh 0.14 mm above stimulus and delivered stimulus using a sin wave motion of the ARM's z-axis with an amplitude of 3.5 mm and wavelength of 2.2 seconds. These values were chosen to model the average manual delivery of stimuli as seen in Jones 2020, while avoiding accidental stimulus delivery to body parts other than the paw, or double stimulus of the paw. The radial axis was used to switch between cotton swab, pinprick, and dynamic brush stimulus, it was also used to switch between vFH. Unless otherwise stated, mice were tested remotely with the researcher controlling the ARM from elsewhere in the lab. Stimulus delivery triggered camera recording with a delay calibrated to ensure recordings would start 25 msec before the stimulus went above the mesh to facilitate measurements of withdrawal latency.

For vFH experiments bioseb von Frey filaments were used either delivering stimulus in the canonical manner (Dixon 1980, Zhou 2018) or attached to a holder on the ARM and depressed against the mouse paw in the manner discussed. Testers or the ARM first delivered vFH stimulus (1.4 g, 2 g) to a force sensor with 0.05 gF resolution (Mark-10 Model M5-05 max 250 GF), before delivering vFH (0.02 g, 0.07 g, 0.16 g, 0.6 g, 1 g, 1.4 g) to mice ($n=10$ male). Each vFH was delivered 10 times consecutively to each mouse and withdrawal frequency was measured. For habituation experiments 2 groups of 10 male mice were either habituated with a researcher present or without. Mice were habituated 5 at a time for 3 days 40 minutes each day with timing and experimenters kept consistent. Mice were monitored remotely in 1-minute periods, with 4 minutes in between as other mice were monitored. Mice were monitored for number of 180° turns and whether they rested (not turning, grooming, or investigating) for the whole minute. For remote delivery experiments, 3 groups of 5 mice ($n=15$ male and female) were used with each group either having researcher 1, researcher 2, or no researcher present during experiments. This was repeated for 2 more days to ensure each group experienced each condition. For the stimulus variation experiments, 9 stimulus types were devised using standard pinprick stimulus as a basis and calculating new sin waves to vary pinprick apex from 1-5 mm in 0.5 mm steps while keeping the time the pinprick spent above the mesh consistent. Mice (n=15 male and female) were then delivered a random selection of these stimuli, 3 per day for 3 days, with none repeated so that each mouse would by the end receive all 9.

ARM targeting experiment: 5 researchers delivered pinprick stimuli to a target, 10 times manually and 10 times with the ARM. Stationary 0.5 mm diameter dots on printer paper were used as the target for these experiments. 20 targets were used per researcher, 10 for manual and 10 for ARM. Researchers were instructed to aim for the center of each dot and deliver stimulus poking through the paper. Calipers were then used to measure the distance from each hole or indentation to the center of the corresponding target.

Carrageenan inflammatory pain assay: Mice were first tested with cotton swab and pinprick stimuli by the ARM. Mice were then injected with 20 ul 3% 1-Carrageenan (Sigma-Aldrich) in 0.9% sterile NaCl solution (saline) was injected into the mouse hind paw. 4 h post-injection they were again tested with cotton swab and pinprick stimuli.

Analysis of Paw Withdrawal Behavior: We utilized Pain Assessment at Withdrawal Speeds (PAWS) as a comprehensive behavioral tool to assess the reflexive and affective components of the evoked paw withdrawal response as previously described (Jones 2020). The reflexive component describes the initial rapid paw withdrawal, putatively governed by the peripheral nervous system and spinal cord, while the affective component describes the rest of this response, putatively governed by the brain. PAWS distinguishes the reflexive from the affective portions of the response (designated as t*), which is the timepoint in the response at which the paw reaches its first local maximum in height. PAWS analyzes these components separately and extracts kinematic features such as maximum height, maximum x-velocity, maximum y-velocity, distance traveled in both the reflexive and affective domains. For this paper max paw height and max Y velocity was extracted from the reflexive domain and distance traveled was extracted from the affective domain. Within the affective metrics, PAWS additionally extracts number of shakes (defined as a rapid velocity inflection), total duration of shaking behavior, and total duration of guarding behavior (defined as elevation of the paw above a specified height).

We recorded evoked paw withdrawal responses to cotton swab, dynamic brush, and light and heavy pinprick mechanical stimuli using a high-speed video camera (Photron Fast-CAM Mini AX 50 170 K-M-32GB-Monochrome 170K with 32 GB memory) and attached lens (Zeiss 2/100M ZF.2-mount) or a lower fps camera (0.4 MP, 522 FPS, Sony IMX287 camera). Videos were recorded at 2000 or 500 frames per second (fps). These videos were saved directly to an external hard drive as .avi or .mp4 format on a Dell laptop with Photron FastCAM Analysis software installed.

We used SLEAP, a machine-learning framework for supervised behavioral tracking of the mouse hind paw (Pereira 2022). In training our models, we annotated the heel (labeled 'heel'), the metatarsophalangeal joint (labeled 'center'), and the toe (labeled 'toe'), as well as two reference points set to the top left and bottom left corner of the transparent acrylic chamber housing the mouse during stimulation (labeled 'objectA' and 'objectB,' respectively). The 'center' point was the default point used for analysis. These reference points were used to automatically scale each video from pixel distances to millimeter distances given a known distance between these points when loaded into PAWS. After training and running inference on unlabeled frames, we exported all tracking data as HDF5 files before PAWS analysis. The machine used to train the SLEAP model was running Windows 11 Pro, an NVIDIA Geforce RTX 3060 GPU, and an Intel Core i7-12700K CPU processor We utilized a custom script within PAWS to extract tracking and tracking confidence data from HDF5 files into CSVs. For PAWS analysis parameters, we used a built-in average rolling filter with a window, a size of _17 frames was our default for analysis. We used a p-cutoff threshold of 0.45, at which tracking values below 45% confidence would be replaced with linear interpolation, a shaking height threshold of 0.35 mm, a fixed baseline height of 1 mm, and a y threshold (defining paw lifts) of 0.5 mm. These values were varied when a tracked video could not be analyzed at the default settings. In the subset of videos where we calculated paw withdrawal latency, we fit a sinusoidal stimulus trajectory to the parameters used to deliver pinprick or cotton swab by the ARM. We then flexibly defined withdrawal latency as the point in time following stimulus application at which the tracking data for the body-part of interest (heel, metatarsophalangeal joint, or toc) is higher than the stimulus trajectory. Following batch processing of tracked videos, PAWS exports a single CSV spreadsheet containing these individual metrics. We updated PAWS to flexibly scale behavioral tracking data from cameras recorded at less than 2000 frames per second by defining a custom 'resize' function which expanded the data to its 2000 fps-equivalent size (for instance, 50 data points at collected over 0.1 second at 500 fps were expanded to 200 data points, equivalently collected over 0.1 second at 2000 fps), using linear interpolation to estimate the positions of the paw between each point. This resize function can also be utilized for recordings taken over 2000 fps, where instead of interpolation the trajectories were simply down sampled to 2000 fps. These adjusted trajectories were then processed through our PAWS pipeline.

Our PAWS pipeline is freely available for installation and use on GitHub (https://github.com/osimon81/PAWS). For ease of use, we have also developed a comprehensive tutorial with example tracking data, and function documentation available through GitHub Pages (https://osimon81.github.io/PAWS)

Stereotaxic Surgery: Eight-week old male C57BL/6J mice were injected with AAV9-syn-jGCaMP8f-WPRE virus (Addgene #162376-AAV9) (jGCaMP8f) and implanted with integrated 0.6 mm×7.3 mm lens with attached baseplates (Inscopix cat. #1050-004413) via stereotaxic surgery in a single-step procedure. Viruses were injected and lenses implanted at the following coordinates to target the BLA: (AP: −1.6 mm, ML: 3.2 mm, DV: −4.5 mm). All lenses were implanted on the right hemisphere, following the use of a 22 G guide needle to clear tissue for the lens down to DV: −4.4 mm. The integrated lenses with baseplates were secured to the skull with Metabond adhesive cement (C&B #S380). Mice were treated with meloxicam for 3d post-surgery, and the virus was allowed to express for four weeks before imaging.

Microendoscope Imaging: Mice were habituated with the dummy miscroendoscope on the ARM platform for 1 hour the day before the experiment. On each experimental day, mice were scruffed and attached to the mini-epifluorescence microscope via the head-mount cemented onto the skull during surgery. Mice were then habituated on the ARM platform for 5 minutes, and then 10 minutes of baseline brain activity was recorded. After baseline was taken, the mouse's left hind paw was given a stimulus every two minutes until ten successful stimulations had been delivered or until 50 minutes of total recording time had elapsed. On days one, two, and three of the experiment, mice were stimulated with cotton swab, dynamic brush, and a light pin prick, respectively. Only one type of stimulus was given per day and no day of recording exceeded 50 minutes. Calcium imaging data was collected using the Inscopix n Vista system (Inscopix Data Acquisition Software (IDAS Version 1.3.0)). Recordings were taken under the conditions: frame rate=20-25 Hz, LED power=0.5 mW/mm$^2$, and a gain and focus that optimized image resolution and GCaMP expression for each mouse. A general-purpose input/output (GPIO) was configured such that triggering the ARM placed an annotation in the Inscopix output. Videos were automatically spatially downsampled by 4 by the data acquisition software, as recommended by the manufacturer.

Microendoscope Imaging Fluorescence Analysis: Video and annotation files generated during data collection by the Inscopix Data Acquisition Software were uploaded and processed in the Inscopix Data Exploration, Analysis, and Sharing (IDEAS) platform. Videos were motion-corrected with the . . . and normalized with (each function). Image segmentation and cell detection was performed with the (which pipeline). The Peri-Event Analysis Workflow (Version 2.4.3) was used to define events.

Imaging Statistics and Data Analysis: Microendoscope data was analyzed using the Inscopix Data Exploration, Analysis, and Sharing (IDEAS) platform for motion correction, application of a spatial bandpass filter and a constrained non-negative matrix factorization. The resulting cells were then manually accepted or rejected and registered using Inscopix data processing. A peri-event analysis was performed using IDEAS for each recording based on either Inscopix GPIO data from ARM stimulus events or random timestamps used to represent background fluctuation. The statistical windows were −2 to 0 and 0 to 2. Cells with significant regulation during pinprick or max pinprick events and matching registered cells were identified as BLA mechanical pain neurons, which were then analyzed on an individual event basis. A window −4 to −2 seconds before each event was used to calculate zscores weights, and then zscores from the −4 to −2 window and 0 to 2 window were compared using a Wilcoxin rank-sum test to determine whether significant up regulation or down regulation occurred. Fractions of up-regulation and down-regulation that matched average mechanical pinprick regulation determined by the peri-event analysis were determined for each event and correlated with max paw height, max Y velocity, withdrawal latency, and distance traveled as measured by PAWS using a simple linear regression and pearson correlation.

Example 3

Figure 15:
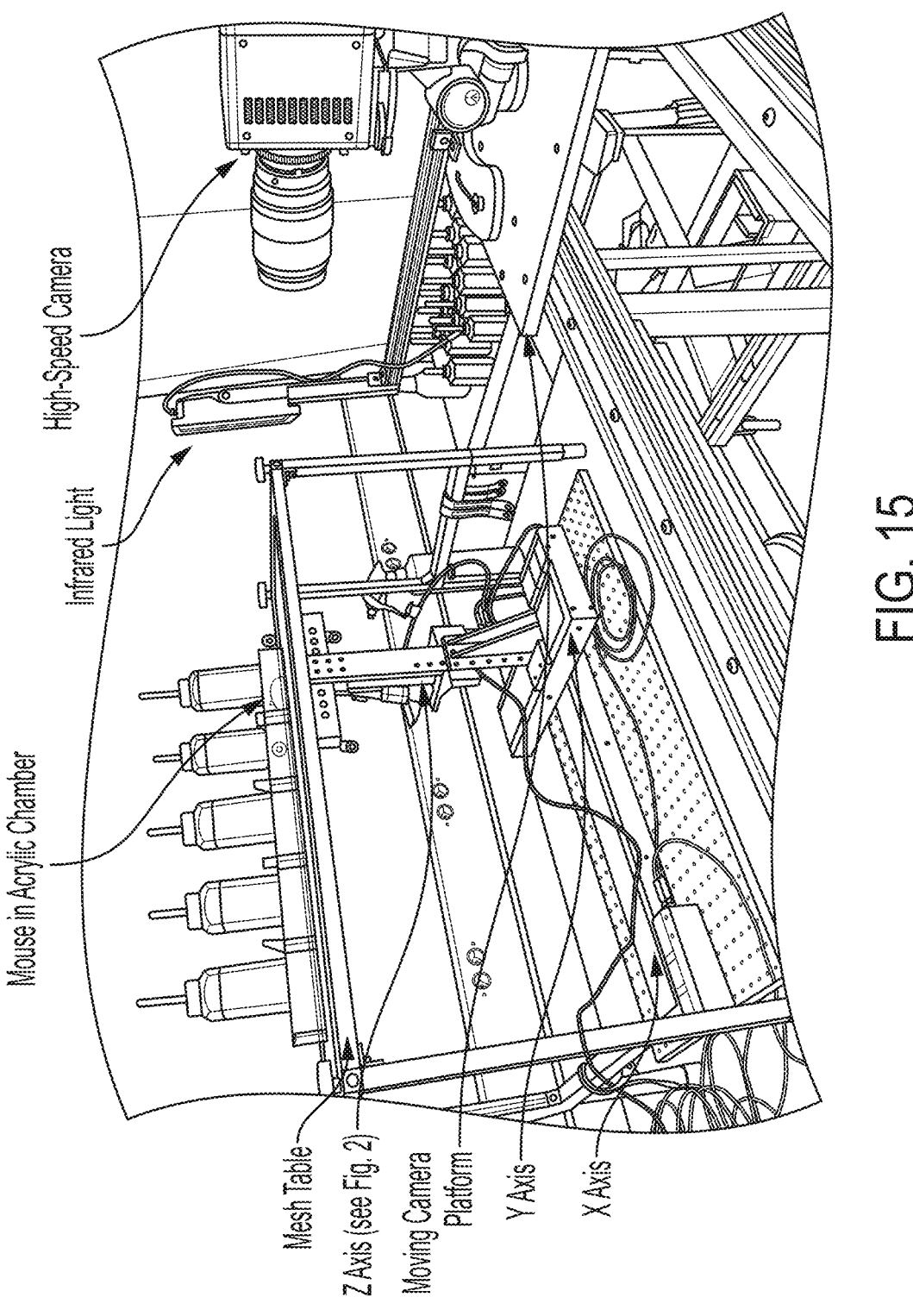
FIG. 15 depicts a third ARM embodiment that reduces stimulus variability and allows for remote delivery of the stimuli.
Figure 16:
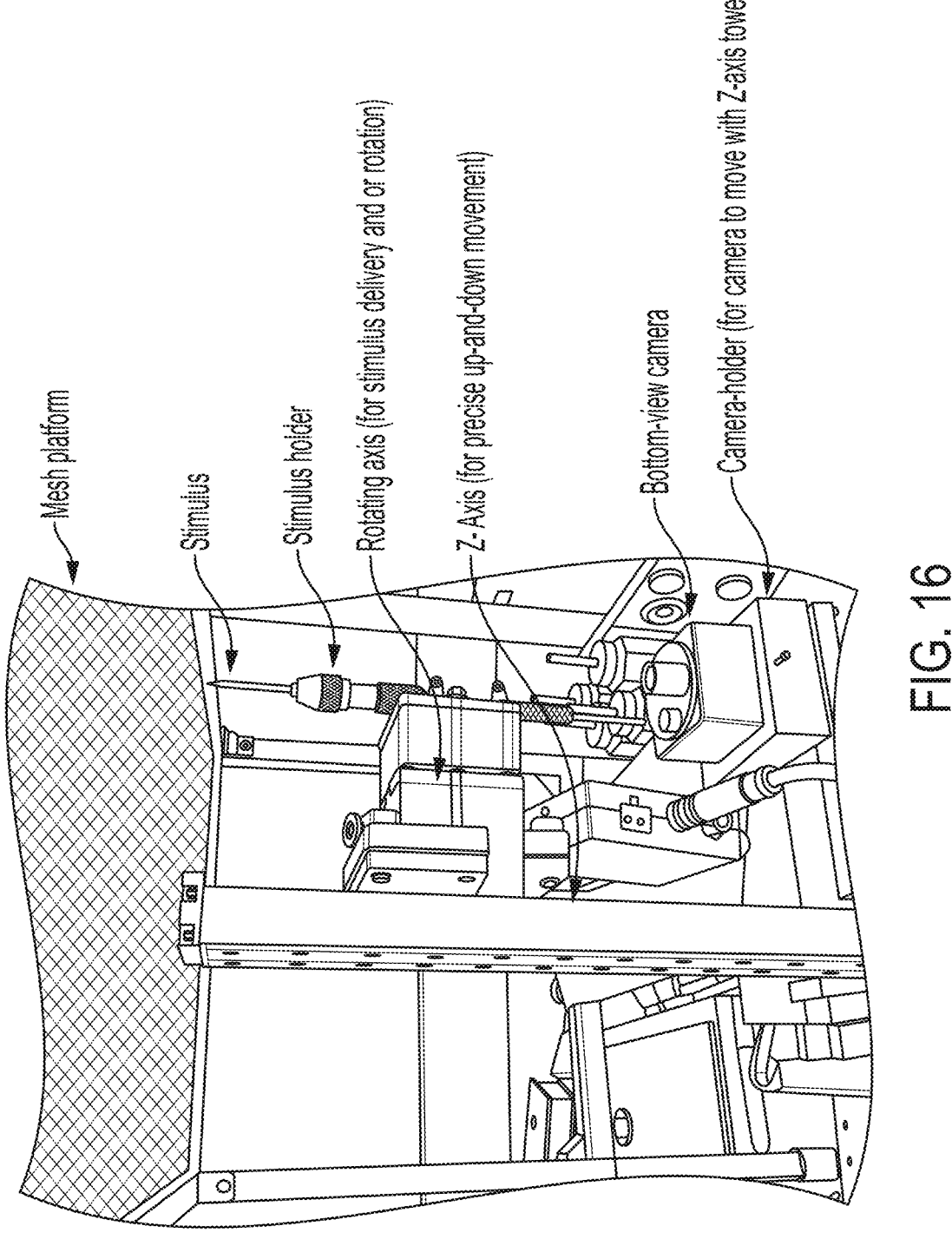
FIG. 16 is a detail of the Z axis assembly depicted in FIG. 15.
Figure 17:
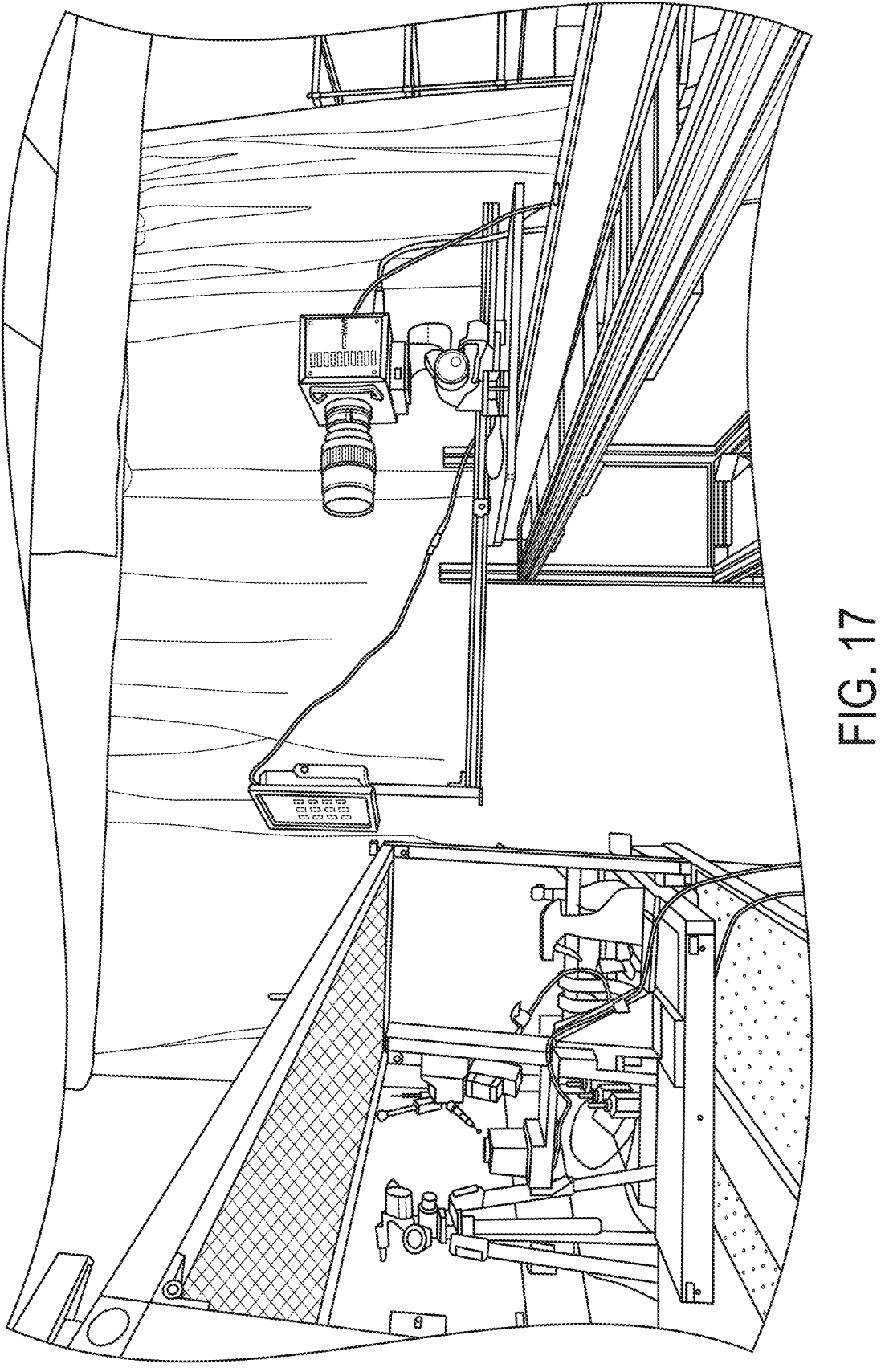
FIG. 17 depicts the FIG. 15 apparatus from a different perspective.
Figure 18:
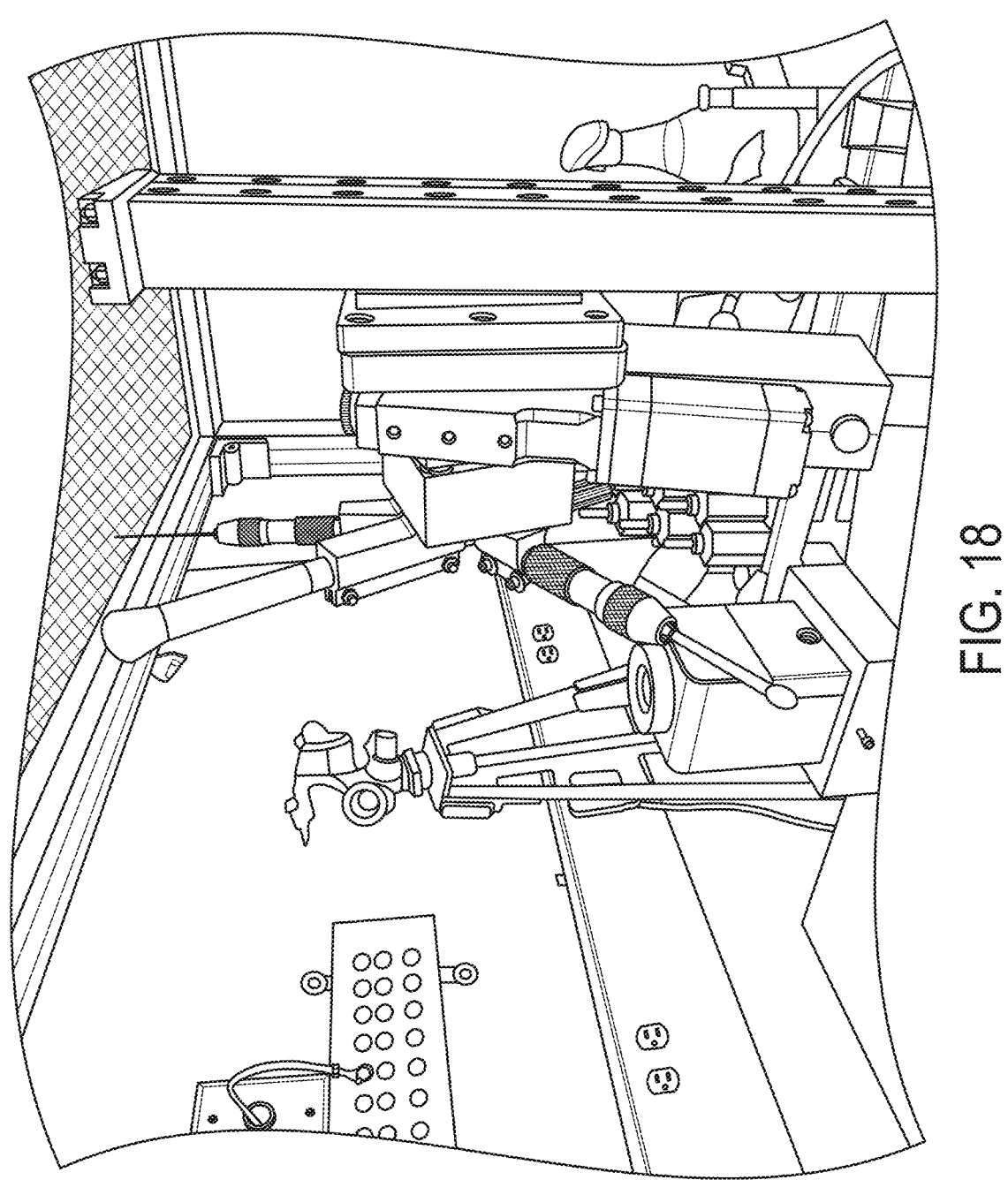
FIG. 18 depicts the FIG. 16 assembly from a different perspective.

FIG. 15 depicts a third ARM embodiment that reduces stimulus variability and allows for remote delivery of the stimuli, and FIG. 16 is a detail of the Z axis assembly depicted in FIG. 15. This ARM embodiment delivers stimuli (e.g., mechanical stimuli) in an automated and reproducible way. It can be operated by a local operator or remotely controlled. FIG. 17 depicts the FIG. 15 apparatus from a different perspective; and FIG. 18 depicts the FIG. 16 assembly from a different perspective.

Things that can affect a mouse's pain behavior at baseline include genetics, the animal's housing, developmental conditions, analysis, the nature and characteristics of the stimulus, and the experimental conditions. The ARM advantageously makes the stimulus much more repeatable than was possible with the prior art manual approach.

The ARM includes a side-view camera, a bottom-view camera, a mesh platform that supports the animal being tested, a plexiglass chamber, the automated mechanical stimulator moving across x, y, and z directions (e.g., controlled manually by a joystick or automatically using appropriate software) and a set of stimulus tools that are mounted on the mechanical stimulator. Examples of suitable stimulus tools that are appropriate for use in animal studies include nylon filaments, von Frey hairs, a cotton swab, a pinpric and a make up brush. The illustrated embodiment relies on a rotary assembly to rotate the desired tool to the top position, after which the desired tool can be used to stimulate the animal by momentarily moving the selected tool upwards so that it makes contact with the animal, then returning the tool to its original position (where it does not contact the animal).

The animal is placed on the mesh platform (e.g., in a transparent acrylic chamber) and can be viewed from the side using the side-view camera. The ARM includes a holder for the bottom-view camera that allows visualization of the paws of the animals in order to target them with its automated mechanical stimuli (moving across the x, y, and z axes). One of the stimulus tools is selected for stimulating the animal by rotating the selected tool to the top position.

The ARM moves the Z axis assembly (which includes that stimulus tool) to a location where it can stimulate the animal (e.g., by applying a stimulus such as a vertical (Z-axis) pin prick to the animal's paw), and also move the stimulus tool away from that location until such time that the stimulus tool is used again. The Z axis assembly includes an actuator that is configured to, in response to receipt of at least one input command, move a member up by a precise amount and subsequently moved the member back down. In the illustrated embodiment, all of the tools are connected to this member. In other embodiments (not shown), only the active tool is connected to this member.

The operator can manually select one of the stimulus tools by rotating the selected tool to the top position. Alternatively, the ARM can automatically rotate any of the available stimulus tools to the top position, after which the mechanical stimulator will stimulate the animal using whichever tool is at the top position. In alternative embodiments, different approaches for selecting a desired tool can be used.

The ARM can be programmed to deliver stimuli with a specific trajectory, speed and or force. The ARM can be used both with the experimenter in the room or outside the room (remotely). This can be done using the cameras that can be controlled and moved remotely with a computer. Mechanical stimuli can be delivered using the joystick and or the software.

The ARM provides for testing laboratory animal pain and other sensory times (touch, temperature, etc.). They ARM can be used to apply mechanical stimulation to the animal being tested (e.g., a mouse) without an experimenter in the room, and do it repeatedly in an identical manner improving the objectivity, reproducibility, and consistency of the resulting data. The ARM therefore solves the problem of stimulus variation introduced by the experimenter(s). It can work with an automated pain assessment platform as well as more traditional acute mechanical sensitivity assays, and can help in understanding pain chronification and identifying novel analgesics.

The ARM can measure mechanical sensitivity and/or pain. It can also be adapted to deliver thermal and optogenetic stimuli remotely by replacing the stimulus tools identified above with a custom stimulus tool that is heated to a predetermined temperature (e.g., 130-150° F.) selected to cause the animal to recoil its paw without causing tissue damage.

Figure 19:
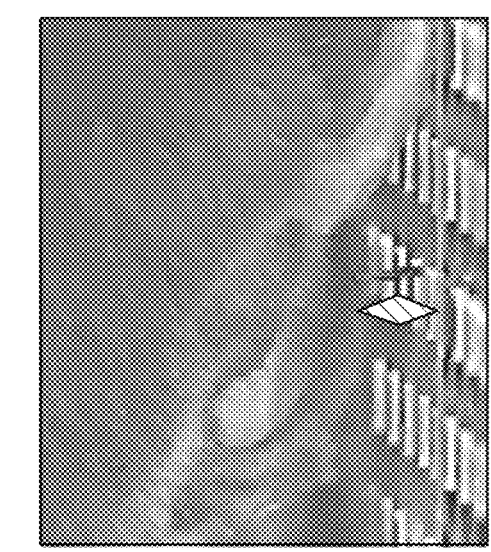
FIG. 19 depicts the inconsistent nature of the prior art manual approach for delivering pinprick stimuli.
Figure 19:
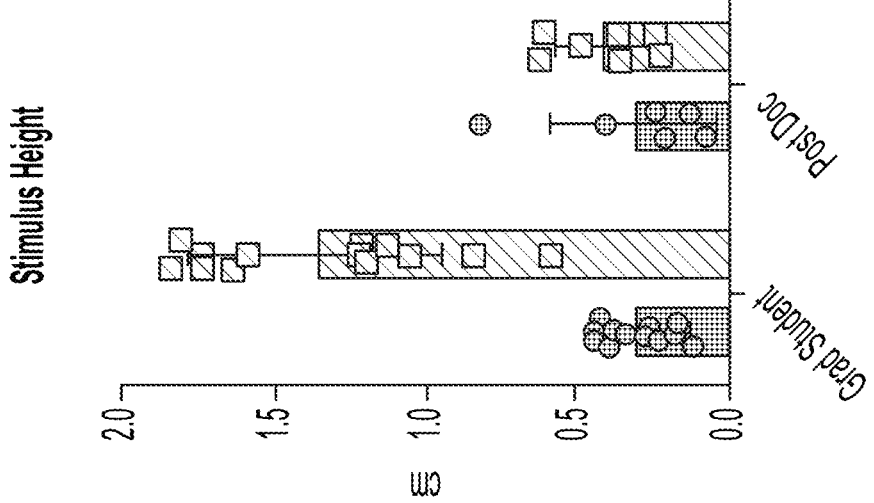
Figure 20:
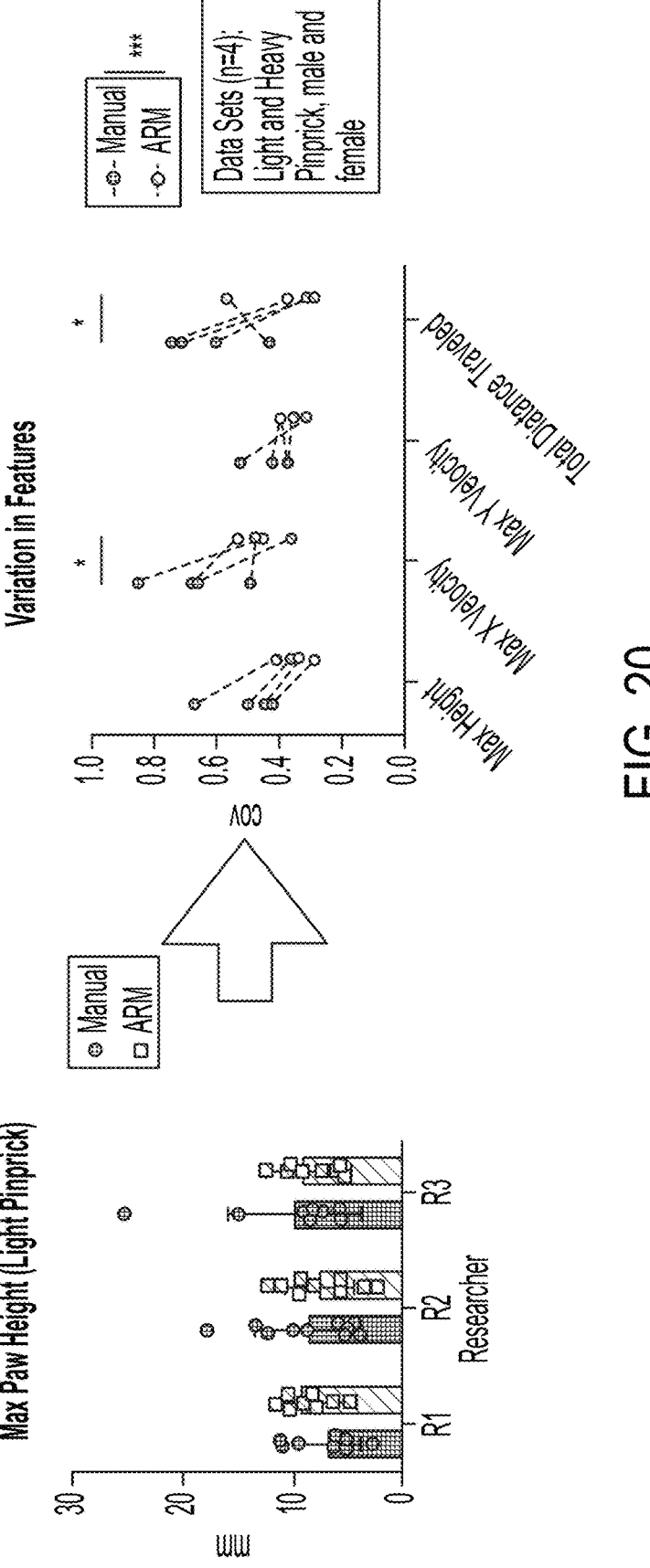
FIG. 20 depicts how the third ARM embodiment provides much more consistent stimuli and increases repeatability as compared to manual pinpricks.

FIG. 19 depicts the inconsistent nature of the prior art manual approach for delivering pinprick stimuli. And FIG. 20 depicts how the ARM apparatus described herein provides much more consistent stimuli and increases repeatability as compared to manual pinpricks.

Figure 21:
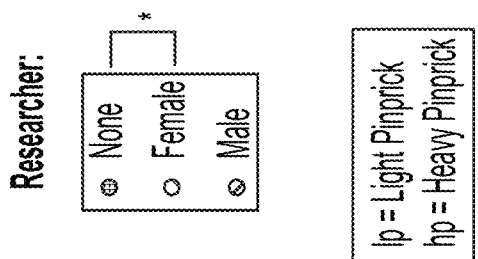
FIG. 21 depicts how the sex of the researcher affects the pain behavior in female mice.
Figure 21:
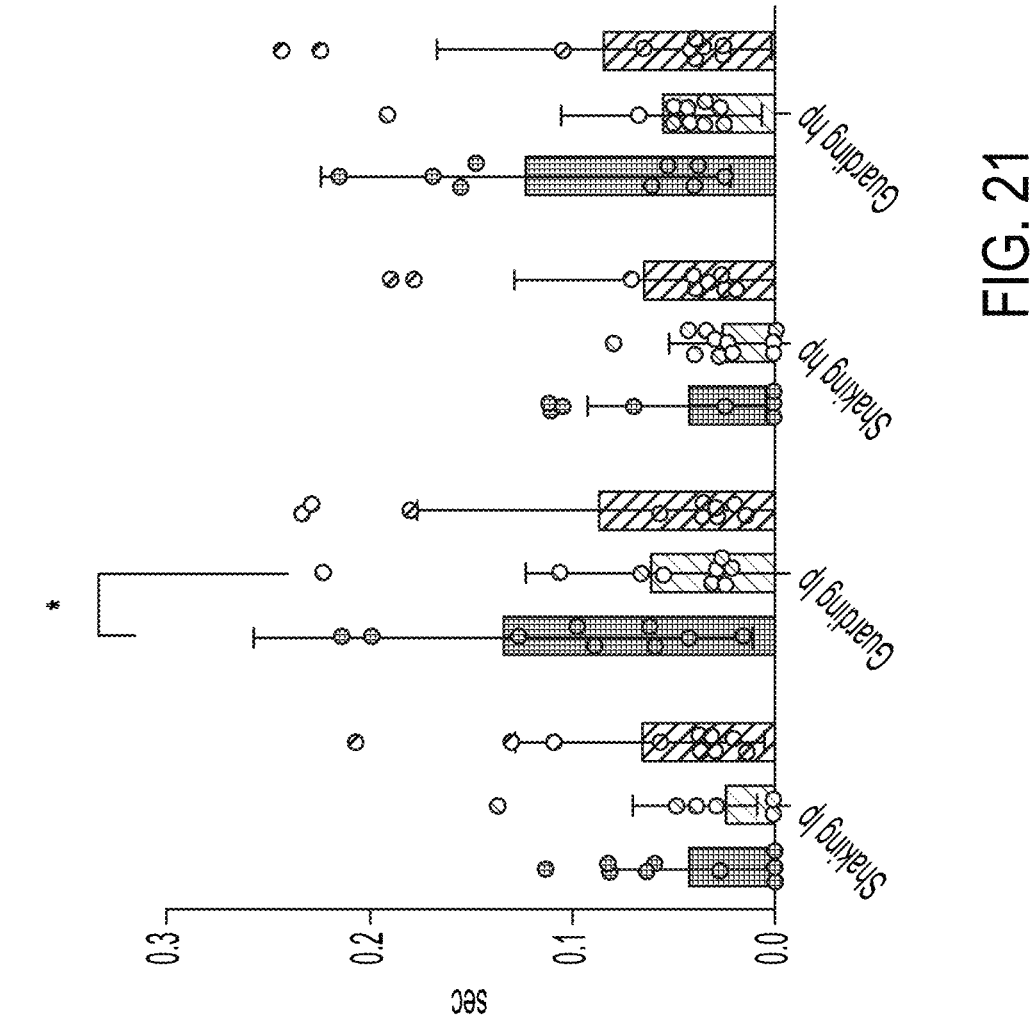
Figure 22:
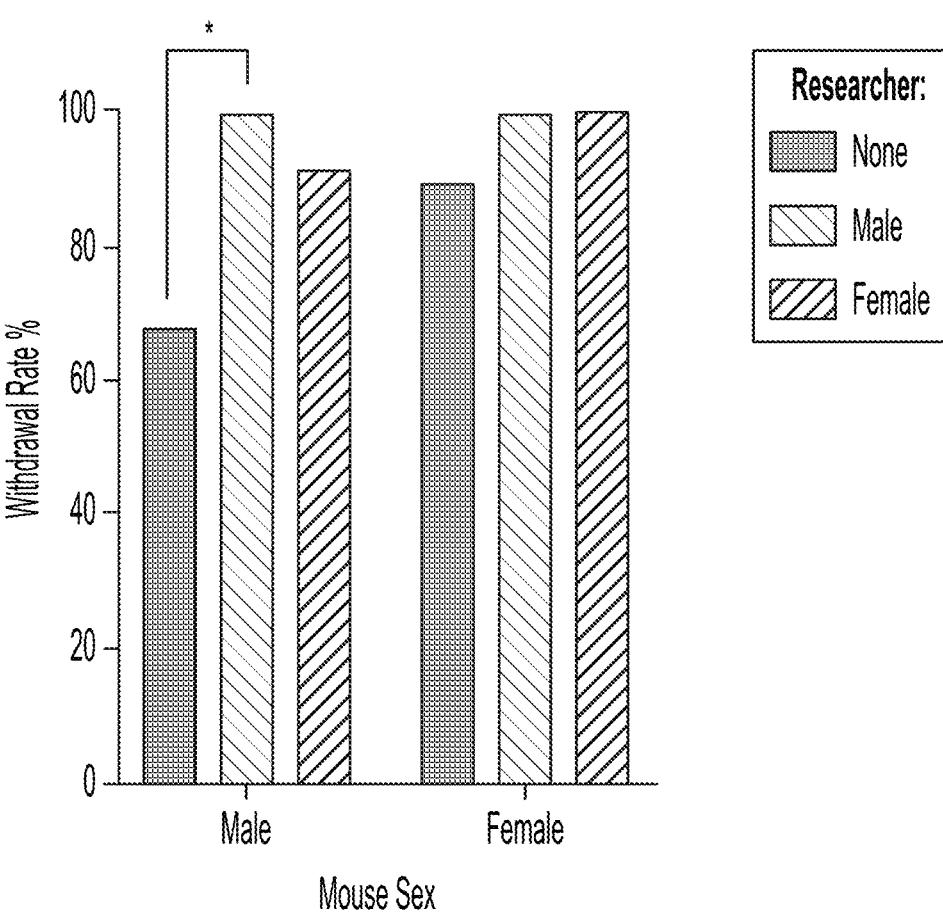
FIG. 22 depicts how the sex of the researcher affects the withdrawal rate for both male and female mice.

Experiments performed using the ARM typically take 50% less time than prior art approaches, and tracking/analysis can be reduced from days to hours. Advantageously, the ARM decreases variability in behavioral data compared to the prior art manual approach for pinpricks. In addition, the ARM overcomes a serious problem with the prior art, which is that the presence of a researcher effects the responses of the animals in a sex dependent manner (i.e., depending on the sex of the person who is performing the experiment), as depicted in FIGS. 21 and 22. More specifically, FIG. 21 depicts how the sex of the researcher affects the pain behavior in female mice, and FIG. 22 depicts how the sex of the researcher affects the withdrawal rate for both male and female mice.

The ARM apparatus can be used to research heightened pain states, and the force that the tools apply to the animals can be controlled in some embodiments.

Example 4

Figure 23:
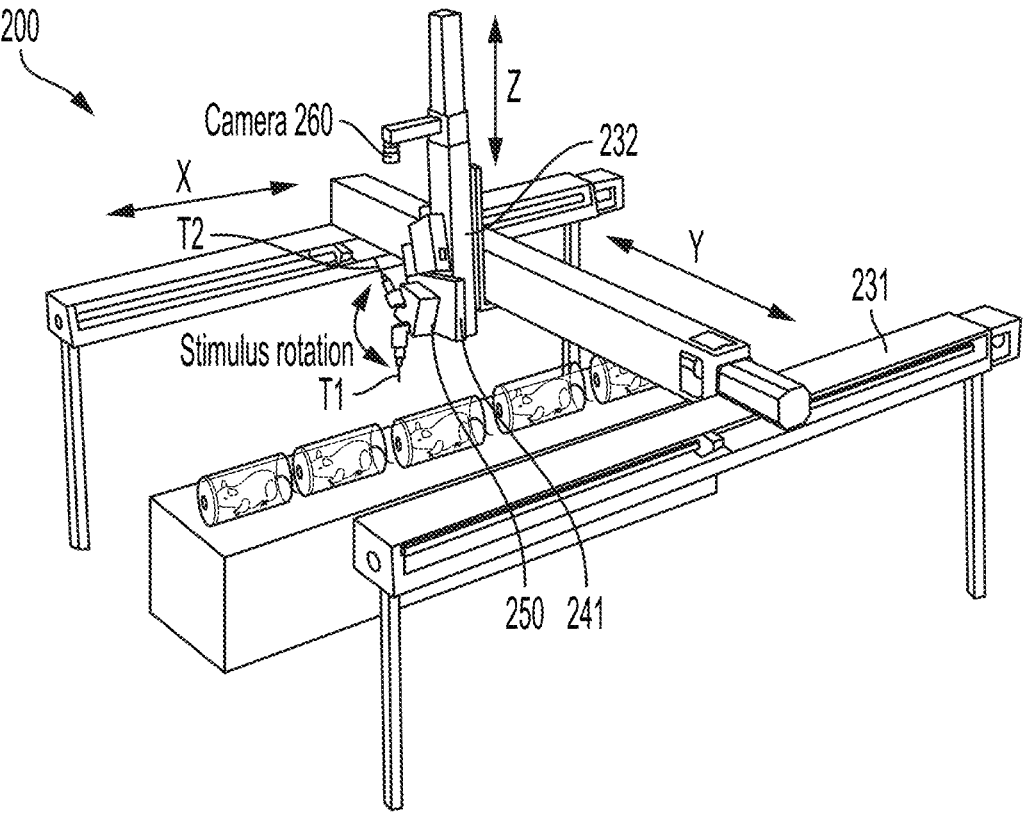
FIG. 23 depicts a fourth ARM embodiment that reduces stimulus variability and allows for remote delivery of the stimuli.

FIG. 23 depicts a fourth ARM embodiment that reduces stimulus variability and allows for remote delivery of the stimuli, this embodiment is generally similar to the first and second embodiments described above, except that the stimulus is applied from above the animal (e.g., to the top of the animal's head) instead of from below.

This embodiment 200 uses a gantry set up of linear stages. A frame supported by four legs will support an XY stage 231, 232, with an actuator 241 suspended perpendicular between them. The stimulus delivery device will be suspended from this actuator 241, and it can be implemented using any of the approaches described above for the actuator 41 of the FIG. 1 embodiment (e.g., a linear stage suspended vertically for mechanical stimulation). A rotating component 250 for applying brush stimulus and switching between stimuli is provided, as is a top-view camera 260 to aim either manually or automated, and a holder for either mechanical, air-puff, cold, optogenetic, thermal, or chemical stimulus. For mechanical stimulus a force sensor can be incorporated into the stimulus mount as previously described to determine when precisely stimulus makes contact with the head. Mice be place on a platform within the legs of and under the gantry setup. They will either be placed in rectangular or tube-shaped chambers that will restrict their movement and have an opening at the top for stimulus to be applied. This embodiment 200 can be used to aim at and deliver stimuli to either the forehead or back of the mouse. As with the first and second embodiments, control via specialized ARM software will allow for manual in-person or remotely with a standard controller, or fully automated aiming.

This embodiment 200 can be used to apply a stimulus to a body part of an animal from above. It comprises a motorized XY stage 231-232 positioned above the animal. The XY stage has a base 231 and a movable part 232. Operation of this XY stage 231-232 is similar to the XY stage 31-32 of the FIG. 1 embodiment, except that it is inverted.

This embodiment also has an actuator 241 mounted to the movable part 232 of the XY stage beneath the XY stage, and the actuator is configured to, in response to receipt of at least one input command, move a member down by a precise amount and subsequently move the member back up. Operation of this actuator 241 is similar to the actuator 41 of the FIG. 1 embodiment, except that it moves the member downward to apply the stimulus and moves it upwards to cease the stimulus.

A first tool T1 is mounted to the member of the actuator 241, and the first tool is configured to apply the stimulus to the body part by (a) making contact with the body part when the member of the actuator 241 moves down, and (b) ceasing contact with the body part when the member moves back up.

A side-view camera (not shown, but similar to the side-view camera 70 of the FIG. 1 embodiment) is positioned to capture side views of animals that are positioned in a confined space. A top-view camera 260 is positioned above the confined space to allow visualization of the body part so that the body part can be targeted by the first tool T1. Operation of this top-view camera 260 is similar to the bottom-view camera 60 of the FIG. 1 embodiment, except that it is aimed downward to visualize the top of the animal's head.

At least one controller (not shown, but similar to the controller 80 of the FIG. 1 embodiment) is programmed and configured to instruct the XY stage 231-232 to move the movable part 232 of the XY stage to a location in space at which the first tool T1 is positioned directly above the body part, and subsequently send the at least one input command to the actuator 241.

Optionally, the first tool T1 can be mounted to the member of the actuator 241 via a rotating component 250 positioned between the first tool and the member of the actuator 241. For this option, the apparatus 200 further comprises at least one additional tool mounted to the rotating component 250 so that, depending on a position of the rotating component, a different one of the tools will point down. The rotating component 250 is configured to rotate to a given one of a plurality of positions based on a command that arrives from the at least one controller, and the at least one controller is further programmed and configured to command the rotating component 250 to rotate to a position at which a given one of the tools points down.

At least one of a trajectory of the stimulus, a speed of the stimulus, and a force of the stimulus can be programmable, and the actuator 241 can be configured so that successive actuations of the actuator occur in an identical manner.

The at least one controller of this embodiment can be programmed and configured to instruct the side-view camera to begin capturing images 5-200 ms prior to sending the at least one input command to the actuator 241.

Optionally, this embodiment 200 can further comprise a user interface ((not shown, but similar to the user interface 85 of the FIG. 1 embodiment) configured to interface with the at least one controller, and the user interface is positioned remotely with respect to the XY stage 231-232 and the actuator 241 to an extent where the animal will be unaware of a presence of a human operator who is using the user interface.

Conclusion

The methods described herein can be implemented, in whole or in part, in software that can be stored in computer-readable media for execution by a computer processor. For example, the computer-readable media can be volatile memory (e.g., RAM) non-volatile memory (e.g., ROM, PROM, EPROM, solid state drives, hard drives, etc.). Additionally or alternatively, the methods described herein can be implemented in computer hardware including but not limited to one or more application-specific integrated circuits (ASICs).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying a stimulus to a paw of an animal that is supported by a platform, the platform having a plurality of openings through which the stimulus can be applied to the paw, the apparatus comprising:

a motorized XY stage positioned beneath the platform, the XY stage having a base and a movable part;

an actuator mounted to the movable part of the XY stage, wherein the actuator is configured to, in response to receipt of at least one input command, move a member up by a precise amount and subsequently move the member back down;

a first tool mounted to the member, wherein the first tool is configured to apply the stimulus to the paw by (a) making contact with the paw through one of the openings in the platform when the member moves up, and (b) ceasing contact with the paw when the member moves back down;

a first side-view camera positioned to capture side views of animals that are positioned on the platform;

a bottom-view camera positioned below the platform to allow visualization of the animal's paw so that the paw can be targeted by the first tool;

a first linear stage, wherein the first side-view camera is mounted on the first linear stage and wherein the first linear stage is configured to move the first side-view camera horizontally; and at least one controller programmed and configured to instruct the XY stage to move the movable part of the XY stage to a location in space at which the first tool is positioned directly beneath the paw, and subsequently send the at least one input command to the actuator.

2. The apparatus of claim 1, further comprising the platform.

3. The apparatus of claim 1, wherein the first tool is mounted to the member via a rotating component positioned between the first tool and the member, wherein the apparatus further comprises at least one additional tool mounted to the rotating component so that, depending on a position of the rotating component, a different one of the tools will point up.

4. The apparatus of claim 3, wherein the rotating component is configured to rotate to a given one of a plurality of positions based on a command that arrives from the at least one controller, and wherein the at least one controller is further programmed and configured to command the rotating component to rotate to a position at which a given one of the tools points up.

5. The apparatus of claim 1, further comprising a user interface configured to interface with the at least one controller, wherein the user interface is positioned remotely with respect to the XY stage and the actuator to an extent where the animal will be unaware of a presence of a human operator who is using the user interface.

6. The apparatus of claim 1, further comprising a red or infrared light source that is aimed to illuminate animals that are positioned on the platform.

* * * * *